United States Patent
Jeanguenat et al.

(10) Patent No.: US 11,071,300 B2
(45) Date of Patent: *Jul. 27, 2021

(54) PESTICIDALLY ACTIVE PYRAZOLE DERIVATIVES

(71) Applicant: SYNGENTA PARTICIPATIONS AG, Basel (CH)

(72) Inventors: André Jeanguenat, Stein (CH); Myriem El Qacemi, Stein (CH); André Stoller, Stein (CH); Aurelien Bigot, Stein (CH); Denis Gribkov, Münchwilen (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/624,710

(22) PCT Filed: Jun. 18, 2018

(86) PCT No.: PCT/EP2018/066113
§ 371 (c)(1),
(2) Date: Dec. 19, 2019

(87) PCT Pub. No.: WO2018/234240
PCT Pub. Date: Dec. 27, 2018

(65) Prior Publication Data
US 2020/0128827 A1    Apr. 30, 2020

(30) Foreign Application Priority Data

Jun. 19, 2017 (EP) ..................... 17176735
Jun. 20, 2017 (EP) ..................... 17176950

(51) Int. Cl.
*A01N 43/56* (2006.01)
*A01N 43/80* (2006.01)
*C07D 401/14* (2006.01)
*C07D 403/04* (2006.01)
*C07D 413/02* (2006.01)

(52) U.S. Cl.
CPC ............. *A01N 43/56* (2013.01); *A01N 43/80* (2013.01); *C07D 401/14* (2013.01); *C07D 403/04* (2013.01); *C07D 413/02* (2013.01)

(58) Field of Classification Search
CPC .. C07D 401/14; C07D 403/04; C07D 413/02; A01N 43/56
See application file for complete search history.

(56) References Cited

U.S. PATENT DOCUMENTS 10,750,742 B2 * 8/2020 Jeanguenat ............ A01N 43/56

FOREIGN PATENT DOCUMENTS

| WO | 2004046129 A2 | 6/2004 |
| WO | 2012107434 A1 | 8/2012 |
| WO | 2017012970 A2 | 1/2017 |
| WO | 2017108569 A1 | 6/2017 |

OTHER PUBLICATIONS

Extended European Search Report for EP Application No. 17176950.8 dated Aug. 30, 2017.
International Search Report for International Application No. PCT/EP2018/066113 dated Jul. 13, 2018.

* cited by examiner

*Primary Examiner* — Kamal A Saeed
(74) *Attorney, Agent, or Firm* — Bakerhostetler; Toni-Junell Herbert

(57) ABSTRACT

Compounds of formula (I), as defined herein, to processes for preparing them, to pesticidal, in particular insecticidal, acaricidal, molluscicidal and nematicidal compositions comprising them and to methods of using them to combat and control pests such as insect, acarine, mollusc and nematode pests.

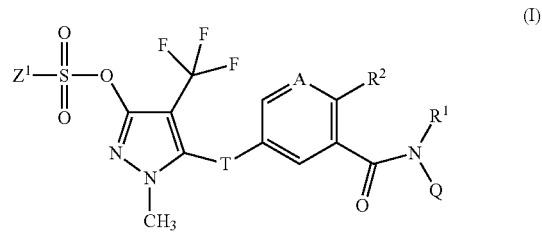

11 Claims, No Drawings

PESTICIDALLY ACTIVE PYRAZOLE DERIVATIVES

CROSS-REFERENCE TO RELATED APPLICATIONS

This application is a 371 National Stage application of International Application No. PCT/EP2018/066113 filed Jun. 18, 2018 which claims priority to EP 17176735.3, filed Jun. 19, 2017, and EP 17176950.8, filed Jun. 20, 2017, the entire contents of which applications are hereby incorporated by reference.

The present invention relates to pyrazole derivatives, to processes for preparing them, to intermediates for preparing them, to pesticidal, in particular insecticidal, acaricidal, molluscicidal and nematicidal compositions comprising those derivatives and to methods of using them to combat and control pests such as insect, acarine, mollusc and nematode pests.

It has now surprisingly been found that certain pyrazole derivatives have highly potent insecticidal properties. Other compounds in this area are known from WO2014/122083, WO2012/107434, WO2015/067646, WO2015/067647, WO2015/067648, WO2015/150442 and WO2010/051926.

Thus, as embodiment 1, the present invention relates to a compound of formula (I),

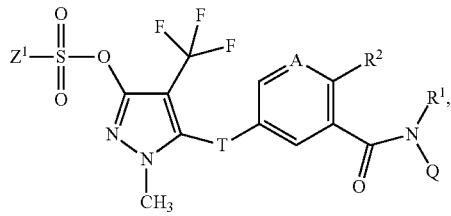

wherein
$Z^1$ is selected from $C_1$-$C_4$-haloalkyl and F;
T is selected from

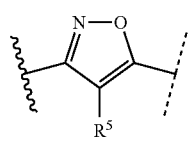  T1

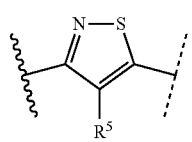  T2

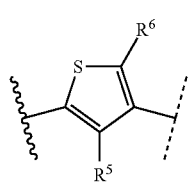  T3

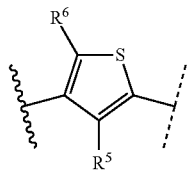  T4

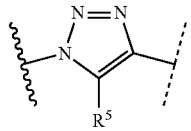  T5

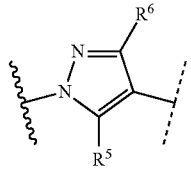  T6 wherein ⊢ indicates the bond to the pyrazole group;
$R^5$ and $R^6$ are independently selected from H, methyl and trifluoromethoxy;
A is selected from C—H and N;
$R^2$ is selected from H, methyl, trifluoromethyl and halogen;
$R^1$ is selected from H, $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, formyl, $C_1$-$C_6$-alkoxycarbonyl, aryl($C_0$-$C_3$)-alkyl and heteroaryl($C_0$-$C_3$)-alkyl, wherein each of $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, $C_1$-$C_6$-alkoxycarbonyl, aryl($C_0$-$C_3$)-alkyl and heteroaryl($C_0$-$C_3$)-alkyl is unsubstituted or substituted with 1 to 10 substituents independently selected from halogen, cyano, $C_1$-$C_6$-alkoxy and $C_1$-$C_6$-alkoxycarbonyl;
Q is selected from H, hydroxy, HC(=O)—, $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N— $C_1$-$C_6$-alkylamino, N— $C_1$-$C_6$-alkylcarbonylamino and N,N-di($C_1$-$C_6$-alkyl)amino, wherein each of $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N— $C_1$-$C_6$-alkylamino, N— $C_1$-$C_6$-alkylcarbonylamino and N,N-di($C_1$-$C_6$-alkyl)amino is unsubstituted or substituted with 1 to 10 substituents independently selected from halogen, hydroxyl, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;
wherein the compound of formula (I) is not
[5-[4-[4-chloro-3-[(1-cyanocyclopropyl)carbamoyl]phenyl] pyrazol-1-yl]-1-methyl-4-(trifluoromethyl)pyrazol-3-yl] trifluoromethanesulfonate, or
[5-[4-[4-chloro-3-(cyanocyclopropylcarbamoyl)phenyl] pyrazol-1-yl]-1-methyl-4-(trifluoromethyl)pyrazol-3-yl] 1,1,2,2,3,3,4,4,4-nonafluorobutane-1-sulfonate, or
[5-[4-[4-chloro-3-(cyclopropylcarbamoyl)phenyl]pyrazol-1-yl]-1-methyl-4-(trifluoromethyl)pyrazol-3-yl]1,1,2,2,3,3,4,4,4-nonafluorobutane-1-sulfonate;
or an agrochemically acceptable salt or N-oxide thereof.

The compounds disclaimed in embodiment 1 are disclosed in patent application PCT/EP2016/081167 (WO2017/108569) as examples 16, 36 and 37.

Embodiment 2

A compound or salt according to embodiment 1 of formula (I)

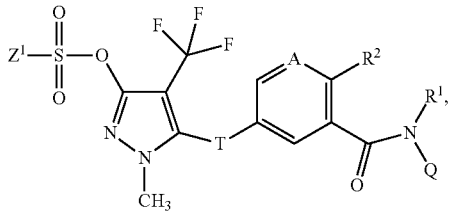

wherein
$Z^1$ is selected from $C_1$-$C_4$-haloalkyl and F;
T is selected from

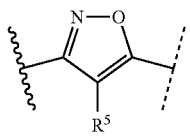

T1

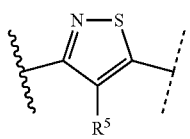

T2

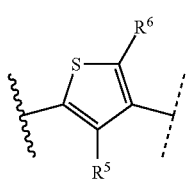

T3

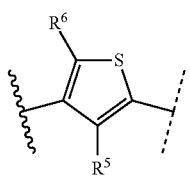

T4

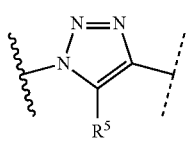

T5

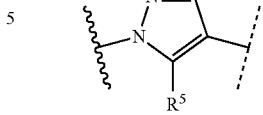

T6 wherein ⊢ indicates the bond to the pyrazole group;
$R^5$ and $R^6$ are independently selected from H, methyl and trifluoromethoxy;
A is selected from C—H and N;
$R^2$ is selected from H, methyl, trifluoromethyl and halogen;
$R^1$ is selected from H, $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, formyl, $C_1$-$C_6$-alkoxycarbonyl, aryl($C_0$-$C_3$)-alkyl and heteroaryl($C_0$-$C_3$)-alkyl, wherein each of $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, $C_1$-$C_6$-alkoxycarbonyl, aryl($C_0$-$C_3$)-alkyl and heteroaryl($C_0$-$C_3$)-alkyl is unsubstituted or substituted with 1 to 10 substituents independently selected from halogen, cyano, $C_1$-$C_6$-alkoxy and $C_1$-$C_6$-alkoxycarbonyl;
Q is selected from H, hydroxy, HC(=O)—, $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N—$C_1$-$C_6$-alkylamino, N—$C_1$-$C_6$-alkylcarbonylamino and N,N-di($C_1$-$C_6$-alkyl)amino, wherein each of $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N—$C_1$-$C_6$-alkylamino, N—$C_1$-$C_6$-alkylcarbonylamino and N,N-di($C_1$-$C_6$-alkyl)amino is unsubstituted or substituted with 1 to 10 substituents independently selected from halogen, hydroxyl, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;
with the proviso that when T is T6, A is C—H, $R^5$ and $R^6$ are H, $Z^1$ is $CF_3$ or $CF_2CF_2CF_2CF_3$, and Q is cyclopropyl or 1-cyanocyclopropyl, then $R^1$ is not H;
or an agrochemically acceptable salt or N-oxide thereof.

Embodiment 3

A compound or salt according to embodiment 1 or 2 of formula (I)

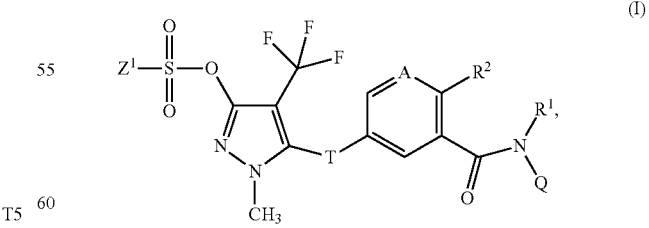

wherein
$Z^1$ is selected from
F,
$CF_2CF_3$,
$CF_2CF_2Cl$,

CF$_2$CFCl$_2$,
CF$_2$CF$_2$CF$_3$,
CF(CF$_3$)(CF$_3$),
CF$_2$CF$_2$CF$_2$Cl,
CF(CF$_3$)(CF$_2$Cl),
CF$_2$CF$_2$CFCl$_2$,
CF(CF$_3$)(CFCl$_2$),
CF$_2$CF$_2$CF$_2$CF$_3$,
CF(CF$_3$)CF$_2$CF$_3$,
CF$_2$CF(CF$_3$)(CF$_3$),
C(CF$_3$)(CF$_3$)(CF$_3$);

T is selected from

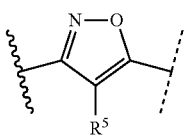 T1

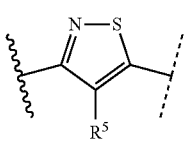 T2

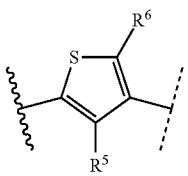 T3

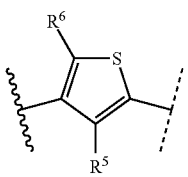 T4

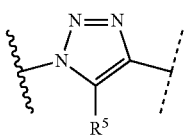 T5

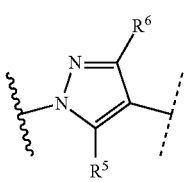 T6 wherein ⊢ indicates the bond to the pyrazole group;
R$^5$ and R$^6$ are independently selected from H, methyl and trifluoromethoxy;
A is selected from C—H and N;
R$^2$ is selected from H, methyl, trifluoromethyl and halogen;
R$^1$ is selected from H, C$_1$-C$_6$-alkyl, C$_2$-C$_6$ alkenyl, C$_2$-C$_6$ alkynyl, C$_3$-C$_7$ cycloalkyl, C$_3$-C$_7$ cycloalkyl-C$_1$-C$_3$-alkyl, C$_1$-C$_6$-alkylcarbonyl, formyl, C$_1$-C$_6$-alkoxycarbonyl, aryl(C$_0$-C$_3$)-alkyl and heteroaryl(C$_0$-C$_3$)-alkyl, wherein each of C$_1$-C$_6$-alkyl, C$_2$-C$_6$ alkenyl, C$_2$-C$_6$ alkynyl, C$_3$-C$_7$ cycloalkyl, C$_3$-C$_7$ cycloalkyl-C$_1$-C$_3$-alkyl, C$_1$-C$_6$-alkylcarbonyl, C$_1$-C$_6$-alkoxycarbonyl, aryl(C$_0$-C$_3$)-alkyl and heteroaryl(C$_0$-C$_3$)-alkyl is unsubstituted or substituted with 1 to 10 substituents independently selected from halogen, cyano, C$_1$-C$_6$-alkoxy and C$_1$-C$_6$-alkoxycarbonyl;

Q is selected from H, hydroxy, HC(=O)—, C$_1$-C$_6$-alkyl, C$_1$-C$_6$-alkoxy, C$_3$-C$_6$ alkenyl, C$_3$-C$_6$ alkynyl, C$_3$-C$_7$ cycloalkyl, C$_3$-C$_7$ heterocycloalkyl, C$_3$-C$_7$ cycloalkyl-C$_1$-C$_3$-alkyl, C$_1$-C$_3$-alkyl-C$_3$-C$_7$ cycloalkyl, aryl(C$_0$-C$_3$)-alkyl, heteroaryl(C$_0$-C$_3$)-alkyl, N—C$_1$-C$_6$-alkylamino, N—C$_1$-C$_6$-alkylcarbonylamino and N,N-di(C$_1$-C$_6$-alkyl)amino, wherein each of C$_1$-C$_6$-alkyl, C$_1$-C$_6$-alkoxy, C$_3$-C$_6$ alkenyl, C$_3$-C$_6$ alkynyl, C$_3$-C$_7$ cycloalkyl, C$_3$-C$_7$ heterocycloalkyl, C$_3$-C$_7$ cycloalkyl-C$_1$-C$_3$-alkyl, C$_1$-C$_3$-alkyl-C$_3$-C$_7$ cycloalkyl, aryl(C$_0$-C$_3$)-alkyl, heteroaryl(C$_0$-C$_3$)-alkyl, N—C$_1$-C$_6$-alkylamino, N—C$_1$-C$_6$-alkylcarbonylamino and N,N-di(C$_1$-C$_6$-alkyl) amino is unsubstituted or substituted with 1 to 10 substituents independently selected from halogen, hydroxyl, nitro, amino, cyano, C$_1$-C$_6$-alkoxy, C$_1$-C$_6$-alkoxycarbonyl, hydroxycarbonyl, C$_1$-C$_6$-alkylcarbamoyl, C$_3$-C$_6$-cycloalkylcarbamoyl and phenyl;

with the proviso that when T is T6, A is C—H, R$^5$ and R$^6$ are H, Z$^1$ is CF$_3$ or CF$_2$CF$_2$CF$_2$CF$_3$, and Q is cyproyl or 1-cyanocyclopropyl, then R$^1$ is not H;

or an agrochemically acceptable salt or N-oxide thereof.

Embodiment 4

A compound or salt according to any one of embodiments 1 to 3 wherein

T is selected from

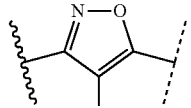 T1

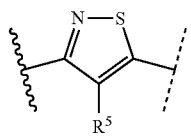 T2

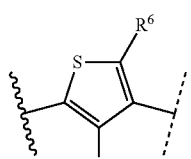 T3

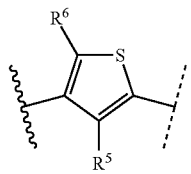 T4

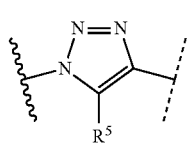 T5

Embodiment 5

A compound or salt according to any one of embodiments 1 to 3 wherein
T is

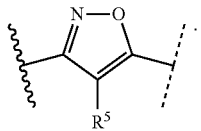

T1

Embodiment 6

A compound or salt according to any one of embodiments 1 to 3 wherein
T is

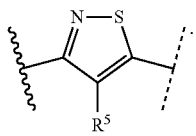

T2

Embodiment 7

A compound or salt according to any one of embodiments 1 to 3 wherein
T is

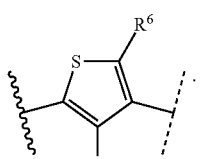

T3

Embodiment 8

A compound or salt according to any one of embodiments 1 to 3 wherein
T is

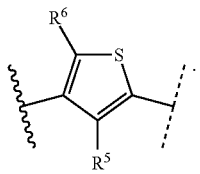

T4

Embodiment 9

A compound or salt according to any one of embodiments 1 to 3 wherein
T is

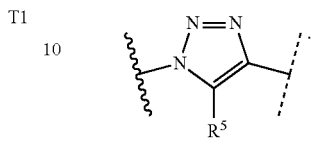

T5

Embodiment 9.1

A compound or salt according to any one of embodiments 1 to 3 wherein
T is

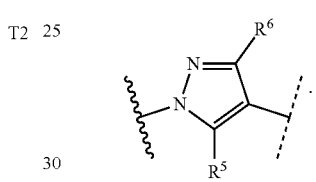

T6

Embodiment 10

A compound or salt according to any one of embodiments 1 to 9 wherein, $R^5$ and $R^6$ are H.

Embodiment 11

A compound or salt according to any one of embodiments 1 to 10 wherein $Z^1$ is F.

Embodiment 12

A compound or salt according to any one of embodiments 1 to 10 wherein $Z^1$ is selected from $-CF_2CF_3$, $-CF_2CF_2Cl$ and $-CF_2CFCl_2$.

Embodiment 13

A compound or salt according to any one of embodiments 1 to 10 wherein $Z^1$ is $-CF_2CF_3$.

Embodiment 14

A compound or salt according to any one of embodiments 1 to 10 wherein $Z^1$ is selected from $-CF_2CF_2CF_3$, $-CF(CF_3)(CF_3)$, $-CF_2CF_2CF_2Cl$ and $-CF(CF_3)(CF_2Cl)$.

Embodiment 15

A compound or salt according to any one of embodiments 1 to 10 wherein $Z^1$ is $-CF_2CF_2CF_3$.

Embodiment 16

A compound or salt according to any one of embodiments 1 to 10 wherein $Z^1$ is selected from —$CF_2CF_2CF_2CF_3$, —$CF(CF_3)CF_2CF_3$, —$CF_2CF(CF_3)(CF_3)$ and —$C(CF_3)(CF_3)(CF_3)$.

Embodiment 17

A compound or salt according to any one of embodiments 1 to 10 wherein $Z^1$ is —$CF_2CF_2CF_2CF_3$.

Embodiment 17.1

A compound or salt according to any one of embodiments 1 to 10 wherein $Z^1$ is —$CF(CF_3)(CF_3)$.

Embodiment 18

A compound or salt according to any one of embodiments 1 to 17 wherein $R^1$ is selected from H, $C_1$-$C_6$-alkyl, $C_2$-$C_6$ alkenyl, $C_2$-$C_6$ alkynyl, $C_1$-$C_6$-alkylcarbonyl and $C_1$-$C_6$-alkoxycarbonyl, wherein each of $C_1$-$C_6$-alkyl, $C_2$-$C_6$ alkenyl, $C_2$-$C_6$ alkynyl, $C_1$-$C_6$-alkylcarbonyl and $C_1$-$C_6$-alkoxycarbonyl is unsubstituted or substituted with 1 to 10 substituents independently selected from halogen, cyano, $C_1$-$C_6$-alkoxy and $C_1$-$C_6$-alkoxycarbonyl.

Embodiment 18.1

A compound or salt according to any one of embodiments 1 to 17 wherein $R^1$ is selected from H, methyl, ethyl, propyl, 2-methyl-propyl, 1-methyl-ethyl, —C(=O)—H, —C(=O)—$CH_3$, —$CH_2$—O-ethyl, —$CH_2$—O-methyl, —$CH_2$—O—$CH(CH_3)(CH_3)$, —$CH_2$—O—$(CH_3)(CH_3)(CH_3)$, —$CH_2$—$CH_2$—O-methyl, —$CH_2$—$CH_2$—O-ethyl, —$CH_2$—$CH_2$—$CH_2$—O-ethyl, —$CH_2$—C≡CH, —C(=O)—O-methyl, —C(=O)—O-ethyl, —C(=O)—O—$CH(CH_3)(CH_3)$, —C(=O)—$CH(CH_3)(CH_3)$, —C(=O)—$(CH_3)(CH_3)(CH_3)$, —$CH_2$—CN, —CH(methyl)-CN, —CH(ethyl)-CN, —C(=O)-ethyl, —CF=CF—$CF_3$ and —C(=O)—$CH_2$—O-methyl.

Embodiment 18.2

A compound or salt according to any one of embodiments 1 to 17 wherein $R^1$ is selected from H, methyl and ethyl.

Embodiment 19

A compound or salt according to any one of embodiments 1 to 18 wherein Q is $C_3$-$C_7$ cycloalkyl which is unsubstituted or substituted with 1 to 5 substituents independently selected from halogen, hydroxyl, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl.

Embodiment 20

A compound or salt according to any one of embodiments 1 to 18 wherein Q is $C_3$-$C_7$ cycloalkyl which is unsubstituted or substituted with 1 to 5 substituents independently selected from halogen, hydroxyl, nitro, amino and cyano.

Embodiment 21

A compound or salt according to any one of embodiments 1 to 18 wherein Q is $C_3$-$C_7$ cycloalkyl which is unsubstituted or substituted with 1 to 5 substituents independently selected from halogen, hydroxyl, nitro, amino and cyano.

Embodiment 22

A compound or salt according to any one of embodiments 1 to 18 wherein Q is cyclopropyl or 1-cyanocyclopropyl.

Embodiment 23

A compound or salt according to embodiment 1 of formula (Ia)

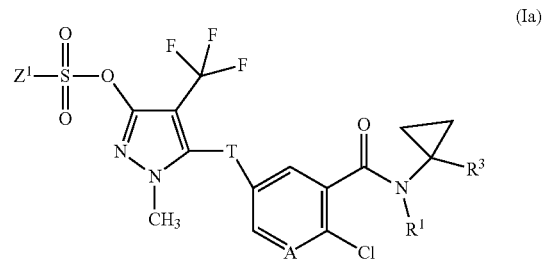

(Ia)

wherein
$Z^1$ is —$CF(CF_3)(CF_3)$;
$R^1$ is selected from H, $C_1$-$C_6$-alkyl, $C_2$-$C_6$ alkenyl, $C_2$-$C_6$ alkynyl, $C_1$-$C_6$-alkylcarbonyl and $C_1$-$C_6$-alkoxycarbonyl, wherein each of $C_1$-$C_6$-alkyl, $C_2$-$C_6$ alkenyl, $C_2$-$C_6$ alkynyl, $C_1$-$C_6$-alkylcarbonyl and $C_1$-$C_6$-alkoxycarbonyl is unsubstituted or substituted with 1 to 10 substituents independently selected from halogen, cyano, $C_1$-$C_6$-alkoxy and $C_1$-$C_6$-alkoxycarbonyl;
A is selected from C—H and N;
$R^3$ is selected from H and CN;
T is

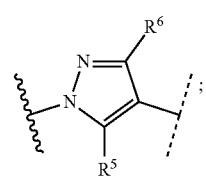

T6 or an agrochemically acceptable salt or N-oxide thereof.

Embodiment 23.1

A compound or salt according to embodiment 1 of formula (Ia)

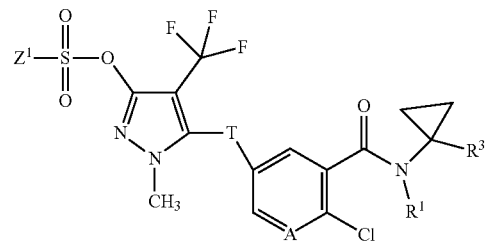

wherein $Z^1$ is —CF(CF$_3$)(CF$_3$);

$R^1$ is selected from H, methyl, ethyl, propyl, 2-methyl-propyl, 1-methyl-ethyl, —C(=O)—H, —C(=O)—CH$_3$, —CH$_2$—O-ethyl, —CH$_2$—O-methyl, —CH$_2$—O—CH(CH$_3$)(CH$_3$), —CH$_2$—O—(CH$_3$)(CH$_3$)(CH$_3$), —CH$_2$—CH$_2$—O-methyl, —CH$_2$—CH$_2$—O-ethyl, —CH$_2$—CH$_2$—CH$_2$—O-ethyl, —CH$_2$—C≡CH, —C(=O)—O-methyl, —C(=O)—O-ethyl, —C(=O)—O—CH(CH$_3$)(CH$_3$), —C(=O)—CH(CH$_3$)(CH$_3$), —C(=O)—(CH$_3$)(CH$_3$)(CH$_3$), —CH$_2$—CN, —CH(methyl)-CN, —CH(ethyl)-CN, —C(=O)-ethyl, —CF=CF—CF$_3$ and —C(=O)—CH$_2$—O-methyl;

A is selected from C—H and N;

$R^3$ is selected from H and CN;

T is

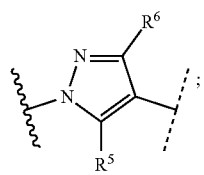

or an agrochemically acceptable salt or N-oxide thereof.

Embodiment 23.2

A compound or salt according to embodiment 1 of formula (Ia)

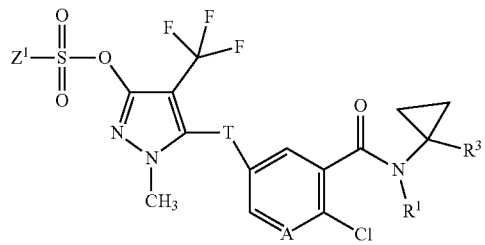

(Ia)

wherein $Z^1$ is —CF$_3$ and $R^1$ is selected from methyl and ethyl; or $Z^1$ is —CF$_2$CF$_3$ and $R^1$ is selected from H, methyl and ethyl; or $Z^1$ is —CF$_2$CF$_2$CF$_2$CF$_3$ and $R^1$ is selected from methyl and ethyl; or $Z^1$ is —F and $R^1$ is selected from H, methyl and ethyl; or $Z^1$ is —CF(CF$_3$)(CF$_3$) and $R^1$ is selected from H, methyl and ethyl; or $Z^1$ is —CF$_2$CF$_2$Cl and $R^1$ is selected from H, methyl and ethyl;

A is selected from C—H and N;

$R^3$ is selected from H and CN;

T is

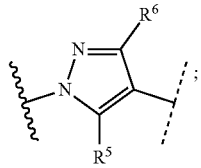

or an agrochemically acceptable salt or N-oxide thereof.

Embodiment 24

A compound or salt according to embodiment 1 of formula (Ia)

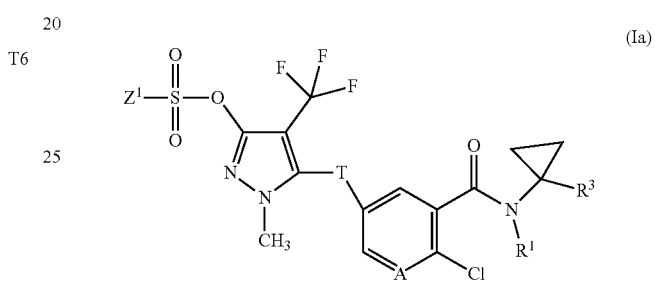

(Ia)

wherein $Z^1$ is —CF$_3$ and $R^1$ is selected from H, methyl and ethyl; or $Z^1$ is —CF$_2$CF$_3$ and $R^1$ is selected from H, methyl and ethyl; or $Z^1$ is —CF$_2$CF$_2$CF$_2$CF$_3$ and $R^1$ is selected from H, methyl and ethyl; or $Z^1$ is —F and $R^1$ is selected from H, methyl and ethyl; or $Z^1$ is —CF(CF$_3$)(CF$_3$) and $R^1$ is selected from H, methyl and ethyl; or $Z^1$ is —CF$_2$CF$_2$Cl and $R^1$ is selected from H, methyl and ethyl;

A is selected from C—H and N;

$R^3$ is selected from H and CN;

T is selected from

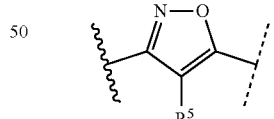

T1

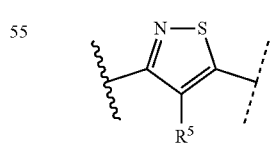

T2

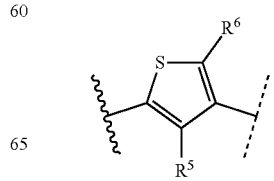

T3

-continued

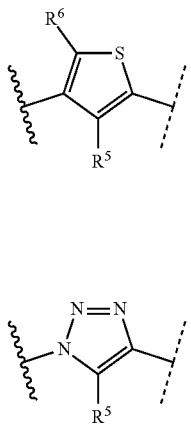

T4

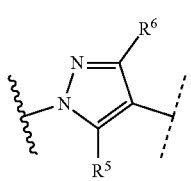

T5 or an agrochemically acceptable salt or N-oxide thereof.

Embodiment 25

A compound or salt according to embodiment 1 of formula (Ia)

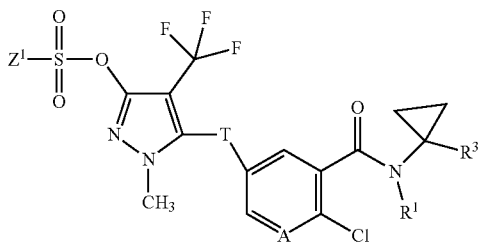

(Ia)

wherein $Z^1$ is —$CF_2CF_3$ and $R^1$ is selected from H, methyl and ethyl; or $Z^1$ is —$CF_2CF_2CF_2CF_3$ and $R^1$ is selected from methyl and ethyl; or $Z^1$ is —$CF(CF_3)(CF_3)$ and $R^1$ is selected from H, methyl and ethyl; or $Z^1$ is —$CF_2CF_2Cl$ and $R^1$ is selected from H, methyl and ethyl;

A is selected from C—H and N;

$R^3$ is selected from H and CN;

T is selected from

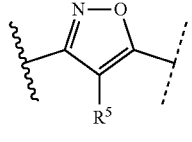

T6 or an agrochemically acceptable salt or N-oxide thereof.

Embodiment 26

A compound or salt according to embodiment 1 of formula (Ia)

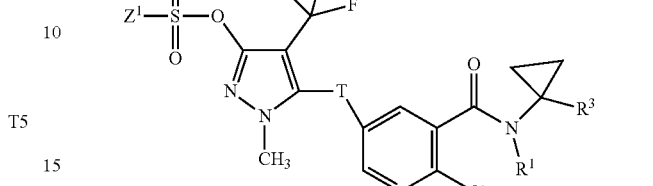

(Ia)

wherein $Z^1$ is —$CF_2CF_3$ and $R^1$ is selected from H, methyl and ethyl; or $Z^1$ is —$CF_2CF_2CF_2CF_3$ and $R^1$ is selected from H, methyl and ethyl; or $Z^1$ is —$CF(CF_3)(CF_3)$ and $R^1$ is selected from H, methyl and ethyl; or $Z^1$ is —$CF_2CF_2Cl$ and $R^1$ is selected from H, methyl and ethyl;

A is selected from C—H and N;

$R^3$ is selected from H and CN;

T is selected from

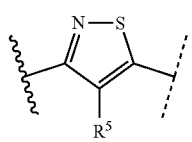

T1

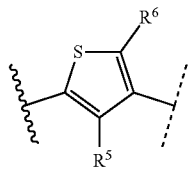

T2

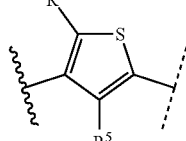

T3

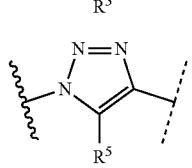

T4

T5 or an agrochemically acceptable salt or N-oxide thereof.

Embodiment 27

A compound or salt according to embodiment 1 of formula (Ia)

(Ia)

wherein $Z^1$ is —$CF_2CF_2CF_2CF_3$ and $R^1$ is selected from methyl and ethyl; or $Z^1$ is —$CF(CF_3)(CF_3)$ and $R^1$ is selected from H, methyl and ethyl;

A is selected from C—H and N;

$R^3$ is selected from H and CN;

T is selected from

T6 or an agrochemically acceptable salt or N-oxide thereof.

Embodiment 28

A compound or salt according to embodiment 1 of formula (Ia)

(Ia)

wherein $Z^1$ is —$CF_2CF_2CF_2CF_3$ and $R^1$ is selected from H, methyl and ethyl; or $Z^1$ is —$CF(CF_3)(CF_3)$ and $R^1$ is selected from H, methyl and ethyl;

A is selected from C—H and N;

$R^3$ is selected from H and CN;

T is selected from

T1

T2

T3

T4

T5 or an agrochemically acceptable salt or N-oxide thereof.

Embodiment 29

A compound or salt according to embodiment 1 of formula (Ia)

(Ia)

wherein $Z^1$ is —$CF(CF_3)(CF_3)$;

$R^1$ is selected from H, $C_1$-$C_6$-alkyl, $C_2$-$C_6$ alkenyl, $C_2$-$C_6$ alkynyl, $C_1$-$C_6$-alkylcarbonyl and $C_1$-$C_6$-alkoxycarbonyl, wherein each of $C_1$-$C_6$-alkyl, $C_2$-$C_6$ alkenyl, $C_2$-$C_6$ alkynyl, $C_1$-$C_6$-alkylcarbonyl and $C_1$-$C_6$-alkoxycarbonyl is unsubstituted or substituted with 1 to 10 substituents independently selected from halogen, cyano, $C_1$-$C_6$-alkoxy and $C_1$-$C_6$-alkoxycarbonyl;

A is selected from C—H and N;

$R^3$ is selected from H and CN;

T is selected from

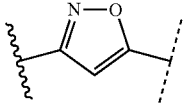

or an agrochemically acceptable salt or N-oxide thereof.

Embodiment 29.1

A compound or salt according to embodiment 1 of formula (Ia)

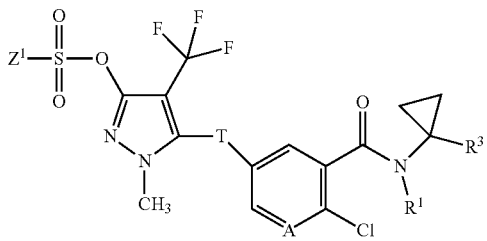

wherein
$Z^1$ is —CF(CF$_3$)(CF$_3$);
$R^1$ is selected from H, methyl, ethyl, propyl, 2-methyl-propyl, 1-methyl-ethyl, —C(=O)—H, —C(=O)—CH$_3$, —CH$_2$—O-ethyl, —CH$_2$—O-methyl, —CH$_2$—O—CH(CH$_3$)(CH$_3$), —CH$_2$—O—(CH$_3$)(CH$_3$)(CH$_3$), —CH$_2$—CH$_2$—O-methyl, —CH$_2$—CH$_2$—O-ethyl, —CH$_2$—CH$_2$—CH$_2$—O-ethyl, —CH$_2$—C≡CH, —C(=O)—O-methyl, —C(=O)—O-ethyl, —C(=O)—O—CH(CH$_3$)(CH$_3$), —C(=O)—CH(CH$_3$)(CH$_3$), —C(=O)—(CH$_3$)(CH$_3$)(CH$_3$), —CH$_2$—CN, —CH(methyl)-CN, —CH(ethyl)-CN, —C(=O)-ethyl, —CF=CF—CF$_3$ and —C(=O)—CH$_2$—O-methyl;
A is selected from C—H and N;
$R^3$ is selected from H and CN;
T is selected from

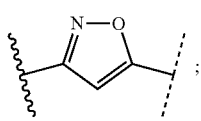

or an agrochemically acceptable salt or N-oxide thereof.

Embodiment 29.2

A compound or salt according to embodiment 1 of formula (Ia)

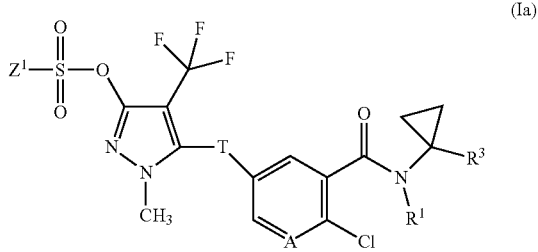

wherein
$Z^1$ is —CF$_2$CF$_2$CF$_2$CF$_3$ and $R^1$ is selected from H, methyl and ethyl; or
$Z^1$ is —CF(CF$_3$)(CF$_3$) and $R^1$ is selected from H, methyl and ethyl;
A is selected from C—H and N;
$R^3$ is selected from H and CN;
T is selected from

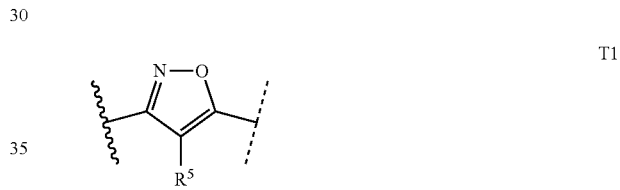

or an agrochemically acceptable salt or N-oxide thereof.

Embodiment 30

A compound or salt according to embodiment 1 of formula (Ia)

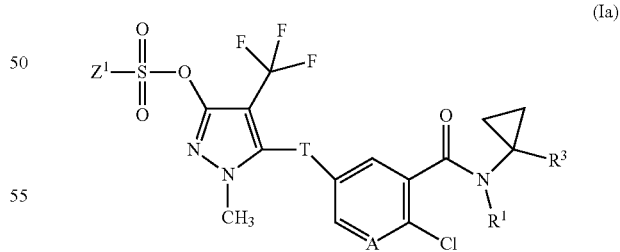

wherein
$Z^1$ is —CF$_2$CF$_2$CF$_2$CF$_3$ and $R^1$ is selected from H, methyl and ethyl; or
$Z^1$ is —CF(CF$_3$)(CF$_3$) and $R^1$ is selected from H, methyl and ethyl;
A is selected from C—H and N;
$R^3$ is selected from H and CN;

T is selected from

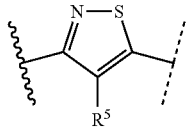

or an agrochemically acceptable salt or N-oxide thereof.

Embodiment 30.1

A compound or salt according to embodiment 1 of formula (Ia)

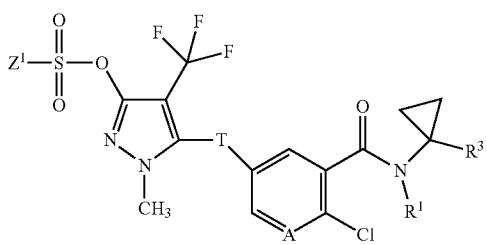

wherein
$Z^1$ is —CF($CF_3$)($CF_3$);
$R^1$ is selected from H, methyl, ethyl, propyl, 2-methylpropyl, 1-methyl-ethyl, —C(=O)—H, —C(=O)—$CH_3$, —$CH_2$—O-ethyl, —$CH_2$—O-methyl, —$CH_2$—O—CH($CH_3$)($CH_3$), —$CH_2$—O—($CH_3$)($CH_3$)($CH_3$), —$CH_2$—$CH_2$—O-methyl, —$CH_2$—$CH_2$—O-ethyl, —$CH_2$—$CH_2$—$CH_2$—O-ethyl, —$CH_2$—C≡CH, —C(=O)—O-methyl, —C(=O)—O-ethyl, —C(=O)—O—CH($CH_3$)($CH_3$), —C(=O)—CH($CH_3$)($CH_3$), —C(=O)—($CH_3$)($CH_3$)($CH_3$), —$CH_2$—CN, —CH(methyl)-CN, —CH(ethyl)-CN, —C(=O)-ethyl, —CF=CF—$CF_3$ and —C(=O)—$CH_2$—O-methyl;
A is selected from C—H and N;
$R^3$ is selected from H and CN;
T is

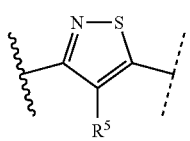

or an agrochemically acceptable salt or N-oxide thereof.

Embodiment 31

A compound or salt according to embodiment 1 of formula (Ia)

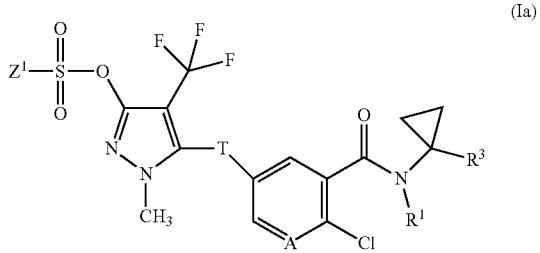

wherein
$Z^1$ is —$CF_2CF_2CF_2CF_3$ and $R^1$ is selected from H, methyl and ethyl; or
$Z^1$ is —CF($CF_3$)($CF_3$) and $R^1$ is selected from H, methyl and ethyl;
A is selected from C—H and N;
$R^3$ is selected from H and CN;
T is selected from

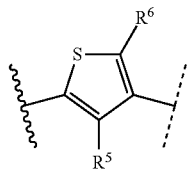

or an agrochemically acceptable salt or N-oxide thereof.

Embodiment 31.1

A compound or salt according to embodiment 1 of formula (Ia)

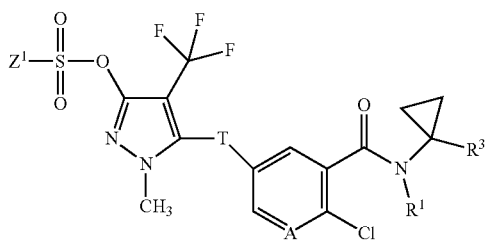

wherein
$Z^1$ is —CF($CF_3$)($CF_3$);
$R^1$ is selected from H, methyl, ethyl, propyl, 2-methylpropyl, 1-methyl-ethyl, —C(=O)—H, —C(=O)—$CH_3$, —$CH_2$—O-ethyl, —$CH_2$—O-methyl, —$CH_2$—O—CH($CH_3$)($CH_3$), —$CH_2$—O—($CH_3$)($CH_3$)($CH_3$), —$CH_2$—$CH_2$—O-methyl, —$CH_2$—$CH_2$—O-ethyl, —$CH_2$—$CH_2$—O-ethyl, —$CH_2$—C≡CH, —C(=O)—O-methyl, —C(=O)—O-ethyl, —C(=O)—O—CH($CH_3$)($CH_3$), —C(=O)—CH($CH_3$)($CH_3$), —C(=O)—($CH_3$)($CH_3$)

(CH$_3$), —CH$_2$—CN, —CH(methyl)-CN, —CH(ethyl)-CN, —C(=O)-ethyl, —CF=CF—CF$_3$ and —C(=O)—CH$_2$—O-methyl;

A is selected from C—H and N;

R$^3$ is selected from H and CN;

T is selected from

T3 or an agrochemically acceptable salt or N-oxide thereof.

Embodiment 32

A compound or salt according to embodiment 1 of formula (Ia)

(Ia)

wherein

Z$^1$ is —CF$_2$CF$_2$CF$_2$CF$_3$ and R$^1$ is selected from H, methyl and ethyl; or Z$^1$ is —CF(CF$_3$)(CF$_3$) and R$^1$ is selected from H, methyl and ethyl;

A is selected from C—H and N;

R$^3$ is selected from H and CN;

T is selected from

T4 or an agrochemically acceptable salt or N-oxide thereof.

Embodiment 32.1

A compound or salt according to embodiment 1 of formula (Ia)

(Ia)

wherein

Z$^1$ is —CF(CF$_3$)(CF$_3$);

R$^1$ is selected from H, methyl, ethyl, propyl, 2-methyl-propyl, 1-methyl-ethyl, —C(=O)—H, —C(=O)—CH$_3$, —CH$_2$—O-ethyl, —CH$_2$—O-methyl, —CH$_2$—O—CH(CH$_3$)(CH$_3$), —CH$_2$—O—(CH$_3$)(CH$_3$)(CH$_3$), —CH$_2$—CH$_2$—O-methyl, —CH$_2$—CH$_2$—O-ethyl, —CH$_2$—CH$_2$—CH$_2$—O-ethyl, —CH$_2$—C≡CH, —C(=O)—O-methyl, —C(=O)—O-ethyl, —C(=O)—O—CH(CH$_3$)(CH$_3$), —C(=O)—CH(CH$_3$)(CH$_3$), —C(=O)—(CH$_3$)(CH$_3$)(CH$_3$), —CH$_2$—CN, —CH(methyl)-CN, —CH(ethyl)-CN, —C(=O)-ethyl, —CF=CF—CF$_3$ and —C(=O)—CH$_2$—O-methyl;

A is selected from C—H and N;

R$^3$ is selected from H and CN;

T is selected from

T4 or an agrochemically acceptable salt or N-oxide thereof.

Embodiment 33

A compound or salt according to embodiment 1 of formula (Ia)

(Ia)

wherein

Z$^1$ is —CF$_2$CF$_2$CF$_2$CF$_3$ and R$^1$ is selected from H, methyl and ethyl; or $Z^1$ is —CF(CF$_3$)(CF$_3$) and $R^1$ is selected from H, methyl and ethyl;

A is selected from C—H and N;

$R^3$ is selected from H and CN;

T is selected from

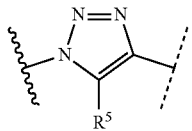

or an agrochemically acceptable salt or N-oxide thereof.

Embodiment 33.1

A compound or salt according to embodiment 1 of formula (Ia)

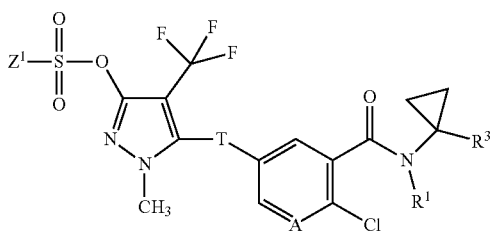

(Ia)

wherein $Z^1$ is —CF(CF$_3$)(CF$_3$);

$R^1$ is selected from H, methyl, ethyl, propyl, 2-methyl-propyl, 1-methyl-ethyl, —C(=O)—H, —C(=O)—CH$_3$, —CH$_2$—O-ethyl, —CH$_2$—O-methyl, —CH$_2$—O—CH(CH$_3$)(CH$_3$), —CH$_2$—O—(CH$_3$)(CH$_3$)(CH$_3$), —CH$_2$—CH$_2$—O-methyl, —CH$_2$—CH$_2$—O-ethyl, —CH$_2$—CH$_2$—CH$_2$—O-ethyl, —CH$_2$—C≡CH, —C(=O)—O-methyl, —C(=O)—O-ethyl, —C(=O)—O—CH(CH$_3$)(CH$_3$), —C(=O)—CH(CH$_3$)(CH$_3$), —C(=O)—(CH$_3$)(CH$_3$)(CH$_3$), —CH$_2$—CN, —CH(methyl)-CN, —CH(ethyl)-CN, —C(=O)-ethyl, —CF=CF—CF$_3$ and —C(=O)—CH$_2$—O-methyl;

A is selected from C—H and N;

$R^3$ is selected from H and CN;

T is selected from

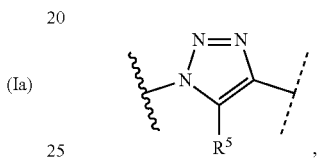

or an agrochemically acceptable salt or N-oxide thereof.

Embodiment 34

A compound or salt according to embodiment 1 selected from

| Ex. No. | Structure | |
|---|---|---|
| 1 | ![structure] | [5-[4-[4-chloro-3-[(1-cyanocyclopropyl)carbamoyl]phenyl]pyrazol-1-yl]-1-methyl-4-(trifluoromethyl)pyrazol-3-yl] 1,1,2,2,2-pentafluoroethanesulfonate |
| 2 | ![structure] | [5-[4-[4-chloro-3-[(1-cyanocyclopropyl)carbamoyl]phenyl]pyrazol-1-yl]-1-methyl-4-(trifluoromethyl)pyrazol-3-yl] 1,1,1,2,3,3,3-heptafluoropropane-2-sulfonate |

-continued

| Ex. No. | Structure | |
|---|---|---|
| 3 | 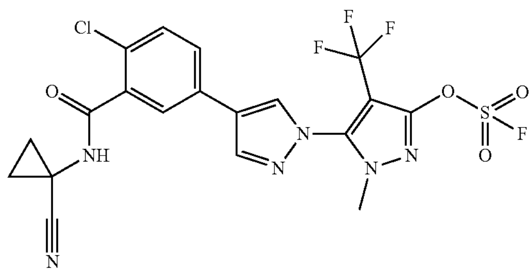 [SMILES: Cn1nc(OS(=O)(=O)F)c(C(F)(F)F)c1-n1cc(-c2ccc(Cl)c(C(=O)NC3(C#N)CC3)c2)cn1] | 5-[4-[4-chloro-3-[(1-cyanocyclopropyl)carbamoyl]phenyl]pyrazol-1-yl]-3-fluorosulfonyloxy-1-methyl-4-(trifluoromethyl)pyrazole |
| 4 | 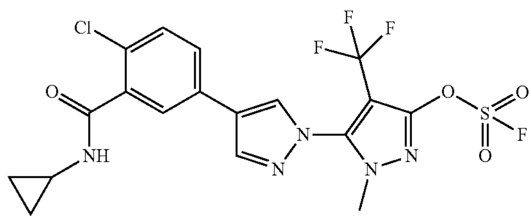 [SMILES: Cn1nc(OS(=O)(=O)F)c(C(F)(F)F)c1-n1cc(-c2ccc(Cl)c(C(=O)NC3CC3)c2)cn1] | 5-[4-[4-chloro-3-(cyclopropylcarbamoyl)phenyl]pyrazol-1-yl]-3-fluorosulfonyloxy-1-methyl-4-(trifluoromethyl)pyrazole |
| 5 | 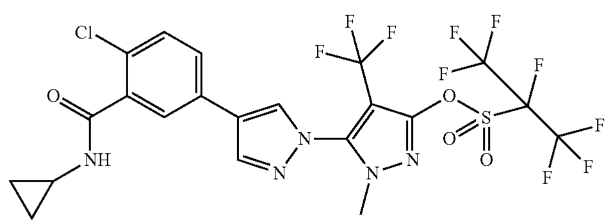 [SMILES: Cn1nc(OS(=O)(=O)C(F)(C(F)(F)F)C(F)(F)F)c(C(F)(F)F)c1-n1cc(-c2ccc(Cl)c(C(=O)NC3CC3)c2)cn1] | [5-[4-[4-chloro-3-(cyclopropylcarbamoyl)phenyl]pyrazol-1-yl]-1-methyl-4-(trifluoromethyl)pyrazol-3-yl] 1,1,1,2,3,3,3-heptafluoropropane-2-sulfonate |
| 6 | 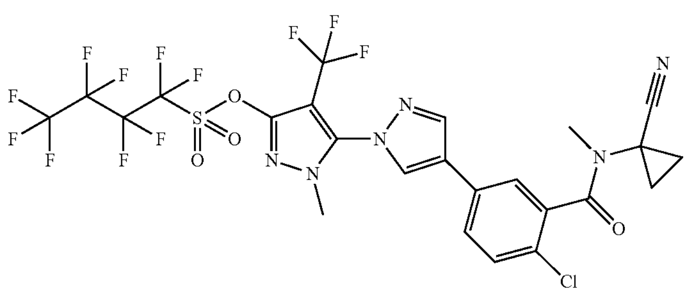 [SMILES: CN(C(=O)c1cc(-c2cnn(-c3c(C(F)(F)F)c(OS(=O)(=O)C(F)(F)C(F)(F)C(F)(F)C(F)(F)F)nn3C)c2)ccc1Cl)C1(C#N)CC1] | [5-[4-[4-chloro-3-[(1-cyanocyclopropyl)-methyl-carbamoyl]phenyl]pyrazol-1-yl]-1-methyl-4-(trifluoromethyl)pyrazol-3-yl] 1,1,2,2,3,3,4,4,4-nonafluorobutane-1-sulfonate |
| 7 | 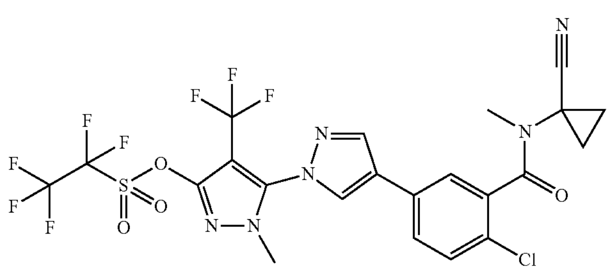 [SMILES: CN(C(=O)c1cc(-c2cnn(-c3c(C(F)(F)F)c(OS(=O)(=O)C(F)(F)C(F)(F)F)nn3C)c2)ccc1Cl)C1(C#N)CC1] | [5-[4-[4-chloro-3-[(1-cyanocyclopropyl)-methyl-carbamoyl]phenyl]pyrazol-1-yl]-1-methyl-4-(trifluoromethyl)pyrazol-3-yl] 1,1,2,2,2-pentafluoroethanesulfonate |
| 8 | 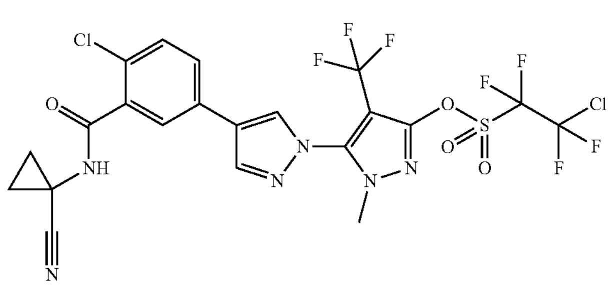 [SMILES: Cn1nc(OS(=O)(=O)C(F)(F)C(F)(F)Cl)c(C(F)(F)F)c1-n1cc(-c2ccc(Cl)c(C(=O)NC3(C#N)CC3)c2)cn1] | [5-[4-[4-chloro-3-[(1-cyanocyclopropyl)carbamoyl]phenyl]pyrazol-1-yl]-1-methyl-4-(trifluoromethyl)pyrazol-3-yl] 2-chloro-1,1,2,2-tetrafluoro-ethanesulfonate |

-continued

| Ex. No. | Structure | |
|---|---|---|
| 9 | 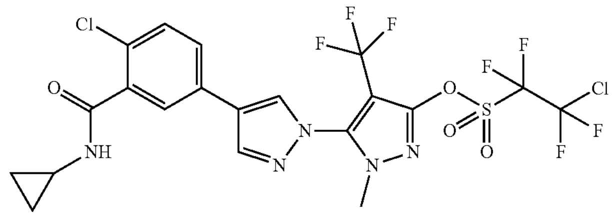 [SMILES: Cn1nc(OS(=O)(=O)C(F)(F)C(F)(F)Cl)c(C(F)(F)F)c1-n1cc(-c2ccc(Cl)c(C(=O)NC3CC3)c2)cn1] | [5-[4-[4-chloro-3-(cyclopropylcarbamoyl)phenyl]pyrazol-1-yl]-1-methyl-4-(trifluoromethyl)pyrazol-3-yl] 2-chloro-1,1,2,2-tetrafluoro-ethanesulfonate |
| 10 | 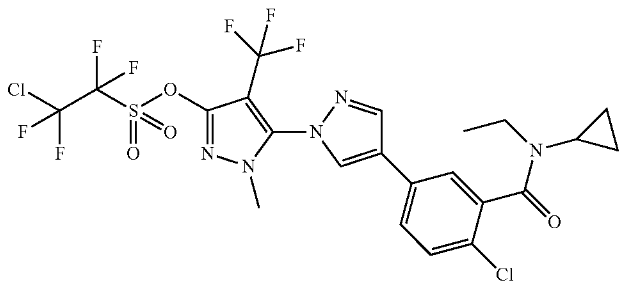 [SMILES: CCN(C(=O)c1cc(-c2cnn(-c3c(C(F)(F)F)c(OS(=O)(=O)C(F)(F)C(F)(F)Cl)nn3C)c2)ccc1Cl)C1CC1] | [5-[4-[4-chloro-3-[cyclopropyl(ethyl)carbamoyl]phenyl]pyrazol-1-yl]-1-methyl-4-(trifluoromethyl)pyrazol-3-yl] 2-chloro-1,1,2,2-tetrafluoro-ethanesulfonate |
| 11 | 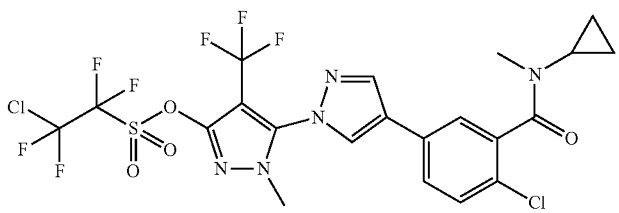 [SMILES: CN(C(=O)c1cc(-c2cnn(-c3c(C(F)(F)F)c(OS(=O)(=O)C(F)(F)C(F)(F)Cl)nn3C)c2)ccc1Cl)C1CC1] | [5-[4-[4-chloro-3-[cyclopropyl(methyl)carbamoyl]phenyl]pyrazol-1-yl]-1-methyl-4-(trifluoromethyl)pyrazol-3-yl] 2-chloro-1,1,2,2-tetrafluoro-ethanesulfonate |
| 12 | 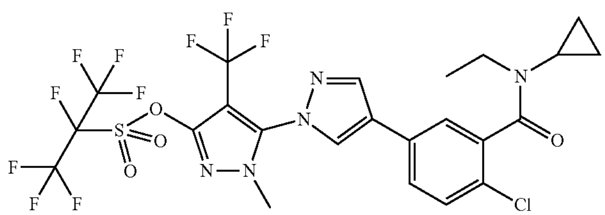 [SMILES: CCN(C(=O)c1cc(-c2cnn(-c3c(C(F)(F)F)c(OS(=O)(=O)C(F)(C(F)(F)F)C(F)(F)F)nn3C)c2)ccc1Cl)C1CC1] | [5-[4-[4-chloro-3-[cyclopropyl(ethyl)carbamoyl]phenyl]pyrazol-1-yl]-1-methyl-4-(trifluoromethyl)pyrazol-3-yl] 1,1,1,2,3,3,3-heptafluoropropane-2-sulfonate |
| 13 | 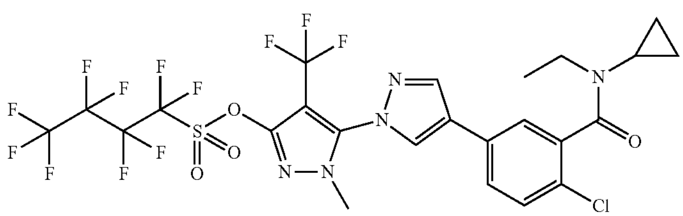 [SMILES: CCN(C(=O)c1cc(-c2cnn(-c3c(C(F)(F)F)c(OS(=O)(=O)C(F)(F)C(F)(F)C(F)(F)C(F)(F)F)nn3C)c2)ccc1Cl)C1CC1] | [5-[4-[4-chloro-3-[cyclopropyl(ethyl)carbamoyl]phenyl]pyrazol-1-yl]-1-methyl-4-(trifluoromethyl)pyrazol-3-yl] 1,1,2,2,3,3,4,4,4-nonafluorobutane-1-sulfonate |
| 14 | 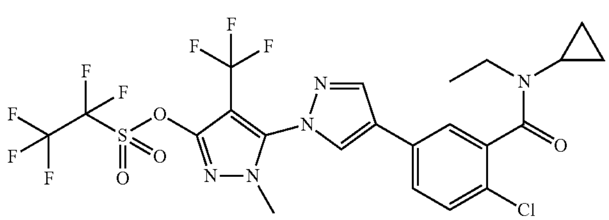 [SMILES: CCN(C(=O)c1cc(-c2cnn(-c3c(C(F)(F)F)c(OS(=O)(=O)C(F)(F)C(F)(F)F)nn3C)c2)ccc1Cl)C1CC1] | [5-[4-[4-chloro-3-[cyclopropyl(ethyl)carbamoyl]phenyl]pyrazol-1-yl]-1-methyl-4-(trifluoromethyl)pyrazol-3-yl] 1,1,2,2,2-pentafluoroethanesulfonate |
| 15 | 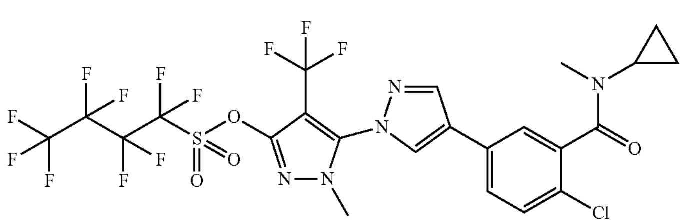 [SMILES: CN(C(=O)c1cc(-c2cnn(-c3c(C(F)(F)F)c(OS(=O)(=O)C(F)(F)C(F)(F)C(F)(F)C(F)(F)F)nn3C)c2)ccc1Cl)C1CC1] | [5-[4-[4-chloro-3-[cyclopropyl(methyl)carbamoyl]phenyl]pyrazol-1-yl]-1-methyl-4-(trifluoromethyl)pyrazol-3-yl] 1,1,2,2,3,3,4,4,4-nonafluorobutane-1-sulfonate |

| Ex. No. | Structure | |
|---|---|---|
| 16 | 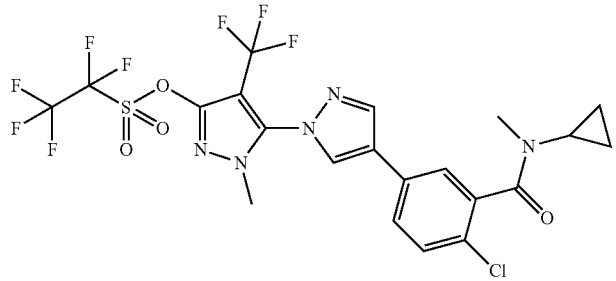 [SMILES: CN(C(=O)c1cc(-c2cnn(-c3c(C(F)(F)F)c(OS(=O)(=O)C(F)(F)C(F)(F)F)nn3C)c2)ccc1Cl)C1CC1] | [5-[4-[4-chloro-3-[cyclopropyl(methyl)carbamoyl]phenyl]pyrazol-1-yl]-1-methyl-4-(trifluoromethyl)pyrazol-3-yl] 1,1,2,2,2-pentafluoroethanesulfonate |
| 17 | 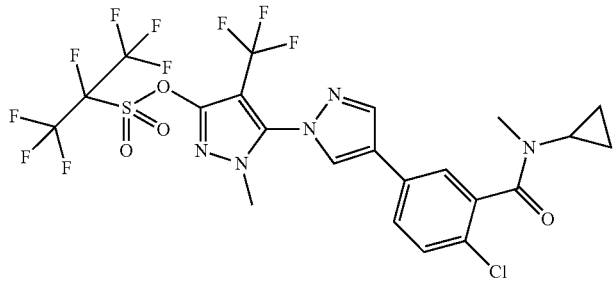 [SMILES: CN(C(=O)c1cc(-c2cnn(-c3c(C(F)(F)F)c(OS(=O)(=O)C(F)(C(F)(F)F)C(F)(F)F)nn3C)c2)ccc1Cl)C1CC1] | [5-[4-[4-chloro-3-[cyclopropyl(methyl)carbamoyl]phenyl]pyrazol-1-yl]-1-methyl-4-(trifluoromethyl)pyrazol-3-yl] 1,1,1,2,3,3,3-heptafluoropropane-2-sulfonate |
| 18 | 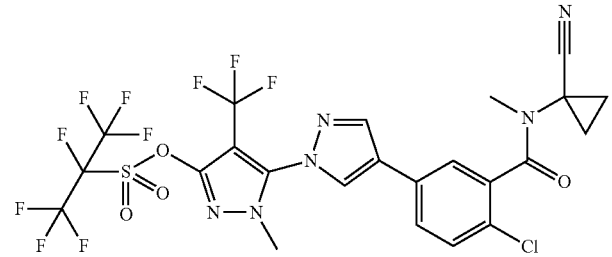 [SMILES: CN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-methyl-carbamoyl]phenyl]pyrazol-1-yl]-1-methyl-4-(trifluoromethyl)pyrazol-3-yl] 1,1,1,2,3,3,3-heptafluoropropane-2-sulfonate |
| 19 | 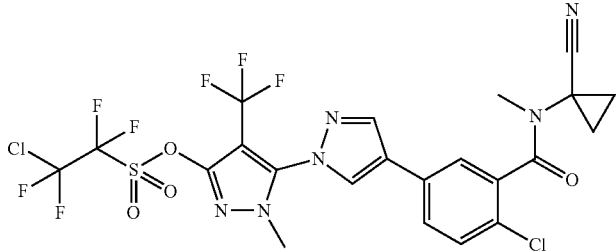 [SMILES: CN(C(=O)c1cc(-c2cnn(-c3c(C(F)(F)F)c(OS(=O)(=O)C(F)(F)C(F)(F)Cl)nn3C)c2)ccc1Cl)C1(C#N)CC1] | [5-[4-[4-chloro-3-[(1-cyanocyclopropyl)-methyl-carbamoyl]phenyl]pyrazol-1-yl]-1-methyl-4-(trifluoromethyl)pyrazol-3-yl] 2-chloro-1,1,2,2-tetrafluoro-ethanesulfonate |
| 20 | 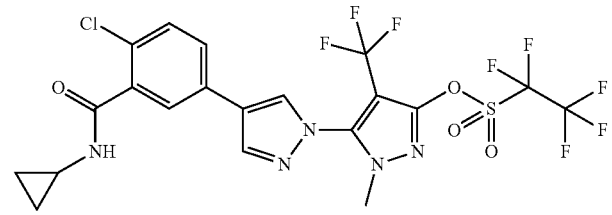 [SMILES: Cn1nc(OS(=O)(=O)C(F)(F)C(F)(F)F)c(C(F)(F)F)c1-n1cc(-c2ccc(Cl)c(C(=O)NC3CC3)c2)cn1] | [5-[4-[4-chloro-3-(cyclopropylcarbamoyl)phenyl]pyrazol-1-yl]-1-methyl-4-(trifluoromethyl)pyrazol-3-yl] 1,1,2,2,2-pentafluoroethanesulfonate |

-continued

| Ex. No. | Structure | |
|---|---|---|
| 21 | 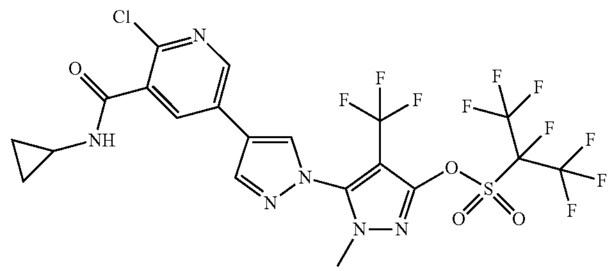 [SMILES: Cn1nc(OS(=O)(=O)C(F)(C(F)(F)F)C(F)(F)F)c(C(F)(F)F)c1-n1cc(-c2cnc(Cl)c(C(=O)NC3CC3)c2)cn1] | [5-[4-[6-chloro-5-(cyclopropylcarbamoyl)-3-pyridyl]pyrazol-1-yl]-1-methyl-4-(trifluoromethyl)pyrazol-3-yl] 1,1,1,2,3,3,3-heptafluoropropane-2-sulfonate |
| 22 | 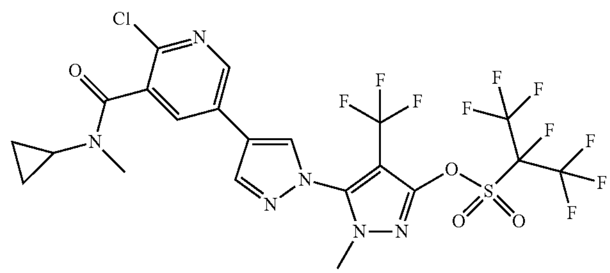 [SMILES: CN(C(=O)c1cc(-c2cnn(-c3c(C(F)(F)F)c(OS(=O)(=O)C(F)(C(F)(F)F)C(F)(F)F)nn3C)c2)cnc1Cl)C1CC1] | [5-[4-[6-chloro-5-[cyclopropyl(methyl)carbamoyl]-3-pyridyl]pyrazol-1-yl]-1-methyl-4-(trifluoromethyl)pyrazol-3-yl] 1,1,1,2,3,3,3-heptafluoropropane-2-sulfonate |
| 23 | 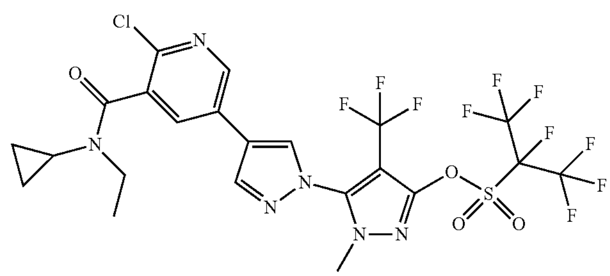 [SMILES: CCN(C(=O)c1cc(-c2cnn(-c3c(C(F)(F)F)c(OS(=O)(=O)C(F)(C(F)(F)F)C(F)(F)F)nn3C)c2)cnc1Cl)C1CC1] | [5-[4-[6-chloro-5-[cyclopropyl(ethyl)carbamoyl]-3-pyridyl]pyrazol-1-yl]-1-methyl-4-(trifluoromethyl)pyrazol-3-yl] 1,1,1,2,3,3,3-heptafluoropropane-2-sulfonate |
| 24 | 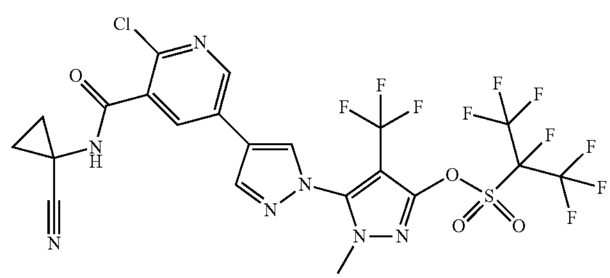 [SMILES: Cn1nc(OS(=O)(=O)C(F)(C(F)(F)F)C(F)(F)F)c(C(F)(F)F)c1-n1cc(-c2cnc(Cl)c(C(=O)NC3(C#N)CC3)c2)cn1] | [5-[4-[6-chloro-5-[(1-cyanocyclopropyl)carbamoyl]-3-pyridyl]pyrazol-1-yl]-1-methyl-4-(trifluoromethyl)pyrazol-3-yl] 1,1,1,2,3,3,3-heptafluoropropane-2-sulfonate |
| 25 | 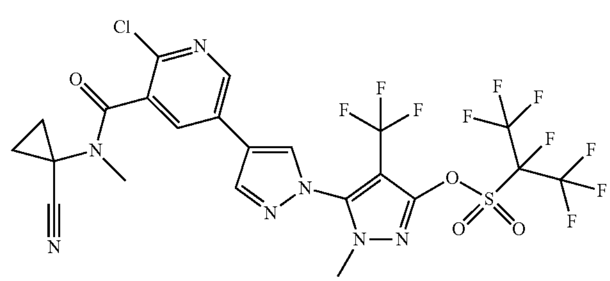 [SMILES: CN(C(=O)c1cc(-c2cnn(-c3c(C(F)(F)F)c(OS(=O)(=O)C(F)(C(F)(F)F)C(F)(F)F)nn3C)c2)cnc1Cl)C1(C#N)CC1] | [5-[4-[6-chloro-5-[(1-cyanocyclopropyl)-methyl-carbamoyl]-3-pyridyl]pyrazol-1-yl]-1-methyl-4-(trifluoromethyl)pyrazol-3-yl] 1,1,1,2,3,3,3-heptafluoropropane-2-sulfonate |

| Ex. No. | Structure | |
|---|---|---|
| 26 | 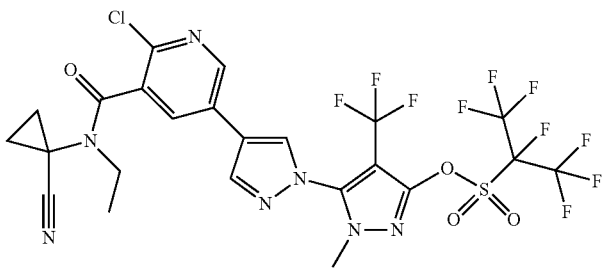 [SMILES: CCN(C(=O)c1cc(-c2cnn(-c3c(C(F)(F)F)c(OS(=O)(=O)C(F)(C(F)(F)F)C(F)(F)F)nn3C)c2)cnc1Cl)C1(C#N)CC1] | [5-[4-[6-chloro-5-[(1-cyanocyclopropyl)-ethyl-carbamoyl]-3-pyridyl]pyrazol-1-yl]-1-methyl-4-(trifluoromethyl)pyrazol-3-yl] 1,1,1,2,3,3,3-heptafluoropropane-2-sulfonate |
| 27 | 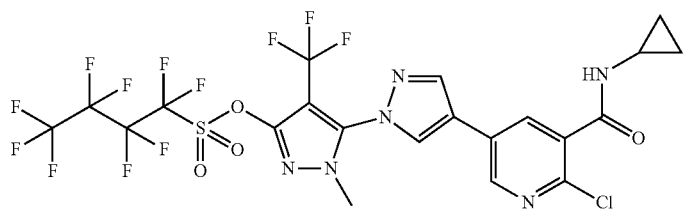 [SMILES: Cn1nc(OS(=O)(=O)C(F)(F)C(F)(F)C(F)(F)C(F)(F)F)c(C(F)(F)F)c1-n1cc(-c2cnc(Cl)c(C(=O)NC3CC3)c2)cn1] | [5-[4-[6-chloro-5-(cyclopropylcarbamoyl)-3-pyridyl]pyrazol-1-yl]-1-methyl-4-(trifluoromethyl)pyrazol-3-yl] 1,1,2,2,3,3,4,4,4-nonafluorobutane-1-sulfonate |
| 28 | 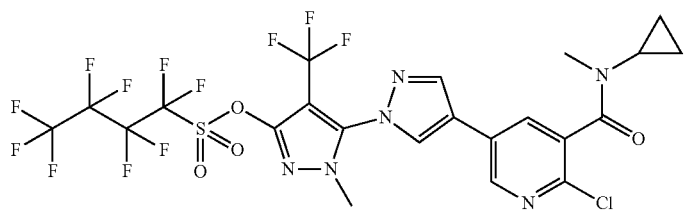 [SMILES: CN(C(=O)c1cc(-c2cnn(-c3c(C(F)(F)F)c(OS(=O)(=O)C(F)(F)C(F)(F)C(F)(F)C(F)(F)F)nn3C)c2)cnc1Cl)C1CC1] | [5-[4-[6-chloro-5-[cyclopropyl(methyl)carbamoyl]-3-pyridyl]pyrazol-1-yl]-1-methyl-4-(trifluoromethyl)pyrazol-3-yl] 1,1,2,2,3,3,4,4,4-nonafluorobutane-1-sulfonate |
| 29 | 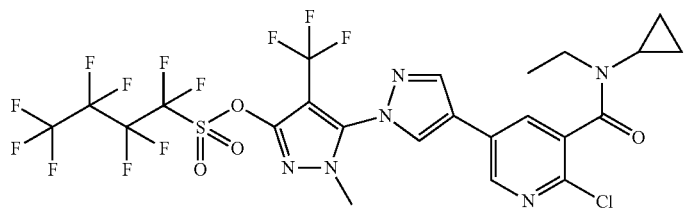 | [5-[4-[6-chloro-5-[cyclopropyl(ethyl)carbamoyl]-3-pyridyl]pyrazol-1-yl]-1-methyl-4-(trifluoromethyl)pyrazol-3-yl] 1,1,2,2,3,3,4,4,4-nonafluorobutane-1-sulfonate |
| 30 | 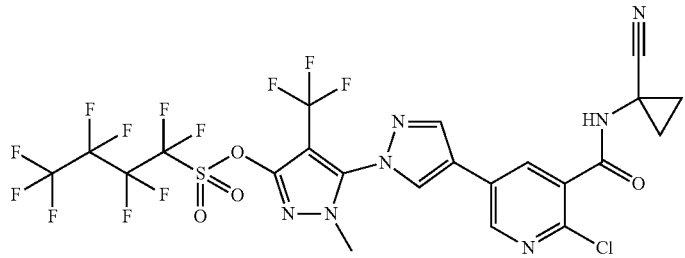 [SMILES: Cn1nc(OS(=O)(=O)C(F)(F)C(F)(F)C(F)(F)C(F)(F)F)c(C(F)(F)F)c1-n1cc(-c2cnc(Cl)c(C(=O)NC3(C#N)CC3)c2)cn1] | [5-[4-[6-chloro-5-[(1-cyanocyclopropyl)carbamoyl]-3-pyridyl]pyrazol-1-yl]-1-methyl-4-(trifluoromethyl)pyrazol-3-yl] 1,1,2,2,3,3,4,4,4-nonafluorobutane-1-sulfonate |
| 31 | 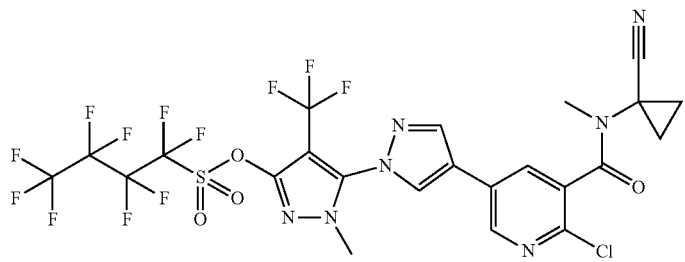 [SMILES: CN(C(=O)c1cc(-c2cnn(-c3c(C(F)(F)F)c(OS(=O)(=O)C(F)(F)C(F)(F)C(F)(F)C(F)(F)F)nn3C)c2)cnc1Cl)C1(C#N)CC1] | [5-[4-[6-chloro-5-[(1-cyanocyclopropyl)-methyl-carbamoyl]-3-pyridyl]pyrazol-1-yl]-1-methyl-4-(trifluoromethyl)pyrazol-3-yl] 1,1,2,2,3,3,4,4,4-nonafluorobutane-1-sulfonate |

| Ex. No. | Structure | |
|---|---|---|
| 32 | 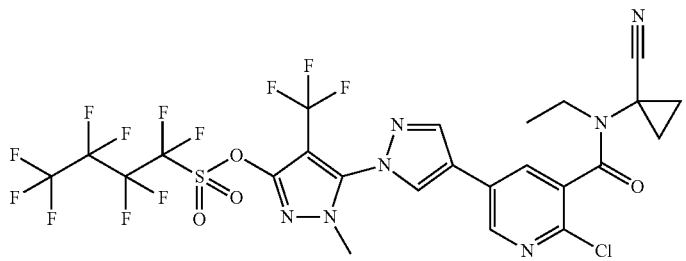 [SMILES: CCN(C(=O)c1cc(-c2cnn(-c3c(C(F)(F)F)c(OS(=O)(=O)C(F)(F)C(F)(F)C(F)(F)C(F)(F)F)nn3C)c2)cnc1Cl)C1(C#N)CC1] | [5-[4-[6-chloro-5-[(1-cyanocyclopropyl)-ethyl-carbamoyl]-3-pyridyl]pyrazol-1-yl]-1-methyl-4-(trifluoromethyl)pyrazol-3-yl] 1,1,2,2,3,3,4,4,4-nonafluorobutane-1-sulfonate |
| 33 | 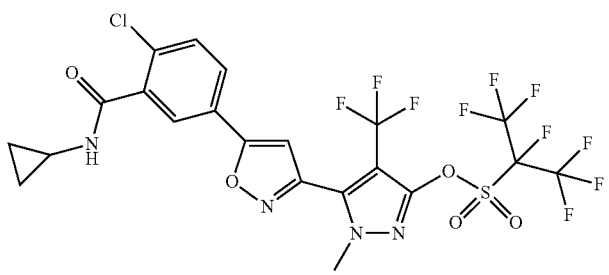 [SMILES: Cn1nc(OS(=O)(=O)C(F)(C(F)(F)F)C(F)(F)F)c(C(F)(F)F)c1-c1cc(-c2ccc(Cl)c(C(=O)NC3CC3)c2)on1] | [5-[5-[4-chloro-3-(cyclopropylcarbamoyl)phenyl] isoxazol-3-yl]-1-methyl-4-(trifluoromethyl)pyrazol-3-yl] 1,1,1,2,3,3,3-heptafluoropropane-2-sulfonate |
| 34 | 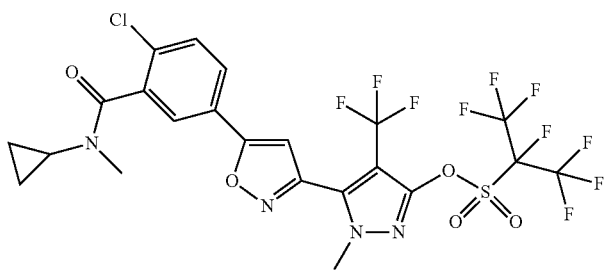 [SMILES: CN(C(=O)c1cc(-c2cc(-c3c(C(F)(F)F)c(OS(=O)(=O)C(F)(C(F)(F)F)C(F)(F)F)nn3C)no2)ccc1Cl)C1CC1] | [5-[5-[4-chloro-3-[cyclopropyl(methyl)carbamoyl]phenyl] isoxazol-3-yl]-1-methyl-4-(trifluoromethyl)pyrazol-3-yl] 1,1,1,2,3,3,3-heptafluoropropane-2-sulfonate |
| 35 | 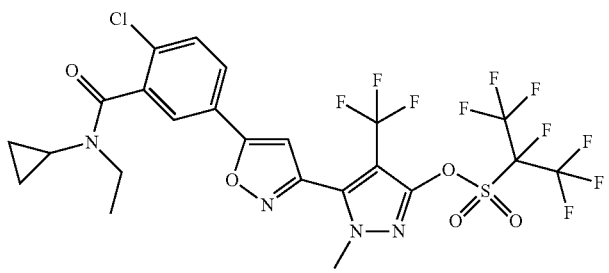 [SMILES: CCN(C(=O)c1cc(-c2cc(-c3c(C(F)(F)F)c(OS(=O)(=O)C(F)(C(F)(F)F)C(F)(F)F)nn3C)no2)ccc1Cl)C1CC1] | [5-[5-[4-chloro-3-[cyclopropyl(ethyl)carbamoyl]phenyl] isoxazol-3-yl]-1-methyl-4-(trifluoromethyl)pyrazol-3-yl] 1,1,1,2,3,3,3-heptafluoropropane-2-sulfonate |
| 36 | 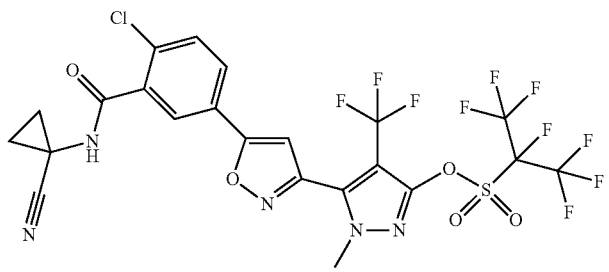 [SMILES: Cn1nc(OS(=O)(=O)C(F)(C(F)(F)F)C(F)(F)F)c(C(F)(F)F)c1-c1cc(-c2ccc(Cl)c(C(=O)NC3(C#N)CC3)c2)on1] | [5-[5-[4-chloro-3-[(1-cyanocyclopropyl)carbamoyl]phenyl]isoxazol-3-yl]-1-methyl-4-(trifluoromethyl)pyrazol-3-yl] 1,1,1,2,3,3,3-heptafluoropropane-2-sulfonate |

-continued

| Ex. No. | Structure | |
|---|---|---|
| 37 | 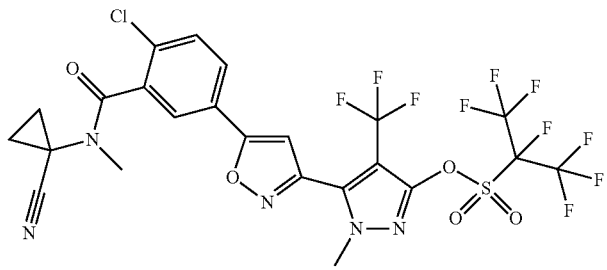 [SMILES: CN(C(=O)c1cc(-c2cc(-c3c(C(F)(F)F)c(OS(=O)(=O)C(F)(C(F)(F)F)C(F)(F)F)nn3C)no2)ccc1Cl)C1(C#N)CC1] | [5-[5-[4-chloro-3-[(1-cyanocyclopropyl)-methyl-carbamoyl]phenyl]isoxazol-3-yl]-1-methyl-4-(trifluoromethyl)pyrazol-3-yl] 1,1,1,2,3,3,3-heptafluoropropane-2-sulfonate |
| 38 | 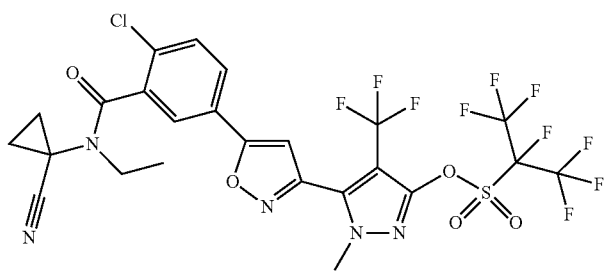 [SMILES: CCN(C(=O)c1cc(-c2cc(-c3c(C(F)(F)F)c(OS(=O)(=O)C(F)(C(F)(F)F)C(F)(F)F)nn3C)no2)ccc1Cl)C1(C#N)CC1] | [5-[5-[4-chloro-3-[(1-cyanocyclopropyl)-ethyl-carbamoyl]phenyl]isoxazol-3-yl]-1-methyl-4-(trifluoromethyl)pyrazol-3-yl] 1,1,1,2,3,3,3-heptafluoropropane-2-sulfonate |
| 39 | 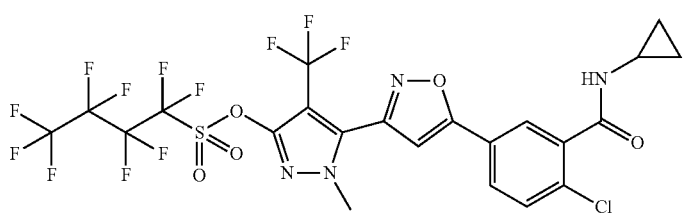 [SMILES: Cn1nc(OS(=O)(=O)C(F)(F)C(F)(F)C(F)(F)C(F)(F)F)c(C(F)(F)F)c1-c1cc(-c2ccc(Cl)c(C(=O)NC3CC3)c2)on1] | [5-[5-[4-chloro-3-(cyclopropylcarbamoyl)phenyl]isoxazol-3-yl]-1-methyl-4-(trifluoromethyl)pyrazol-3-yl] 1,1,2,2,3,3,4,4,4-nonafluorobutane-1-sulfonate |
| 40 | 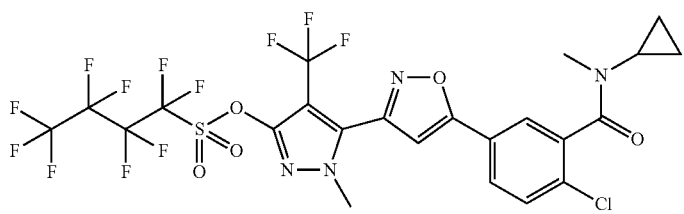 [SMILES: CN(C(=O)c1cc(-c2cc(-c3c(C(F)(F)F)c(OS(=O)(=O)C(F)(F)C(F)(F)C(F)(F)C(F)(F)F)nn3C)no2)ccc1Cl)C1CC1] | [5-[5-[4-chloro-3-[cyclopropyl(methyl)carbamoyl]phenyl]isoxazol-3-yl]-1-methyl-4-(trifluoromethyl)pyrazol-3-yl] 1,1,2,2,3,3,4,4,4-nonafluorobutane-1-sulfonate |
| 41 | 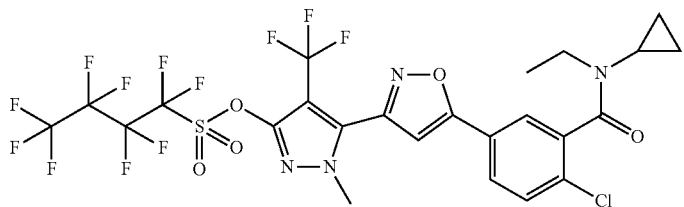 [SMILES: CCN(C(=O)c1cc(-c2cc(-c3c(C(F)(F)F)c(OS(=O)(=O)C(F)(F)C(F)(F)C(F)(F)C(F)(F)F)nn3C)no2)ccc1Cl)C1CC1] | [5-[5-[4-chloro-3-[cyclopropyl(ethyl)carbamoyl]phenyl]isoxazol-3-yl]-1-methyl-4-(trifluoromethyl)pyrazol-3-yl] 1,1,2,2,3,3,4,4,4-nonafluorobutane-1-sulfonate |
| 42 | 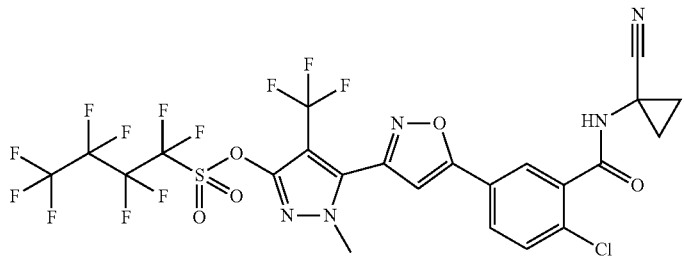 [SMILES: Cn1nc(OS(=O)(=O)C(F)(F)C(F)(F)C(F)(F)C(F)(F)F)c(C(F)(F)F)c1-c1cc(-c2ccc(Cl)c(C(=O)NC3(C#N)CC3)c2)on1] | [5-[5-[4-chloro-3-[(1-cyanocyclopropyl)carbamoyl]phenyl]isoxazol-3-yl]-1-methyl-4-(trifluoromethyl)pyrazol-3-yl] 1,1,2,2,3,3,4,4,4-nonafluorobutane-1-sulfonate |

-continued

| Ex. No. | Structure | |
|---|---|---|
| 43 | 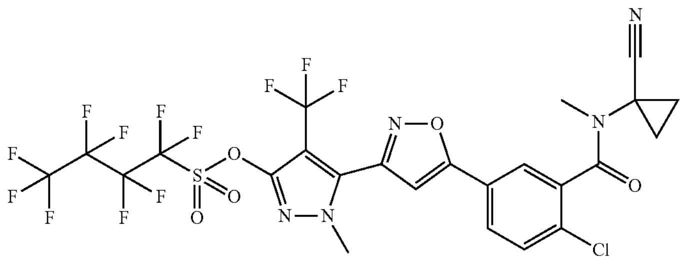 [SMILES: CN(C(=O)c1cc(-c2cc(-c3c(C(F)(F)F)c(OS(=O)(=O)C(F)(F)C(F)(F)C(F)(F)C(F)(F)F)nn3C)no2)ccc1Cl)C1(C#N)CC1] | [5-[5-[4-chloro-3-[(1-cyanocyclopropyl)-methyl-carbamoyl]phenyl]isoxazol-3-yl]-1-methyl-4-(trifluoromethyl)pyrazol-3-yl] 1,1,2,2,3,3,4,4,4-nonafluorobutane-1-sulfonate |
| 44 | 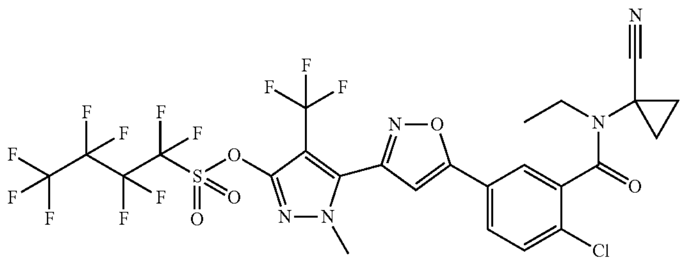 [SMILES: CCN(C(=O)c1cc(-c2cc(-c3c(C(F)(F)F)c(OS(=O)(=O)C(F)(F)C(F)(F)C(F)(F)C(F)(F)F)nn3C)no2)ccc1Cl)C1(C#N)CC1] | [5-[5-[4-chloro-3-[(1-cyanocyclopropyl)-ethyl-carbamoyl]phenyl]isoxazol-3-yl]-1-methyl-4-(trifluoromethyl)pyrazol-3-yl] 1,1,2,2,3,3,4,4,4-nonafluorobutane-1-sulfonate |
| 45 | 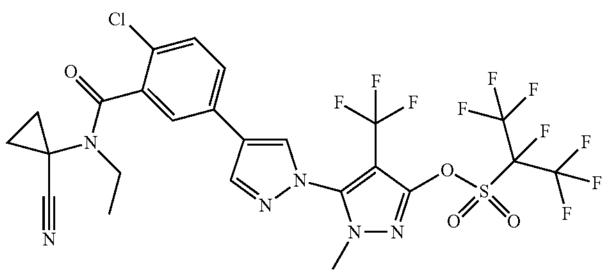 [SMILES: CCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-ethyl-carbamoyl]phenyl]pyrazol-1-yl]-1-methyl-4-(trifluoromethyl)pyrazol-3-yl] 1,1,1,2,3,3,3-heptafluoropropane-2-sulfonate |
| 46 | 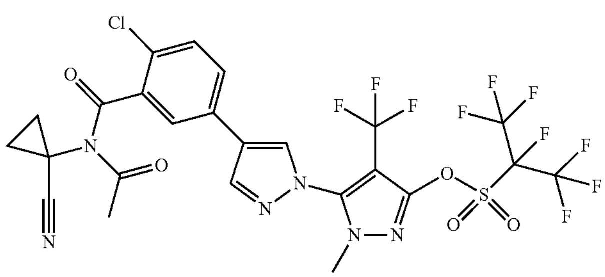 [SMILES: CC(=O)N(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[3-[acetyl-(1-cyanocyclopropyl)carbamoyl]-4-chloro-phenyl]pyrazol-1-yl]-1-methyl-4-(trifluoromethyl)pyrazol-3-yl] 1,1,1,2,3,3,3-heptafluoropropane-2-sulfonate |
| 47 | 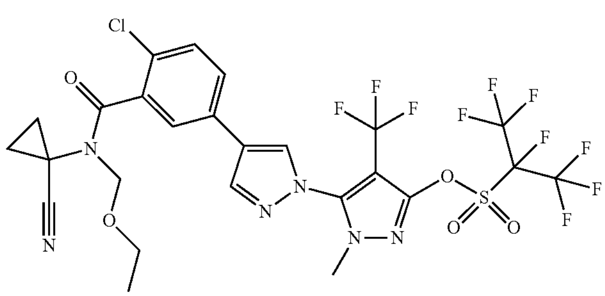 [SMILES: CCOCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-(ethoxymethyl)carbamoyl]phenyl]pyrazol-1-yl]-1-methyl-4-(trifluoromethyl)pyrazol-3-yl] 1,1,1,2,3,3,3-heptafluoropropane-2-sulfonate |

| Ex. No. | Structure | |
|---|---|---|
| 48 | 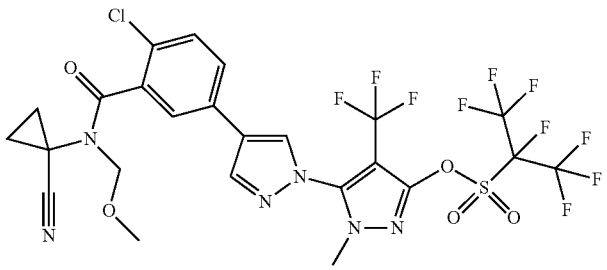 [SMILES: COCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-(methoxymethyl)carbamoyl]phenyl]pyrazol-1-yl]-1-methyl-4-(trifluoromethyl)pyrazol-3-yl] 1,1,1,2,3,3,3-heptafluoropropane-2-sulfonate |
| 49 | 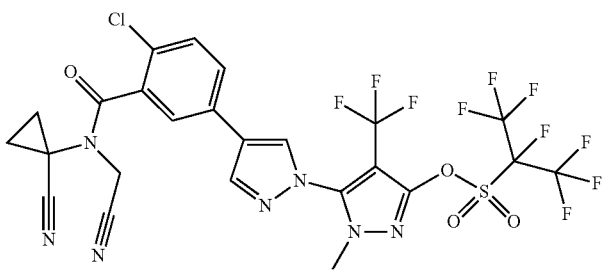 [SMILES: Cn1nc(OS(=O)(=O)C(F)(C(F)(F)F)C(F)(F)F)c(C(F)(F)F)c1-n1cc(-c2ccc(Cl)c(C(=O)N(CC#N)C3(C#N)CC3)c2)cn1] | [5-[4-[4-chloro-3-[(1-cyanocyclopropyl)-(cyanomethyl)carbamoyl]phenyl]pyrazol-1-yl]-1-methyl-4-(trifluoromethyl)pyrazol-3-yl] 1,1,1,2,3,3,3-heptafluoropropane-2-sulfonate |
| 50 | 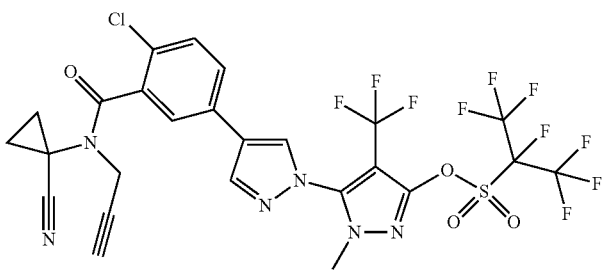 [SMILES: C#CCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-prop-2-ynyl-carbamoyl]phenyl]pyrazol-1-yl]-1-methyl-4-(trifluoromethyl)pyrazol-3-yl] 1,1,1,2,3,3,3-heptafluoropropane-2-sulfonate |
| 51 | 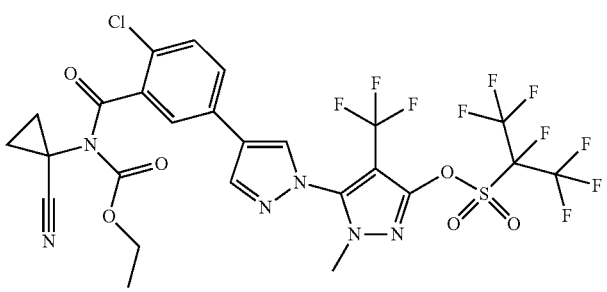 [SMILES: CCOC(=O)N(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-ethoxycarbonyl-carbamoyl]phenyl]pyrazol-1-yl]-1-methyl-4-(trifluoromethyl)pyrazol-3-yl] 1,1,1,2,3,3,3-heptafluoropropane-2-sulfonate |
| 52 | 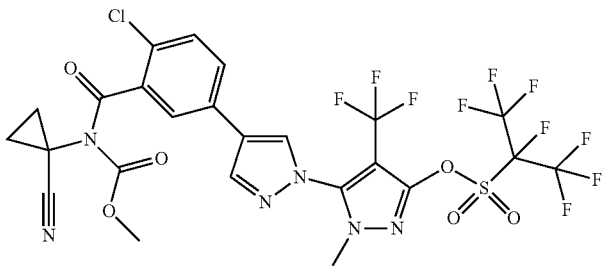 [SMILES: COC(=O)N(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-methoxycarbonyl-carbamoyl]phenyl]pyrazol-1-yl]-1-methyl-4-(trifluoromethyl)pyrazol-3-yl] 1,1,1,2,3,3,3-heptafluoropropane-2-sulfonate |

| Ex. No. | Structure | |
|---|---|---|
| 54 | 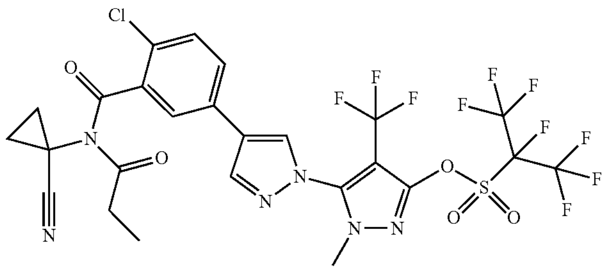 [SMILES: CCC(=O)N(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-propanoyl-carbamoyl]phenyl]pyrazol-1-yl]-1-methyl-4-(trifluoromethyl)pyrazol-3-yl] 1,1,1,2,3,3,3-heptafluoropropane-2-sulfonate |
| 56 | 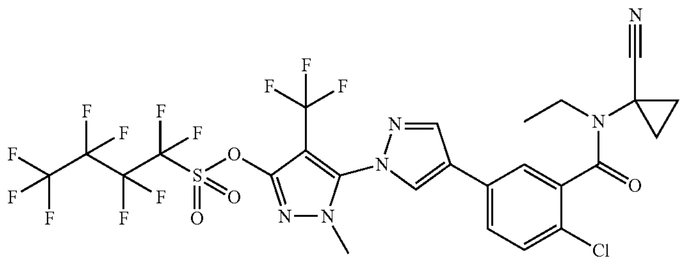 [SMILES: CCN(C(=O)c1cc(-c2cnn(-c3c(C(F)(F)F)c(OS(=O)(=O)C(F)(F)C(F)(F)C(F)(F)C(F)(F)F)nn3C)c2)ccc1Cl)C1(C#N)CC1] | [5-[4-[4-chloro-3-[(1-cyanocyclopropyl)-ethyl-carbamoyl]phenyl]pyrazol-1-yl]-1-methyl-4-(trifluoromethyl)pyrazol-3-yl] 1,1,2,2,3,3,4,4,4-nonafluorobutane-1-sulfonate |
| 57 | 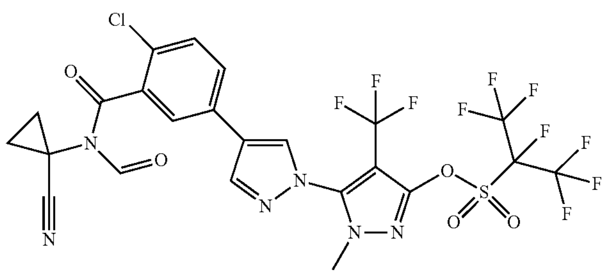 [SMILES: Cn1nc(OS(=O)(=O)C(F)(C(F)(F)F)C(F)(F)F)c(C(F)(F)F)c1-n1cc(-c2ccc(Cl)c(C(=O)N(C=O)C3(C#N)CC3)c2)cn1] | [5-[4-[4-chloro-3-[(1-cyanocyclopropyl)-formyl-carbamoyl]phenyl]pyrazol-1-yl]-1-methyl-4-(trifluoromethyl)pyrazol-3-yl] 1,1,1,2,3,3,3-heptafluoropropane-2-sulfonate |
| 58 | 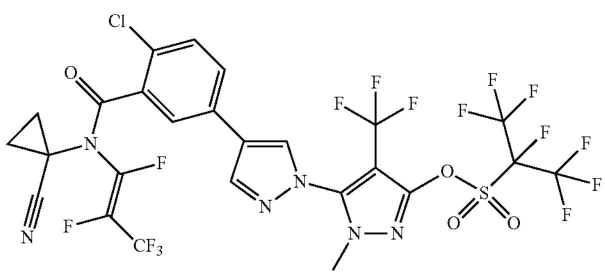 [SMILES: Cn1nc(OS(=O)(=O)C(F)(C(F)(F)F)C(F)(F)F)c(C(F)(F)F)c1-n1cc(-c2ccc(Cl)c(C(=O)N(/C(F)=C(\F)C(F)(F)F)C3(C#N)CC3)c2)cn1] | [5-[4-[4-chloro-3-[(1-cyanocyclopropyl)-[(E)-1,2,3,3,3-pentafluoroprop-1-enyl]carbamoyl]phenyl]pyrazol-1-yl]-1-methyl-4-(trifluoromethyl)pyrazol-3-yl] 1,1,1,2,3,3,3-heptafluoropropane-2-sulfonate |
| 59 | 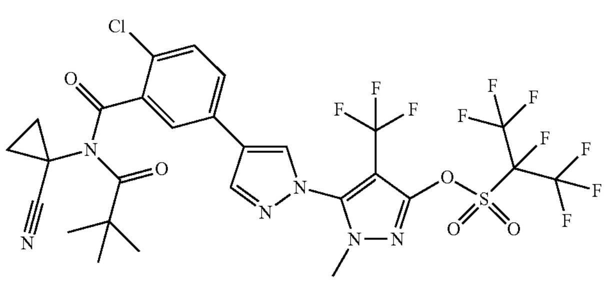 [SMILES: Cn1nc(OS(=O)(=O)C(F)(C(F)(F)F)C(F)(F)F)c(C(F)(F)F)c1-n1cc(-c2ccc(Cl)c(C(=O)N(C(=O)C(C)(C)C)C3(C#N)CC3)c2)cn1] | [5-[4-[4-chloro-3-[(1-cyanocyclopropyl)-(2,2-dimethylpropanoyl)carbamoyl]phenyl]pyrazol-1-yl]-1-methyl-4-(trifluoromethyl)pyrazol-3-yl] 1,1,1,2,3,3,3-heptafluoropropane-2-sulfonate |

| Ex. No. | Structure | |
|---|---|---|
| 60 | 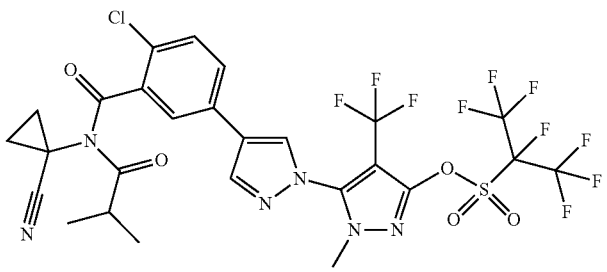 [SMILES: CC(C)C(=O)N(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-(2-methylpropanoyl)carbamoyl]phenyl]pyrazol-1-yl]-1-methyl-4-(trifluoromethyl)pyrazol-3-yl] 1,1,1,2,3,3,3-heptafluoropropane-2-sulfonate |
| 62 | 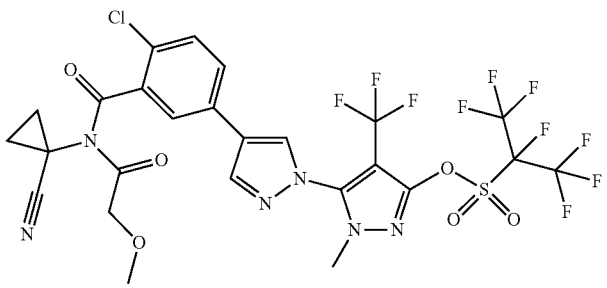 [SMILES: COCC(=O)N(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-(2-methoxyacetyl)carbamoyl]phenyl]pyrazol-1-yl]-1-methyl-4-(trifluoromethyl)pyrazol-3-yl] 1,1,1,2,3,3,3-heptafluoropropane-2-sulfonate |
| 64 | 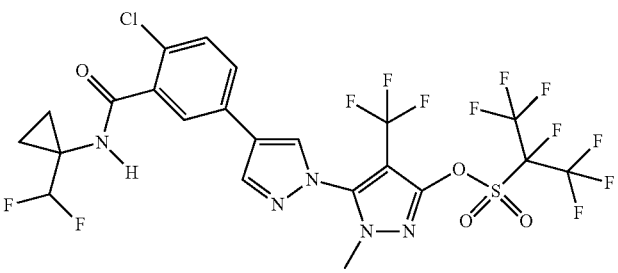 [SMILES: Cn1nc(OS(=O)(=O)C(F)(C(F)(F)F)C(F)(F)F)c(C(F)(F)F)c1-n1cc(-c2ccc(Cl)c(C(=O)NC3(C(F)F)CC3)c2)cn1] | [5-[4-[4-chloro-3-[[1-(difluoromethyl)cyclopropyl]carbamoyl]phenyl]pyrazol-1-yl]-1-methyl-4-(trifluoromethyl)pyrazol-3-yl] 1,1,1,2,3,3,3-heptafluoropropane-2-sulfonate |
| 65 | 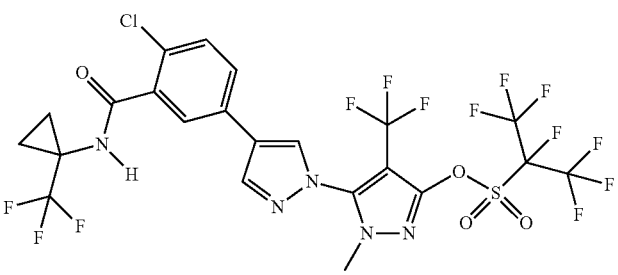 [SMILES: Cn1nc(OS(=O)(=O)C(F)(C(F)(F)F)C(F)(F)F)c(C(F)(F)F)c1-n1cc(-c2ccc(Cl)c(C(=O)NC3(C(F)(F)F)CC3)c2)cn1] | [5-[4-[4-chloro-3-[[1-(trifluoromethyl)cyclopropyl]carbamoyl]phenyl]pyrazol-1-yl]-1-methyl-4-(trifluoromethyl)pyrazol-3-yl] 1,1,1,2,3,3,3-heptafluoropropane-2-sulfonate |
| 67 | 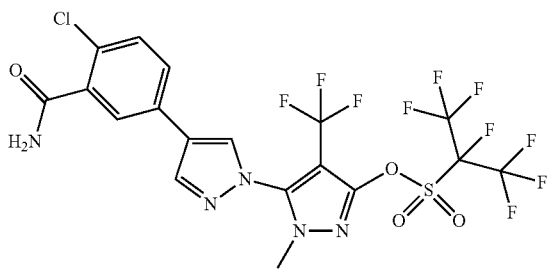 [SMILES: Cn1nc(OS(=O)(=O)C(F)(C(F)(F)F)C(F)(F)F)c(C(F)(F)F)c1-n1cc(-c2ccc(Cl)c(C(N)=O)c2)cn1] | [5-[4-(3-carbamoyl-4-chloro-phenyl)pyrazol-1-yl]-1-methyl-4-(trifluoromethyl)pyrazol-3-yl] 1,1,1,2,3,3,3-heptafluoropropane-2-sulfonate |

| Ex. No. | Structure | |
|---|---|---|
| 68 | 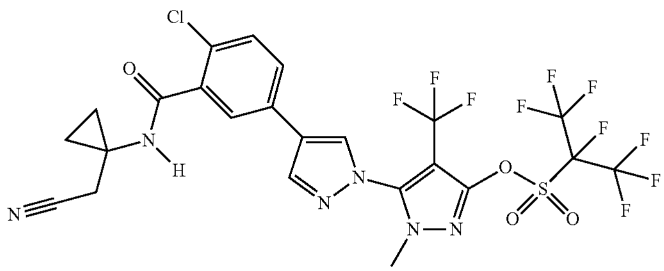 [SMILES: Cn1nc(OS(=O)(=O)C(F)(C(F)(F)F)C(F)(F)F)c(C(F)(F)F)c1-n1cc(-c2ccc(Cl)c(C(=O)NC3(CC#N)CC3)c2)cn1] | [5-[4-[4-chloro-3-[[1-(cyanomethyl)cyclopropyl]carbamoyl]phenyl]pyrazol-1-yl]-1-methyl-4-(trifluoromethyl)pyrazol-3-yl] 1,1,1,2,3,3,3-heptafluoropropane-2-sulfonate |
| 69 | 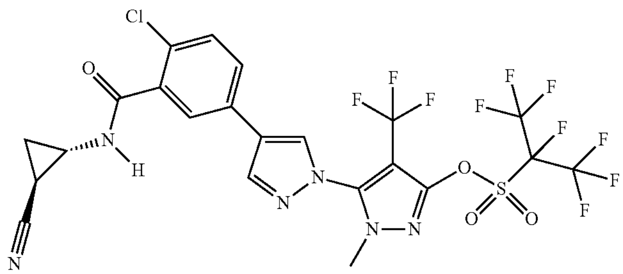 [SMILES: Cn1nc(OS(=O)(=O)C(F)(C(F)(F)F)C(F)(F)F)c(C(F)(F)F)c1-n1cc(-c2ccc(Cl)c(C(=O)N[C@H]3C[C@@H]3C#N)c2)cn1] | (rac)-[5-[4-[4-chloro-3-[[(1S,2S)-2-cyanocyclopropyl]carbamoyl]phenyl]pyrazol-1-yl]-1-methyl-4-(trifluoromethyl)pyrazol-3-yl] 1,1,1,2,3,3,3-heptafluoropropane-2-sulfonate |
| 71 | 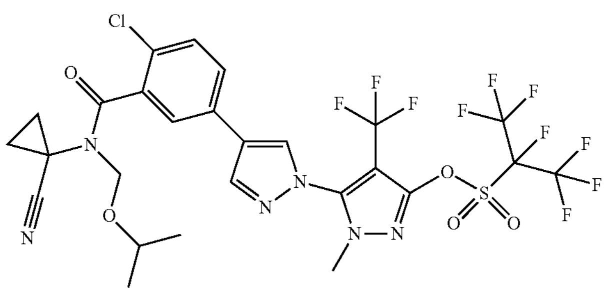 [SMILES: CC(C)OCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-(isopropoxymethyl)carbamoyl]phenyl]pyrazol-1-yl]-1-methyl-4-(trifluoromethyl)pyrazol-3-yl] 1,1,1,2,3,3,3-heptafluoropropane-2-sulfonate |
| 72 | 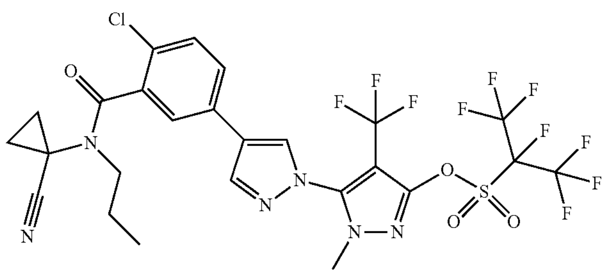 [SMILES: CCCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-propyl-carbamoyl]phenyl]pyrazol-1-yl]-1-methyl-4-(trifluoromethyl)pyrazol-3-yl] 1,1,1,2,3,3,3-heptafluoropropane-2-sulfonate |
| 73 | 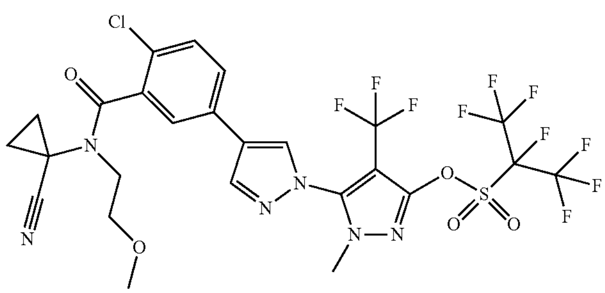 [SMILES: COCCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-(2-methoxyethyl)carbamoyl]phenyl]pyrazol-1-yl]-1-methyl-4-(trifluoromethyl)pyrazol-3-yl] 1,1,1,2,3,3,3-heptafluoropropane-2-sulfonate |

| Ex. No. | Structure | |
|---|---|---|
| 74 | 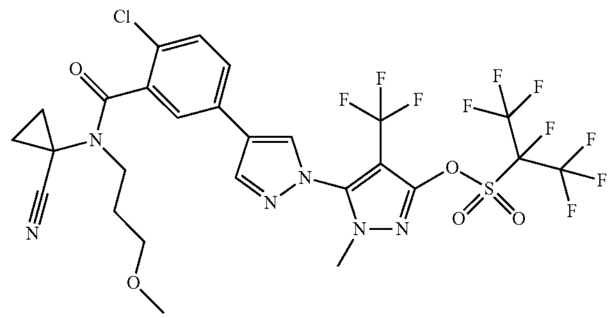 [SMILES: COCCCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | [5-[4-[4-chloro-3-[(1-cyanocyclopropyl)-(3-methoxypropyl)carbamoyl]phenyl]pyrazol-1-yl]-1-methyl-4-(trifluoromethyl)pyrazol-3-yl] 1,1,1,2,3,3,3-heptafluoropropane-2-sulfonate |
| 75 | | [5-[4-[4-chloro-3-[(1-cyanocyclopropyl)-isopropoxycarbonyl-carbamoyl]phenyl]pyrazol-1-yl]-1-methyl-4-(trifluoromethyl)pyrazol-3-yl] 1,1,1,2,3,3,3-heptafluoropropane-2-sulfonate | or an agrochemically acceptable salt or N-oxide thereof.

For clarity purposes, in embodiment 34, there are no examples 53, 55, 61, 63, 66 and 70.

As used herein, when one embodiment refers to several other embodiments by using the term "according to any one of", for example "according to any one of embodiments 1 to 23", then said embodiment refers not only to embodiments indicated by integers such as 1 and 2 but also to embodiments indicated by numbers with a decimal component such as 23.1, 23.2, 23.3, 23.4, 23.20, 23.25, 23.30.

Definitions

The term "Alkyl" as used herein—in isolation or as part of a chemical group—represents straight-chain or branched hydrocarbons, preferably with 1 to 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Alkyl groups with 1 to 4 carbon atoms are preferred, for example methyl, ethyl, n-propyl, isopropyl, n-butyl, isobutyl, s-butyl or t-butyl.

The term "Alkenyl"—in isolation or as part of a chemical group—represents straight-chain or branched hydrocarbons, preferably with 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl und 1-ethyl-2-methyl-2-propenyl. Alkenyl groups with 2 to 4 carbon atoms are preferred, for example 2-propenyl, 2-butenyl or 1-methyl-2-propenyl.

The term "Alkynyl"—in isolation or as part of a chemical group—represents straight-chain or branched hydrocarbons, preferably with 2 to 6 carbon atoms and at least one triple bond, for example 2-propinyl, 2-butinyl, 3-butinyl, 1-methyl-2-propinyl, 2-pentinyl, 3-pentinyl, 4-pentinyl, 1-methyl-3-butinyl, 2-methyl-3-butinyl, 1-methyl-2-butinyl, 1,1-dimethyl-2-propinyl, 1-ethyl-2-propinyl, 2-hexinyl, 3-hexinyl, 4-hexinyl, 5-hexinyl, 1-methyl-2-pentinyl, 1-methyl-3-pentinyl, 1-methyl-4-pentinyl, 2-methyl-3-pentinyl, 2-methyl-4-pentinyl, 3-methyl-4-pentinyl, 4-methyl-2-pentinyl, 1,1-dimethyl-3-butinyl, 1,2-dimethyl-3-butinyl, 2,2-dimethyl-3-butinyl, 1-ethyl-3-butinyl, 2-ethyl-3-butinyl, 1-ethyl-1-methyl, 1,2-propinyl and 2,5-hexadiynyl. Alkynyls with 2 to 4 carbon atoms are preferred, for example ethinyl, 2-propinyl or 2-butinyl-2-propenyl.

The term "cycloalkyl"—in isolation or as part of a chemical group—represents saturated or partially unsaturated mono-, bi- or tricyclic hydrocarbons, preferably 3 to 10 carbon atoms, for example cyclopropyl, cyclobutyl, cyclopentyl, cyclohexyl, cycloheptyl, cyclooctyl, bicyclo[2.2.1]heptyl, bicyclo[2.2.2]octyl or adamantyl.

Cycloalkyls with 3, 4, 5, 6 or 7 carbon atoms are preferred, for example cyclopropyl or cyclobutyl.

The term "heterocycloalkyl"—in isolation or as part of a chemical group—represents saturated or partially unsaturated mono-, bi- or tricyclic hydrocarbons, preferably 3 to 10 carbon atoms, for example cyclopropyl, cyclobutyl, cyclopentyl, cyclohexyl, cycloheptyl, cyclooctyl, bicyclo[2.2.1]heptyl, bicyclo[2.2.2]octyl or adamantyl, wherein one or more of the ring atoms, preferably 1 to 4, more preferably 1, 2 or 3 of the ring atoms are independently selected from N, O, S, P, B, Si and Se, more preferably N, O and S, wherein no O atoms can be located next to each other.

The term "Alkylcycloalkyl" represents mono-, bi- or tricyclic alkylcycloalkyl, preferably with 4 to 10 or 4 to 7 carbon atoms, for example ethylcyclopropyl, isopropylcyclobutyl, 3-methylcyclopentyl and 4-methyl-cyclohexyl. Alkylcycloalkyls with 4, 5 or 7 carbon atoms are preferred, for example ethylcyclopropyl or 4-methyl-cyclohexyl.

The term "halogen" represents fluoro, chloro, bromo or iodo, particularly fluoro, chloro or bromo. The chemical groups which are substituted with halogen, for example haloalkyl, halocycloalkyl, haloalkyloxy, haloalkylsulfanyl, haloalkylsulfinyl or haloalkylsulfonyl are substituted one or up to the maximum number of substituents with halogen. If "alkyl", "alkenyl" or "alkynyl" are substituted with halogen, the halogen atoms can be the same or different and can be bound at the same carbon atom or different carbon atoms.

The term "halocycloalkyl" represents mono-, bi- or tricyclic halocycloalkyl, preferably with 3 to 10 carbon atoms, for example 1-fluoro-cyclopropyl, 2-fluoro-cyclopropyl or 1-fluoro-cyclobutyl. Preferred halocycloalkyl with 3, 5 or 7 carbon atoms.

The term "haloalkyl", "haloalkenyl" or "haloalkynyl" represents alkyls, alkenyls or alkynyls as defined above substituted with halogen, preferably with 1 to 9 halogen atoms that are the same or different, for example monohaloalkyls (=monohaloalkyl) like $CH_2CH_2Cl$, $CH_2CH_2F$, $CHClCH_3$, $CHFCH_3$, $CH_2Cl$, $CH_2F$; perhaloalkyls like $CCl_3$ or $CF_3$ or $CF_2CF_3$; polyhaloalkyls like $CHF_2$, $CH_2F$, $CH_2CHFCl$, $CF_2CF_2H$, $CH_2CF_3$. The same applies for haloalkenyl and other groups substituted by halogen.

Examples of haloalkoxy are for example $OCF_3$, $OCHF_2$, $OCH_2F$, $OCF_2CF_3$, $OCH_2CF_3$, $OCF_3$, $OCHF_2$, $OCH_2F$, $OCF_2CF_3$, $OCH_2CF_3$.

Further examples of haloalkyls are trichloromethyl, chlorodifluoromethyl, dichlorofluoromethyl, 1-fluoroethyl, 2-fluoroethyl, 2,2-difluoroethyl, 2,2,2-trifluorethyl, 2,2,2-trichloroethyl, 2-chloro-2,2-difluoroethyl, pentafluorethyl and pentafluoro-t-butyl.

Haloalkyls having 1 to 4 carbon atoms and 1 to 9, preferably 1 to 5 of the same or different halogen atoms selected from fluoro, chloro or bromo, are preferred.

Haloalkyls having 1 or 2 carbon atoms and 1 to 5 of the same or different halogen atoms selected from fluoro or chloro, for example difluoromethyl, trifluoromethyl or 2,2-difluoroethyl, are particularly preferred.

The term "hydroxyalkyl" represents straight or branched chain alcohols, preferably with 1 to 6 carbon atoms, for example methanol, ethanol, n-propanol, isopropanol, n-butanol, isobutanol, s-butanol and t-butanol. Hydroxyalkyls having 1 to 4 carbon atoms are preferred.

The term "alkoxy" represents straight or branched chain O-alkyl, preferably having 1 to 6 carbon atoms, for example methoxy, ethoxy, n-propoxy, isopropoxy, n-butoxy, isobutoxy, s-butoxy and t-butoxy. Alkoxy having 1 to 4 carbon atoms are preferred.

The term "haloalkoxy" represents straight or branched chain O-alkyl substituted with halogen, preferably with 1 to 6 carbon atoms, for example difluoromethoxy, trifluoromethoxy, 2,2-difluoroethoxy, 1,1,2,2-tetrafluoroethoxy, 2,2,2-Trifluoroethoxy and 2-Chloro-1,1,2-trifluoroethoxy. Haloalkoxy having 1 to 4 carbon atoms are preferred.

The term "alkylcarbonyl" represents straight or branched chain alkyl-C(=O), preferably having 2 to 7 carbon atoms, for example methylcarbonyl, ethylcarbonyl, n-propylcarbonyl, isopropylcarbonyl, s-butylcarbonyl and t-butylcarbonyl. Alkylcarbonyls having 1 to 4 carbon atoms are preferred.

The term "cycloalkylcarbonyl" represents cycloalkyl-carbonyl, preferably 3 to 10 carbon atoms in the cycloalkyl part, for example cyclopropylcarbonyl, cyclobutylcarbonyl, cyclopentylcarbonyl, cyclohexyl-carbonyl, cycloheptyl-carbonyl, cyclooctylcarbonyl, bicyclo[2.2.1]heptyl, bycyclo[2.2.2]octylcarbonyl and adamantylcarbonyl. Cycloalkylcarbonyls having 3, 5 or 7 carbon atoms in the cycloalkyl part are preferred.

The term "alkoxycarbonyl""—in isolation or as part of a chemical group—represents straight or branched chain alkoxycarbonyl, preferably having 1 to 6 carbon atoms or 1 to 4 carbon atoms in the alkoxy part, for example methoxycarbonyl, ethoxycarbonyl, n-propoxycarbonyl, isopropoxycarbonyl, s-butoxycarbonyl and t-butoxycarbonyl.

The term "alkylaminocarbonyl" represents straight or branched chain alkylaminocarbonyl having preferably 1 to 6 carbon atoms or 1 to 4 carbon atoms in the alkyl part, for example methylaminocarbonyl, ethylaminocarbonyl, n-proylaminocarbonyl, isopropyl-aminocarbonyl, s-butylaminocarbonyl and t-butylaminocarbonyl.

The term "N,N-Dialkylamino-carbonyl" "represents straight or branched chain N,N-dialkylaminocarbonyl with preferably 1 to 6 carbon atoms or 1 to 4 carbon atoms in the alkyl part, for example N,N-Dimethylamino-carbonyl, N,N-diethylamino-carbonyl, N,N-di(n-propylamino)-carbonyl, N,N-di(isopropylamino)-carbonyl and N,N-di-(s-butylamino)-carbonyl.

The term "aryl" represents a mono-, bi- or polycyclical aromatic system with preferably 6 to 14, more preferably 6 to 10 ring-carbon atoms, for example phenyl, naphthyl, anthryl, phenanthrenyl, preferably phenyl. "Aryl" also represents polycyclic systems, for example tetrahydronaphtyl, indenyl, indanyl, fluorenyl, biphenyl. Arylalkyls are examples of substituted aryls, which may be further substituted with the same or different substituents both at the aryl or alkyl part. Benzyl and 1-phenylethyl are examples of such arylalkyls.

The term "heterocyclyl", "heterocyclic ring" or "heterocyclic ring system" represents a carbocyclic ring system with at least one ring, in which ring at least one carbon atom is replaced by a heteroatom, preferably selected from N, O, S, P, B, Si, Se, and which ring is saturated, unsaturated or partially saturated, and which ring is unsubstituted or substituted with a substituent Z, wherein the connecting bond is located at a ring atom. Unless otherwise defined, the heterocyclic ring has preferably 3 to 9 ring atoms, preferably 3 to 6 ring atoms, and one or more, preferably 1 to 4, more preferably 1, 2 or 3 heteroatoms in the heterocyclic ring, preferably selected from N, O, and S, wherein no O atoms can be located next to each other. The heterocyclic rings normally contain no more than 4 nitrogens, and/or no more than 2 oxygen atoms and/or no more than 2 sulfur atoms. In case that the heterocyclic substituent or the heterocyclic ring are further substituted, it can be further annulated with other heterocyclic rings.

The term "heterocyclic" also includes polycyclic systems, for example 8-aza-bicyclo[3.2.1]octanyl or 1-aza-bicyclo[2.2.1]heptyl.

The term "heterocyclic" also includes spirocyclic systems, for example 1-oxa-5-aza-spiro[2.3]hexyl.

Examples of heterocyclyls are for example piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl. Particularly important are heteroaryls, i.e. heteroaromatic systems.

The term "heteroaryl" represents heteroaromatic groups, i.e. completely unsaturated aromatic heterocyclic groups, which fall under the above definition of heterocycls. "Heteroaryls" with 5 to 7-membered rings with 1 to 3, preferably 1 or 2 of the same or different heteroatoms selected from N, O, and S. Examples of "heteroaryls" are furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl.

A compound according to any one of embodiments 1 to 34 which has at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. A compounds according to any one of embodiments 1 to 20 which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

Compounds according to any one of embodiments 1 to 34 also include hydrates which may be formed during the salt formation.

The compounds according to any one of embodiments 1 to 34 may be made by a variety of methods well known to a person skilled in the art or as shown in Schemes 1 to 2. Further instructions regarding the preparation can be found in WO2017/055414, WO2017/108569, WO2017/140771, WO2017/012970, WO2015/067646, WO2015/150442, WO2014/122083 and WO2012/107434.

For example, compounds of formula (I) may be prepared, for example, according to Scheme 1,

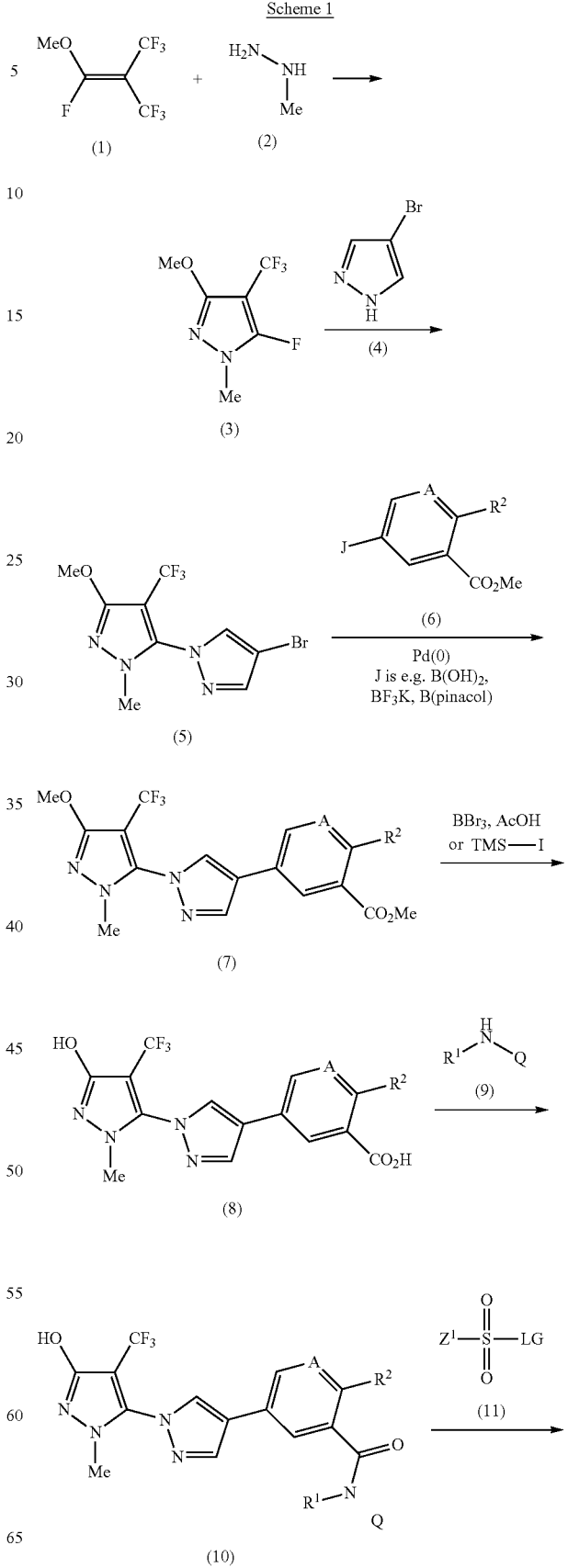

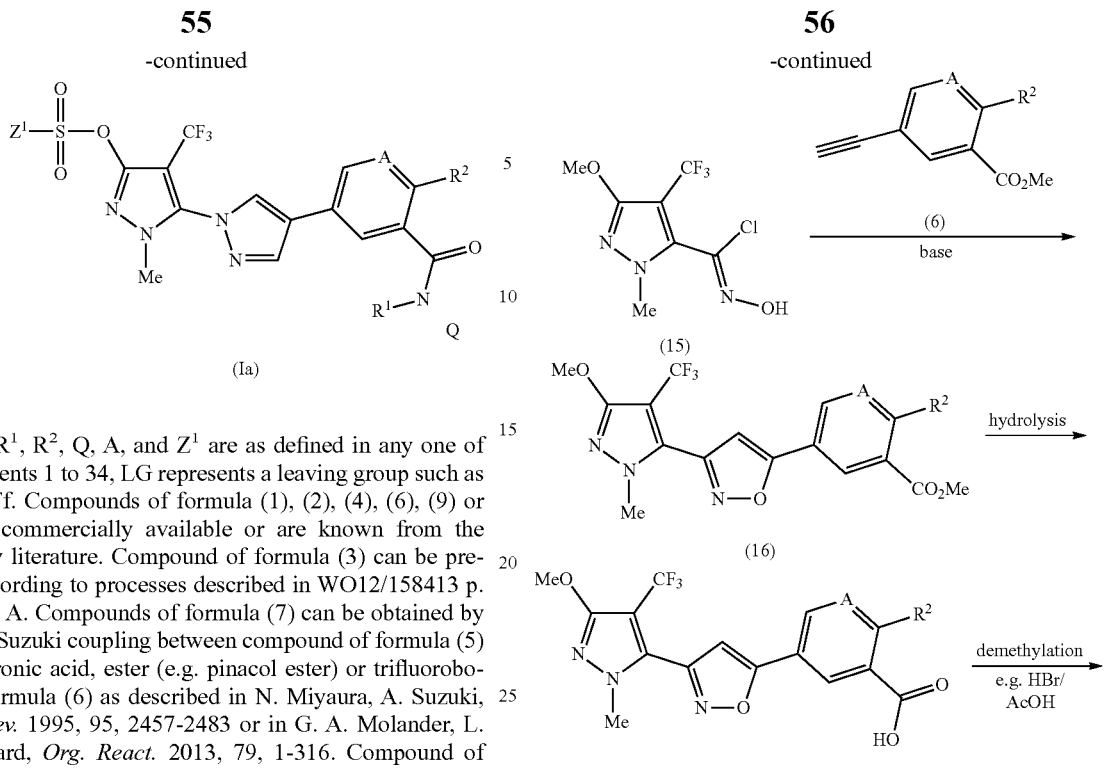

wherein $R^1$, $R^2$, Q, A, and $Z^1$ are as defined in any one of embodiments 1 to 34, LG represents a leaving group such as F, Cl, OTf. Compounds of formula (1), (2), (4), (6), (9) or (11) are commercially available or are known from the chemistry literature. Compound of formula (3) can be prepared according to processes described in WO12/158413 p. 371, Step A. Compounds of formula (7) can be obtained by classical Suzuki coupling between compound of formula (5) and a boronic acid, ester (e.g. pinacol ester) or trifluoroborate of formula (6) as described in N. Miyaura, A. Suzuki, *Chem. Rev.* 1995, 95, 2457-2483 or in G. A. Molander, L. Jean-Gérard, *Org. React.* 2013, 79, 1-316. Compound of formula (Ia) can be prepared by sulfonylation as described in *Tetrahedron* 2009, 65, 7817-7824

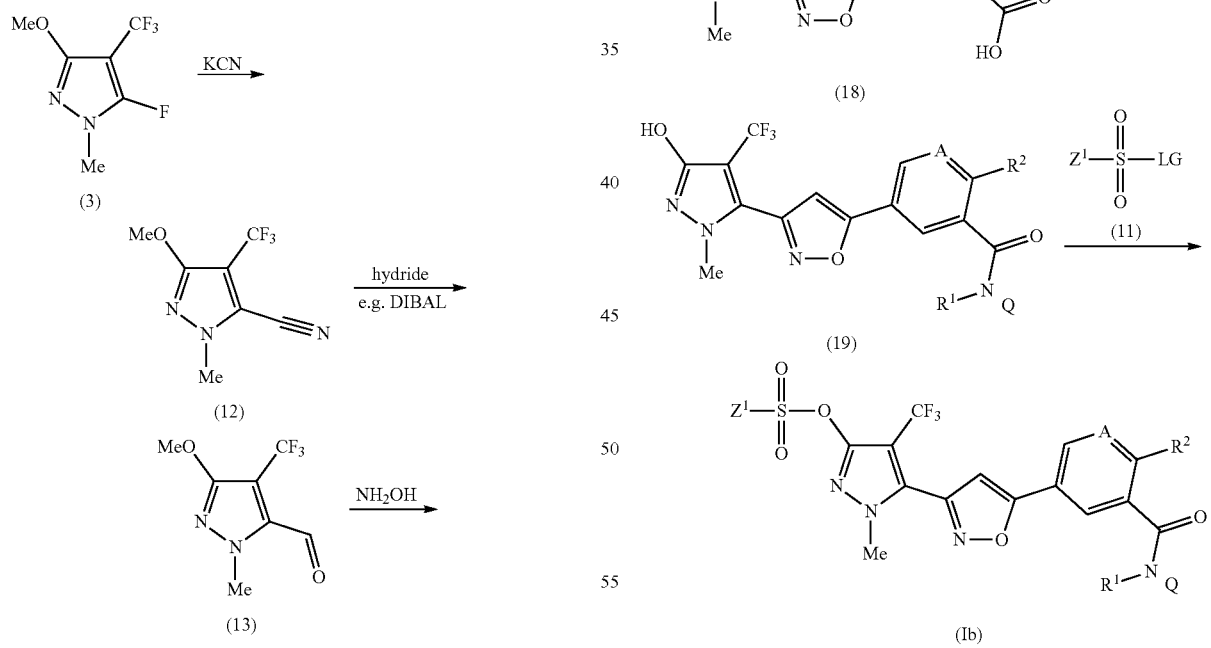

wherein $R^1$, $R^2$, Q, A, and $Z^1$ are as defined in any one of embodiments 1 to 34, LG represents a leaving group such as F, Cl, OTf. Compounds of formula (6), (9) or (11) are commercially available or are known from the chemistry literature. Compound of formula (3) can be prepared according to processes described in WO12/158413 p. 371, Step A. Compounds of formula (16) may be prepared according to known literature methods by reacting compound (15) with compounds (6) in the presence of a base in a suitable solvent and at a suitable temperature (information can be found in WO2015/067646, p. 145-147). Compounds of formula (Ia) can be prepared by sulfonylation as described in *Tetrahedron* 2009, 65, 7817-7824

A compound according to any one of embodiments 1 to 34 can be converted in a manner known per se into another compound according to any one of embodiments 1 to 34 by replacing one or more substituents of the starting compound according to any one of embodiments 1 to 34 in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula (I) can be prepared in a manner known per se. Thus, for example, acid addition salts of compounds according to any one of embodiments 1 to 34 are obtained by treatment with a suitable acid or a suitable ion exchanger reagent and salts with bases are obtained by treatment with a suitable base or with a suitable ion exchanger reagent.

Salts of compounds according to any one of embodiments 1 to 34 can be converted in the customary manner into the free compounds, acid addition salts, for example, by treatment with a suitable basic compound or with a suitable ion exchanger reagent and salts with bases, for example, by treatment with a suitable acid or with a suitable ion exchanger reagent.

Salts of compounds according to any one of embodiments 1 to 34 can be converted in a manner known per se into other salts of compounds according to any one of embodiments 1 to 34, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds according to any one of embodiments 1 to 34, which have salt-forming properties can be obtained in free form or in the form of salts.

The compounds according to any one of embodiments 1 to 34 and, where appropriate, the tautomers thereof, in each case in free form or in salt form, can be present in the form of one of the stereoisomers which are possible or as a mixture of these, for example in the form of pure stereoisomers, such as antipodes and/or diastereomers, or as stereoisomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure stereoisomers and also to all stereoisomer mixtures which are possible and is to be understood in each case in this sense hereinabove and hereinbelow, even when stereochemical details are not mentioned specifically in each case.

Diastereomer mixtures or racemate mixtures of compounds according to any one of embodiments 1 to 34, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable stereoisomer mixtures, but also by generally known methods of diastereoselective or enantioselective synthesis, for example by carrying out the process according to the invention with starting materials of a suitable stereochemistry.

N-oxides can be prepared by reacting a compound according to any one of embodiments 1 to 34 with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective stereoisomer, for example enantiomer or diastereomer, or stereoisomer mixture, for example enantiomer mixture or diastereomer mixture, if the individual components have a different biological activity.

The compounds according to any one of embodiments 1 to 34 and, where appropriate, the tautomers thereof, in each case in free form or in salt form, can, if appropriate, also be obtained in the form of hydrates and/or include other solvents, for example those which may have been used for the crystallization of compounds which are present in solid form.

The following Examples illustrate, but do not limit, the invention.

The present invention also provides intermediates useful for the preparation of compounds according to any one of embodiments 1 to 34. Certain intermediates are novel and as such form a further aspect of the invention.

One group of novel intermediates are compounds of formula (II)

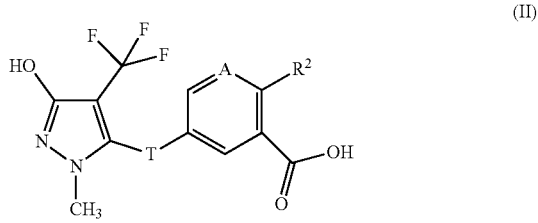

wherein A, T and R² are as defined in any one of embodiments 1 to 34. The preferences for A, T and R² are the same as the preferences set out for the corresponding substituents of a compound according to any one of embodiments 1 to 34.

Another group of novel intermediates are compounds of formula (III)

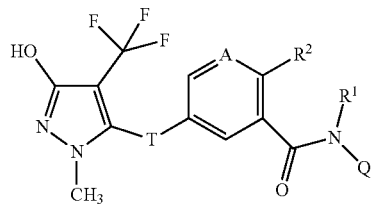

wherein A, T, R¹, R² and Q are as defined in any one of embodiments 1 to 34. The preferences for A, T, R¹, R² and Q are the same as the preferences set out for the corresponding substituents of a compound according to any one of embodiments 1 to 34.

The compounds according to any one of embodiments 1 to 34 are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the above mentioned animal pests are:
from the order Acarina, for example,
*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;
from the order Anoplura, for example,
*Haematopinus* spp., *Linognathus* spp., *Pediculus* spp., *Pemphigus* spp. and *Phylloxera* spp.;
from the order Coleoptera, for example,
*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp., *Dermestes* spp., *Diabrotica* spp., *Diloborderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;
from the order Diptera, for example,
*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;
from the order Hemiptera, for example,
*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens;*
*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris;*
from the order Hymenoptera, for example,
*Acromyrmex*, *Arge* spp, *Atta* spp., *Cephus* spp., *Diprion* spp., *Diprionidae*, *Gilpinia polytoma*, *Hoplo-campa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis* geminate from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocolletuis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds according to any one of embodiments 1 to 34 may also have activity against the molluscs. Examples of which include, for example, Ampullariidae; *Arion (A. ater, A. circumscriptus, A. hortensis, A. rufus)*; Bradybaenidae (*Bradybaena fruticum*); Cepaea (*C. hortensis, C. Nem-*

*oralis*); ochlodina; *Deroceras* (*D. agrestis, D. empiricorum, D. laeve, D. reticulatum*); *Discus* (*D. rotundatus*); *Euomphalia*; *Galba* (*G. trunculata*); *Helicelia* (*H. itala, H. obvia*); *Helicidae Helicigona arbustorum*); Helicodiscus; *Helix* (*H. aperta*); *Limax* (*L. cinereoniger, L. flavus, L. marginatus, L. maximus, L. tenellus*); Lymnaea; *Milax* (*M. gagates, M. marginatus, M. sowerbyi*); Opeas; *Pomacea* (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens*, *Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4

EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerant to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In another embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| | *Xylosandrus crassiusculus* | Hardwoods |
| Scolytidae | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| | *Goes pulverulentus* | Beech, Elm, Nuttall, Willow, Black oak, Cherrybark oak, Water oak, Sycamore |

TABLE B-continued

Examples of native woodborers of economic importance.

| Family | Species | Host or Crop Infested |
|---|---|---|
| Cerambycidae | Goes tigrinus | Oak |
| | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |
| | Oncideres cingulata | Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| | Corthylus columbianus | Maple, Oak, Yellow-poplar, Beech, Boxelder, Sycamore, Birch, Basswood, Chestnut, Elm |
| | Dendroctonus frontalis | Pine |
| Scolytidae | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| Sesiidae | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

In one aspect, the invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to any one of embodiments 1 to 34 and which are to be selected to suit the intended aims and the prevailing circumstances. In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature. Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):
Emulsifiable Concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

EXAMPLES

The following compounds according to embodiment 1 may be prepared according to the methods described herein or according to known methods, e.g. as disclosed in WO2017/108569.

Experimental

The following examples are intended to illustrate the invention and are not to be construed as being limitations thereon.

"Mp" means melting point in ° C. $^1$H NMR measurements were recorded on a Brucker 400 MHz spectrometer, chemical shifts are given in ppm relevant to a TMS standard. Spectra measured in deuterated solvents as indicated.

Preparation of 5-fluoro-3-methoxy-1-methyl-4-(trifluoromethyl)pyrazole

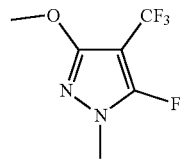

A mixture of methylhydrazine (1.32 ml, 24.6 mmol) and triethylamine (3.15 ml, 22.4 mmol) in 12 ml of ethanol was added dropwise at 25° C.-30° C. to a solution of 1-methoxy-(perfluoro-2-methyl-1-propene) (3.32 ml, 22.4 mmol) in 8 ml of ethanol. The addition was exothermic and the reaction was stirred overnight at room temperature. The ethanol was carefully evaporated, residue was diluted with tert-butyl methyl ether, and the organic layer was washed with water, brine, dried over sodium sulfate, filtrated and evaporated to give the crude product as yellow oil.

$^1$H NMR (400 MHz, CDCl$_3$) δ ppm 3.61 (d, 3H) 3.90 (s, 3H).

Preparation of 5-(4-bromopyrazol-1-yl)-3-methoxy-1-methyl-4-(trifluoromethyl)pyrazole

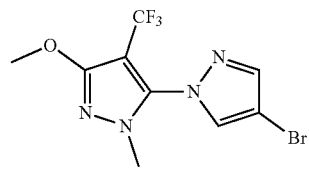 [SMILES: COc1nn(C)c(-n2cc(Br)cn2)c1C(F)(F)F]

Under Argon, 5-fluoro-3-methoxy-1-methyl-4-(trifluoromethyl)pyrazole (2.9 g, 11.7 mmol), 4-bromo-1H-pyrazole (2.11 g, 14.1 mmol) and potassium carbonate (3.43 g, 24.6 mmol) were dissolved in 35 ml THF. The yellow solution was heated over 3 days at 80° C. The mixture was then diluted with tert-butyl methyl ether, quenched with 15 ml of water, extracted 2 times with 20 ml of tert-butyl methyl ether, the organic phase was washed with brine, dried over sodium sulfate, filtrated and evaporated. The crude resin obtained (4.76 g) was purified over silica to give 5-(4-bromopyrazol-1-yl)-3-methoxy-1-methyl-4-(trifluoromethyl)pyrazole.

¹H NMR (400 MHz, CDCl₃) δ ppm 3.59 (s, 3H) 3.98 (s, 3H) 7.66 (s, 1H) 7.77 (s, 1H).

Synthesis of 2-chloro-5-[1-[5-methoxy-2-methyl-4-(trifluoromethyl)pyrazol-3-yl]pyrazol-4-yl]benzoic acid

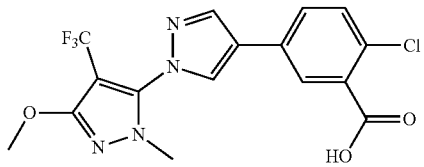 [SMILES: COc1nn(C)c(-n2cc(-c3ccc(Cl)c(C(=O)O)c3)cn2)c1C(F)(F)F]

In a 3-neck round bottom flask under argon, 5-(4-bromopyrazol-1-yl)-3-methoxy-1-methyl-4-(trifluoromethyl)pyrazole (1.81 g, 5.01 mmol), methyl 2-chloro-5-(4,4,5,5-tetramethyl-1,3,2-dioxaborolan-2-yl)benzoate (1.56 g, 5.26 mmol) and sodium hydrogen carbonate 1M (15 ml, 15 mmol) were dissolved in 30 ml of 2-propanol. The mixture was purged with argon for 5 min. After that, tetrakis(triphenylphosphine)palladium(0) (177 mg, 0.15 mmol) was added and the mixture was heated at 100° C. overnight. The mixture was filtrated, evaporated, diluted with ethyl acetate, quenched with 10 ml of sodium hydroxide 2N, and extracted 2 times with ethyl acetate. The water phase was acidified to pH 2 using hydrochloride acid 10% and extracted 3 times with 20 ml of ethyl acetate, the organic phase was washed with brine, dried over sodium sulfate, filtrated and evaporated to give 2-chloro-5-[1-[5-methoxy-2-methyl-4-(trifluoromethyl)pyrazol-3-yl]pyrazol-4-yl]benzoic acid as a yellow resin.

¹H NMR (400 MHz, CDCl₃) δ ppm 3.62-3.68 (m, 3H) 4.00 (s, 3H) 7.52-7.56 (m, 1H) 7.60-7.64 (m, 1H) 7.91 (s, 1H) 8.11 (d, 1H) 8.14 (d, 1H).

Preparation of 2-chloro-5-[1-[5-hydroxy-2-methyl-4-(trifluoromethyl)pyrazol-3-yl]pyrazol-4-yl]benzoic acid

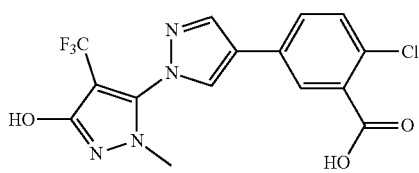 [SMILES: Cn1nc(O)c(C(F)(F)F)c1-n1cc(-c2ccc(Cl)c(C(=O)O)c2)cn1]

2-Chloro-5-[1-[5-methoxy-2-methyl-4-(trifluoromethyl)pyrazol-3-yl]pyrazol-4-yl]benzoic acid (1.99 g, 4.57 mmol) in a 33% solution HBr in AcOH (12.4 ml) was stirred under argon in a thick glass microwave tube. The colorless solution was heated at 60° C. overnight. After dilution with tert-butyl methyl ether, the solution was quenched with saturated sodium hydrogen carbonate. The water phase was acidified to pH 2 with 10% HCl and extracted with 3 times with 20 ml of ethyl acetate; the organic phase was washed with brine, dried over sodium sulfate, filtrated and evaporated. The crude beige product was purified to give 2-chloro-5-[1-[5-hydroxy-2-methyl-4-(trifluoromethyl)pyrazol-3-yl]pyrazol-4-yl]benzoic acid as white crystals.

¹H NMR (400 MHz, CD₃OD) δ ppm 3.28-3.36 (m, 3H) 3.51-3.56 (m, 3H) 7.54 (d, 1H) 7.78 (dd, 1H) 8.11 (d, 1H) 8.28 (s, 1H) 8.40 (s, 1H)

Preparation of 2-chloro-N-cyclopropyl-5-[1-[5-hydroxy-2-methyl-4-(trifluoromethyl)pyrazol-3-yl]pyrazol-4-yl]benzamide

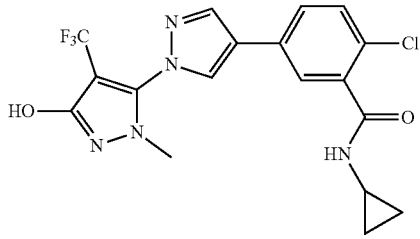 [SMILES: Cn1nc(O)c(C(F)(F)F)c1-n1cc(-c2ccc(Cl)c(C(=O)NC3CC3)c2)cn1]

To a solution of 2-chloro-5-[1-[5-hydroxy-2-methyl-4-(trifluoromethyl)pyrazol-3-yl]pyrazol-4-yl]benzoic acid (200 mg) in dimethylformamide (1.55 mL) was added Carbonyldiimidazole (102 mg). The resulting solution was stirred at room temperature for 30 min then cyclopropylamine (0.07 mL) was added. The resulting solution was stirred at room temperature for 2 hours then allowed to stand overnight.

The reaction mixture was then diluted with ethyl acetate and poured on water. The aqueous phase was extracted twice with ethyl acetate. The organic phase was extracted with water and with brine then they were combined, dried over magnesium sulfate, filtered and concentrated under vacuo to give 2-chloro-N-cyclopropyl-5-[1-[5-hydroxy-2-methyl-4-(trifluoromethyl)pyrazol-3-yl]pyrazol-4-yl]benzamide (171 mg) as a crude solid.

¹H NMR (400 MHz, CDCl₃) δ ppm 0.56-0.75 (m, 2H) 0.80-1.03 (m, 2H) 2.92-3.01 (m, 1H) 3.68 (s, 3H) 6.34-6.55 (m, 1H) 7.43 (d, 1H) 7.47-7.57 (m, 1H) 7.86 (d, 1H) 7.93 (s, 1H) 8.10 (s, 1H)

¹⁹F NMR (377 MHz, CDCl₃) δ ppm −56.22 (s, 1F)

Preparation of 2-chloro-N-(1-cyanocyclopropyl)-5-[1-[5-hydroxy-2-methyl-4-(trifluoromethyl)pyrazol-3-yl]pyrazol-4-yl]benzamide

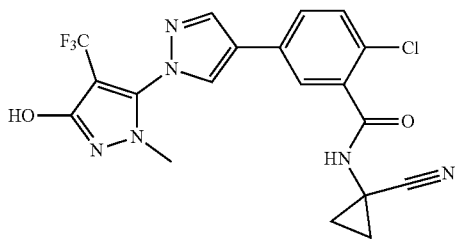 [SMILES: Cn1nc(O)c(C(F)(F)F)c1-n1cc(-c2ccc(Cl)c(C(=O)NC3(C#N)CC3)c2)cn1]

A mixture of 2-chloro-5-[1-[5-hydroxy-2-methyl-4-(trifluoromethyl)pyrazol-3-yl]pyrazol-4-yl]benzoic acid (300 mg, 0.698 mmol), 3-(ethyliminomethylideneamino)-N,N- dimethylpropan-1-amine; hydrochloride (150 mg, 0.768 mmol), 1-amino-1-cyano-cyclopropane-HCl (211 mg, 1.75 mmol) and 3-hydroxytriazolo[4,5-b]pyridine (107 mg, 0.768 mmol) in 10 ml of dichloromethane was stirred at room temperature. To this yellow solution was added 4-dimethylaminopyridine (215 mg, 1.75 mmol) and mixture was stirred overnight at room temperature until complete conversion. The mixture was diluted with dichloromethane, quenched with HCl 2N, the organic phase was washed successively with water and once with brine, dried over MgSO$_4$, filtrated and evaporated to give after a purification on silica gel 2-chloro-N-(1-cyanocyclopropyl)-5-[1-[5-hydroxy-2-methyl-4-(trifluoromethyl)pyrazol-3-yl]pyrazol-4-yl]benzamide as a white solid.

$^1$H NMR (400 MHz, CD$_3$OD) δ ppm 1.27-1.31 (m, 2H) 1.48-1.52 (m, 2H) 3.42 (s, 3H) 7.40 (d, 1H) 7.63-7.67 (m, 2H) 8.18 (d, 1H) 8.29 (s, 1H)

Similarly to the last two examples, the following compounds were prepared:

2-chloro-N-(1-cyanocyclopropyl)-5-[1-[5-hydroxy-2-methyl-4-(trifluoromethyl)pyrazol-3-yl]pyrazol-4-yl]-N-methyl-benzamide

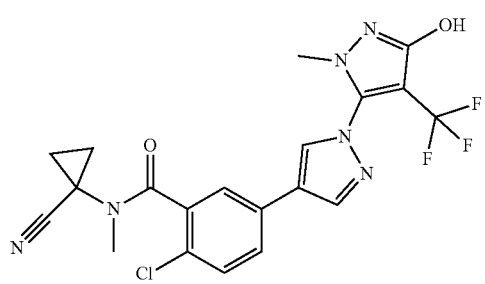 [SMILES: CN(C(=O)c1cc(-c2cnn(-c3c(C(F)(F)F)c(O)nn3C)c2)ccc1Cl)C1(C#N)CC1]

$^1$H NMR (400 MHz, CDCl$_3$) δ ppm 1.32-1.85 (m, 4H) 2.93-3.03 and 3.26 (2xm, 3H) 3.69 (m, 3H) 7.38-8.40 (m, 5H).

$^{19}$F NMR (377 MHz, CDCl$_3$) δ ppm −56.25−−56.20 (m, 3F)

2-chloro-N-cyclopropyl-5-[1-[5-hydroxy-2-methyl-4-(trifluoromethyl)pyrazol-3-yl]pyrazol-4-yl]-N-methyl-benzamide

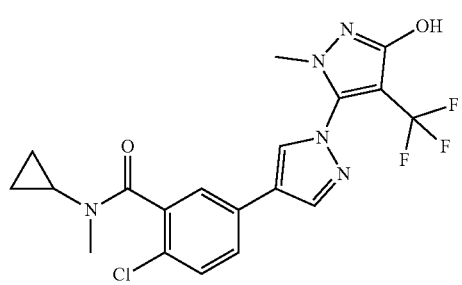 [SMILES: CN(C(=O)c1cc(-c2cnn(-c3c(C(F)(F)F)c(O)nn3C)c2)ccc1Cl)C1CC1]

$^1$H NMR (400 MHz, CDCl$_3$) δ ppm 0.45-1.05 (m, 4H) 2.74-2.84 and 2.94 (2xm, 2H) 3.16 and 3.50 (2xs, 3H) 3.69 (s, 3H) 7.41-7.52 (m, 3H) 7.90 (s, 1H) 8.08 (s, 1H)

19F NMR (377 MHz, CDCl$_3$) δ ppm −56.17 (s, 3F)

2-chloro-N-cyclopropyl-N-ethyl-5-[1-[5-hydroxy-2-methyl-4-(trifluoromethyl)pyrazol-3-yl]pyrazol-4-yl]benzamide

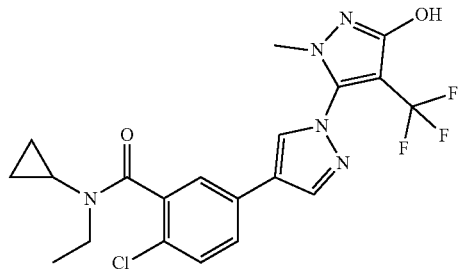 [SMILES: CCN(C(=O)c1cc(-c2cnn(-c3c(C(F)(F)F)c(O)nn3C)c2)ccc1Cl)C1CC1]

$^1$H NMR (400 MHz, CD$_3$OD) δ ppm 0.52-1.02 (m, 4H) 1.16-1.35 (m, 3H) 2.77-2.90 and 3.12-3.29 (2xm, 1H) 3.42-3.87 (m, 5H) 7.50 (m, 1H) 7.64-7.75 (m, 2H) 8.25-8.53 (m, 2H)

$^{19}$F NMR (377 MHz, CD$_3$OD) δ ppm −58.13 (s, 3F)

Example 1: Preparation of 5-[4-[4-chloro-3-[(1-cyanocyclopropyl)carbamoyl]phenyl]pyrazol-1-yl]-1-methyl-4-(trifluoromethyl)pyrazol-3-yl]1,1,2,2,2-pentafluoroethanesulfonate

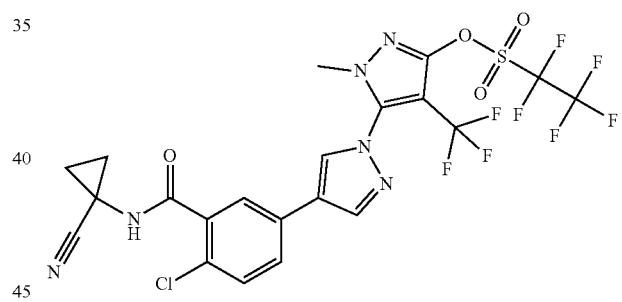

To a solution of 2-chloro-N-(1-cyanocyclopropyl)-5-[1-[5-hydroxy-2-methyl-4-(trifluoromethyl)pyrazol-3-yl]pyrazol-4-yl]benzamide (100 mg) in acetonitrile (0.88 mL) was added potassium carbonate (61 mg) followed by a dropwise addition of pentafluoroethanesulfonyl chloride (100 mg) at room temperature. The reaction mixture was stirred at room temperature for 1 hour and was then filtered. The resulting filtrate was concentrated under vacuo and purified on silica gel (eluant: cyclohexane/ethyl acetate, 6:4) to give 5-[4-[4-chloro-3-[(1-cyanocyclopropyl)carbamoyl]phenyl]pyrazol-1-yl]-1-methyl-4-(trifluoromethyl)pyrazol-3-yl]1,1,2,2,2-pentafluoroethanesulfonate.

1H NMR (400 MHz, CDCl$_3$) δ ppm 1.36-1.50 (m, 2H) 1.59-1.76 (m, 2H) 3.84 (s, 3H) 6.99 (bs, 1H) 7.46 (d, 1H) 7.56 (dd, 1H) 7.93 (d, 1H) 7.99 (s, 1H) 8.15 (s, 1H)

19F NMR (377 MHz, CDCl$_3$) δ ppm −112.42 (s, 2F) −79.06 (s, 3F) −56.13 (s, 3F),

Preparation of methyl 2-chloro-5-(1-tetrahydropyran-2-ylpyrazol-4-yl)benzoate

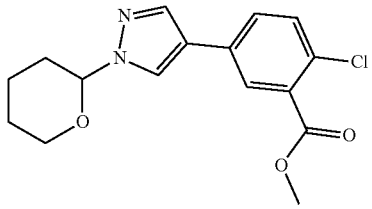 [SMILES: COC(=O)c1cc(-c2cnn(C3CCCCO3)c2)ccc1Cl]

To a solution of 4-bromo-1-tetrahydropyran-2-yl-pyrazole (0.108 g) in isopropanol (7 mL) was added methyl 2-chloro-5-(4,4,5,5-tetramethyl-1,3,2-dioxaborolan-2-yl) benzoate (0.1386 g) and an aqueous solution of sodium bicarbonate (1M, 1.4 mL). The reaction mixture was degassed with argon and then tetrakis(triphenylphosphine) palladium (0) was added (16.2 mg). The reaction mixture was then heated to 100° C. for 4 hours and cooled down to room temperature. The reaction mixture was partitioned between water and AcOEt. The aqueous phase was extracted with AcOEt twice, the combined organic layers were dried on $Na_2SO_4$ and concentrated under vacuum. The crude material was purified by flash chromatography (Cyclohexane/AcOEt) to give methyl 2-chloro-5-(1-tetrahydropyran-2-ylpyrazol-4-yl)benzoate as a colourless oil.

1H NMR (400 MHz, $CDCl_3$) ☐ ppm 1.58-1.79 (m, 4H) 2.09-2.18 (m, 2H) 3.68-3.79 (m, 1H) 3.95 (s, 3H) 4.05-4.15 (m, 1H) 5.38-5.44 (m, 1H) 7.43 (d, 1H) 7.52 (dd, 1H) 7.82 (s, 1H) 7.90 (s, 1H) 7.93 (d, 1H).

Preparation of methyl 2-chloro-5-(1H-pyrazol-4-yl)benzoate

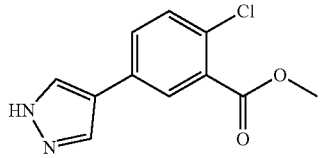

To a solution of methyl 2-chloro-5-(1-tetrahydropyran-2-ylpyrazol-4-yl)benzoate (2.5 g) in tetrahydrofuran (31 mL) was added concentrated hydrochloric acid (36% in water, 2.3 mL). The reaction mixture was stirred at 55° C. for 30 minutes and cooled down to room temperature. The reaction mixture was diluted with AcOEt, washed with saturated aqueous $NaHCO_3$ and with brine. The combined organic layers were dried over $Na_2SO_4$ and concentrated under vacuum. The crude material was purified by flash chromatography (Cyclohexane/AcOEt) to give methyl 2-chloro-5-(1H-pyrazol-4-yl)benzoate as a white solid.

1H NMR (400 MHz, $CDCl_3$) ☐ ppm 3.97 (s, 3H) 7.45 (d, 1H) 7.55 (dd, 1H) 7.90 (s, 2H) 7.96 (d, 1H).

Preparation of 2-chloro-5-(1H-pyrazol-4-yl)benzoic acid

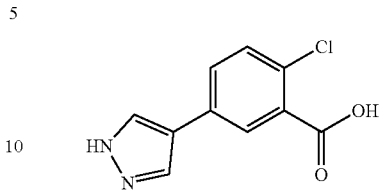

Methyl 2-chloro-5-(1H-pyrazol-4-yl)benzoate (2 g) was dissolved in dioxane (10 ml) and water (4 ml). NaOH pellets (0.372 g) were added at r.t. and the reaction mixture was stirred overnight at r.t. The reaction mixture was then concentrated under vacuum and diluted with some water. This basic solution was washed with methyl tert-butyl ether and was then acidified with HCl 1N. Precipitation of 2-chloro-5-(1H-pyrazol-4-yl)benzoic acid occurred. The solid was rinsed with water and dried on the filter. The solid was redissolved in $CH_2Cl_2$/methanol and dried on $MgSO_4$. The solution was then concentrated under vacuum to give 2-chloro-5-(1H-pyrazol-4-yl)benzoic acid as white crystals. Melting point: 227-229° C.

Preparation of 2-chloro-N-cyclopropyl-5-(1H-pyrazol-4-yl)benzamide

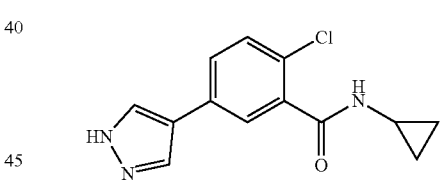

2-Chloro-5-(1H-pyrazol-4-yl)benzoic acid (825 mg) was dissolved in DMA (3 mL). Then cyclopropylamine (0.280 mL), Hünig's base (1.59 mL) were added at r.t. and the reaction mixture was stirred at r.t. for 10 minutes. The mixture was cooled down with an icebath and BOP-Cl (1.037 g) was added in 1 portion. The icebath was removed and the light suspension stirred for 8h at 55° C. then at r.t. overnight. As the reaction was not completed, cyclopropylamine (0.127 mL), Huenig's base (0.318 mL) and BOP-Cl (0.471 g) were added and the reaction mixture was heated again to 55° C. for 6 hours. The reaction mixture was poured into water. The precipitation of white crystals occurred.

After stirring for 10 minutes, the solid was filtered off and dried on filter. It was triturated in petrol ether to provide 2-chloro-N-cyclopropyl-5-(1H-pyrazol-4-yl)benzamide as white crystals.

Melting point: 102-103° C.

Preparation of 5-methoxy-2-methyl-4-(trifluoromethyl)pyrazole-3-carbonitrile

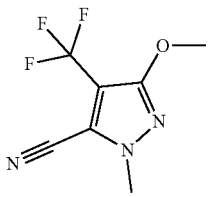

5-fluoro-3-methoxy-1-methyl-4-(trifluoromethyl)pyrazole (20.0 g) and potassium cyanide (19.7 g) were dissolved in MeCN (150 ml) and the mixture was heated under reflux for 16 h. After cooling, the precipitate was filtered off and concentrated. Column chromatography afforded title compound as colorless oil (13.2 g). $^1$H NMR (400 MHz, CDCl$_3$) δ 3.98 (s, 3H), 3.94 (s, 3H). $^{19}$F NMR (283 MHz, CDCl$_3$) δ −55.95 (s, 3F).

Preparation of 5-methoxy-2-methyl-4-(trifluoromethyl)pyrazole-3-carbaldehyde

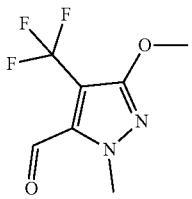

A solution of diisobutylaluminum hydride in toluene (1.5 M, 42 mL) was added into a chilled (−40° C.) solution of 5-methoxy-2-methyl-4-(trifluoromethyl)pyrazole-3-carbonitrile (13.0 g) in toluene (100 mL). After 10 min the cooling bath was removed and the reaction was stirred at room temperature for 2 h followed by careful addition of 2 N HCl (40 mL). The mixture was stirred at room temperature for 45 min then poured into water and extracted with ethyl acetate three times, the organic combined phases were dried over sodium sulfate and concentrated. Column chromatography afforded title compound as yellow oil (7.6 g).

Preparation of (3E)-5-methoxy-2-methyl-4-(trifluoromethyl)pyrazole-3-carbaldehyde oxime

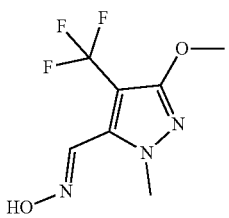

To a solution of 5-methoxy-2-methyl-4-(trifluoromethyl)pyrazole-3-carbaldehyde (7.2 g) in ethanol (80 mL) was added sodium bicarbonate (8.72 g) and hydroxylamine hydrochloride (4.81 g). The mixture was stirred at room temperature for 4 h. The reaction mixture was poured into water. The resulting crystals were collected by filtration, washed with water and dried to obtain title compound as a white powder (6.4 g). $^1$H NMR (400 MHz, DMSO-d$^6$) δ12.23-12.22 (m, 1H), 8.11-7.62 (m, 2H), 3.99-3.51 (m, 6H). $^{19}$F NMR (283 MHz, DMSO-d$^6$) δ −52.63−−51.12 (m, 3F).

Preparation of (3Z)—N-hydroxy-5-methoxy-2-methyl-4-(trifluoromethyl)pyrazole-3-carboximidoyl chloride

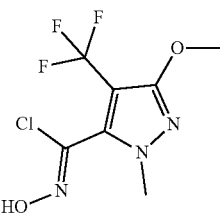 [SMILES: COc1nn(C)c(/C(Cl)=N/O)c1C(F)(F)F]

(3E)-5-methoxy-2-methyl-4-(trifluoromethyl)pyrazole-3-carbaldehyde oxime (6 g) was mixed N-Chlorosuccinimide (3.77 g) in DMF (40.0 mL) and stirred at room temperature for 2 h. The reaction mixture was poured into water and extracted with ethyl acetate two times. The combined organic layers were dried over sodium sulfate, filtered and concentrated under vacuum to give title compound as yellow oil (6.2 g). $^1$H NMR (400 MHz, DMSO-d$^6$) δ 13.34 (s, 1H), 3.90 (s, 3H), 3.73 (s, 3H). $^{19}$F NMR (283 MHz, DMSO-d$^6$) δ −52.48 (s, 3F).

Preparation of methyl 2-chloro-5-[3-[5-methoxy-2-methyl-4-(trifluoromethyl)pyrazol-3-yl]isoxazol-5-yl]benzoate

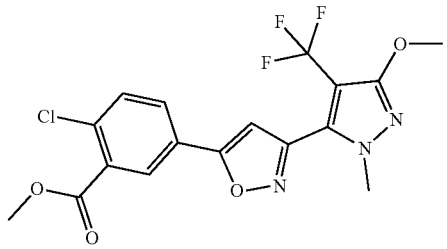

To a solution of (3E)-5-methoxy-2-methyl-4-(trifluoromethyl)pyrazole-3-carbaldehyde oxime (5.7 g) and methyl 2-chloro-5-ethynyl-benzoate (5.47 g) in dichloromethane (60 mL) was added triethylamine (5.17 g). The mixture was stirred at room temperature for 16 h. The reaction mixture was poured into water and extracted with dichloromethane twice, the combined organic layers were dried over sodium sulfate and concentrated. Column chromatography afforded title compound as a white solid (4.5 g). $^1$H NMR (400 MHz, CDCl$_3$) δ 8.28 (s, 1H), 7.88 (d, J=8.0 Hz, 1H), 7.61 (d, J=8.4 Hz, 1H), 6.78 (s, 1H), 4.00 (d, J=3.5 Hz, 6H), 3.89 (s, 3H). $^{19}$F NMR (283 MHz, CDCl$_3$) δ −34.42 (s, 3F).

Preparation of 2-chloro-5-[3-[5-methoxy-2-methyl-4-(trifluoromethyl)pyrazol-3-yl]isoxazol-5-yl]benzoic acid

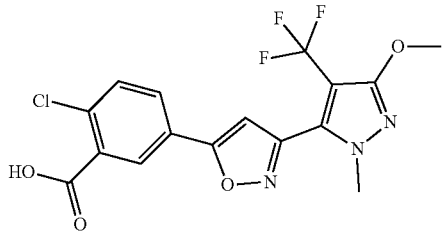 [SMILES: COc1nn(C)c(-c2cc(-c3ccc(Cl)c(C(=O)O)c3)on2)c1C(F)(F)F]

To a stirred solution of methyl 2-chloro-5-[3-[5-methoxy-2-methyl-4-(trifluoromethyl)pyrazol-3-yl]isoxazol-5-yl]benzoate (2.1 g) in THF (10 mL) was added sodium hydroxide (77 mg) and water (3 mL). The reaction mixture was stirred at room temperature for 2 h. The pH value was adjusted to 2 with concentrated HCl. The reaction mixture was extracted with ethyl acetate three times. The organic layers were dried over anhydrous sodium sulfate. After filtration and concentrated under vacuum title compound was obtained as a yellow powder (2.1 g).

Preparation of 2-chloro-5-[3-[5-hydroxy-2-methyl-4-(trifluoromethyl)pyrazol-3-yl]isoxazol-5-yl]benzoic acid

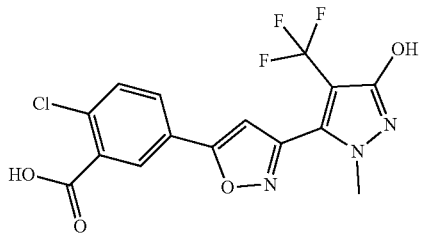 [SMILES: Cn1nc(O)c(C(F)(F)F)c1-c1cc(-c2ccc(Cl)c(C(=O)O)c2)on1]

To 20 ml of a 33 wt. % hydrogen bromide acetic acid solution was added 2-chloro-5-[3-[5-methoxy-2-methyl-4-(trifluoromethyl)pyrazol-3-yl]isoxazol-5-yl]benzoic acid (1.8 g). The mixture was stirred at 60° C. for 12 h. The reaction mixture was poured into water. The resulting crystals were collected by filtration, washed with water and dried to obtain title compound as a grey powder (1.6 g). $^1$H NMR (400 MHz, DMSO-d$^6$) δ 13.77 (s, 1H), 11.19 (s, 1H), 8.34 (s, 1H), 8.10 (d, J=8.3 Hz, 1H), 7.78 (d, J=8.3 Hz, 1H), 7.58 (s, 1H), 3.71 (s, 3H). $^{19}$F NMR (283 MHz, DMSO-d$^6$) δ −61.33 (s, 3F).

Preparation of 2-chloro-N-(1-cyanocyclopropyl)-5-[3-[5-hydroxy-2-methyl-4-(trifluoromethyl)pyrazol-3-yl]isoxazol-5-yl]-N-methyl-benzamide

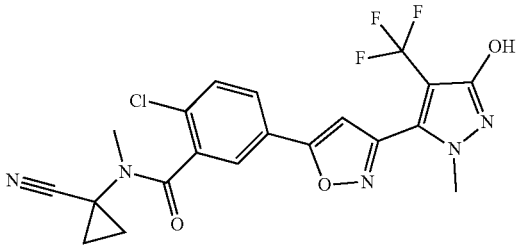 [SMILES: CN(C(=O)c1cc(-c2cc(-c3c(C(F)(F)F)c(O)nn3C)no2)ccc1Cl)C1(C#N)CC1]

To a stirred solution of 2-chloro-5-[3-[5-hydroxy-2-methyl-4-(trifluoromethyl)pyrazol-3-yl]isoxazol-5-yl]benzoic acid (0.300 g), 1-(methylamino)cyclopropanecarbonitrile hydrochloride (0.154 g) and HATU (0.441 g) in DMF (10 mL) was added N,N-Diisopropylethylamine (0.300 g). The mixture was stirred at room temperature for 16 h. The reaction mixture was poured into water and extracted with ethyl acetate twice. The combined organic layers were dried over sodium sulfate and concentrated. Column chromatography afforded title product as a white powder (0.14 g). $^1$H NMR (400 MHz, DMSO-d$^6$) δ 11.19 (s, 1H), 8.07 (m, 2H), 7.78 (m, 1H), 7.53 (s, 1H), 3.70 (s, 3H), 2.86 (s, 3H), 1.69 (m, 2H), 1.52 (m, 2H). $^{19}$F NMR (283 MHz, DMSO-d$^6$) δ −61.52 (d, J=15.6 Hz, 3F).

Example 37: Preparation of [5-[5-[4-chloro-3-[(1-cyanocyclopropyl)-methyl-carbamoyl]phenyl]isoxazol-3-yl]-1-methyl-4-(trifluoromethyl)pyrazol-3-yl] 1,1,1,2,3,3,3-heptafluoropropane-2-sulfonate

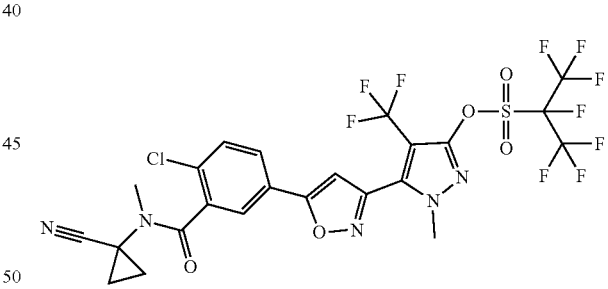

To a stirred solution of 2-chloro-N-(1-cyanocyclopropyl)-5-[3-[5-hydroxy-2-methyl-4-(trifluoromethyl)pyrazol-3-yl]isoxazol-5-yl]-N-methyl-benzamide (0.100 g) and potassium carbonate (0.0890 g) in tetrahydrofuran (15 mL) was added 1,1,1,2,3,3,3-heptafluoropropane-2-sulfonyl fluoride (0.108 g). Then the reaction was stirred at 70° C. for 24 hours. The reaction mixture were poured into water and extracted with ethyl acetate twice. The combined organic phases were dried over sodium sulfate and concentrated. Column chromatography afforded title product as a yellow oil (0.08 g). $^1$H NMR (400 MHz, CDCl$_3$) δ 7.99-7.82 (m, 2H), 7.70-7.52 (m, 1H), 6.88 (d, J=23.6 Hz, 1H), 4.07 (s, 3H), 3.26-2.98 (m, 3H), 1.50 (m, 2H), 1.37 (m, 2H). $^{19}$F NMR (283 MHz, CDCl$_3$) δ −64.00 (d, J=32.0 Hz, 3F), −80.32 (d, J=6.4 Hz, 6F), −175.06 (s, 1F).

Preparation of
1,1,1,2,3,3,3-heptafluoropropane-2-sulfonyl fluoride

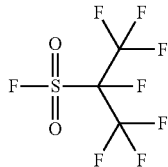

To a solution of KF (4.6 g) in 40 ml of sulfolane in a 250 mL steel autoclave, sulphuryl fluoride (51 g) and perfluoropropene (57.6 g) were loaded below −100° C. After the addition the reaction mixture was heated to 140° C. for about 4h. Subsequently the reaction mixture was cooled and distilled at atmospheric pressure. Title compound (43 g) was obtained within the boiling range of 0~39° C. as a colorless liquid. $^{19}$F NMR (282Mz, CDCl$_3$): δ 46.2 (d, J=5.6 Hz, 1F), −81.1 (m, 6F), −176.1 (d, J=7.8 Hz, 1F).

The following compounds in Table 1 were prepared in analogy with Example 1 and 37.

TABLE 1

Examples of compounds of formula (I)

| Ex. No. | Structure | NMR data |
|---|---|---|
| 2 | 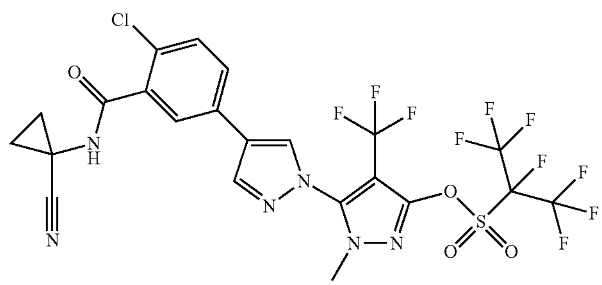 [SMILES: Cn1nc(OS(=O)(=O)C(F)(C(F)(F)F)C(F)(F)F)c(C(F)(F)F)c1-n1cc(-c2ccc(Cl)c(C(=O)NC3(C#N)CC3)c2)cn1] | 1H NMR (400 MHz, CD3OD) δ ppm 1.32-1.45 (m, 2 H) 1.53-1.69 (m, 2 H) 3.79 (s, 3 H) 7.53 (d, 1 H) 7.74-7.83 (m, 2 H) 8.37 (d, 1 H) 8.51 (s, 1 H) 19F NMR (377 MHz, CD3OD) δ ppm −166.93 (s, 1 F) −72.85 (s, 6 F) −58.02 (s, 3 F) |
| 3 | 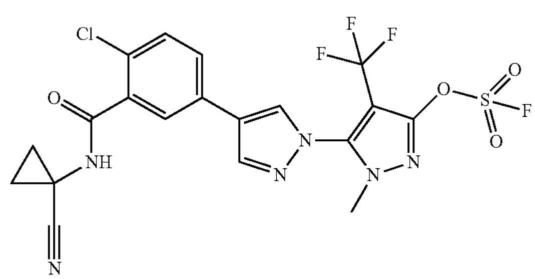 [SMILES: Cn1nc(OS(=O)(=O)F)c(C(F)(F)F)c1-n1cc(-c2ccc(Cl)c(C(=O)NC3(C#N)CC3)c2)cn1] | 1H NMR (400 MHz, CD3OD) δ ppm 1.32-1.45 (m, 2 H) 1.53-1.69 (m, 2 H) 3.79 (s, 3 H) 7.53 (d, 1 H) 7.74-7.83 (m, 2 H) 8.37 (d, 1 H) 8.51 (s, 1 H) 19F NMR (377 MHz, CD3OD) δ ppm −166.93 (s, 1 F) −72.85 (s, 6 F) −58.02 (s, 3 F) |
| 4 | 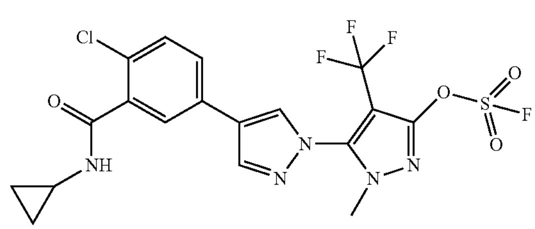 [SMILES: Cn1nc(OS(=O)(=O)F)c(C(F)(F)F)c1-n1cc(-c2ccc(Cl)c(C(=O)NC3CC3)c2)cn1] | 1H NMR (400 MHz, CDCl3) δ ppm 0.61-0.73 (m, 2 H) 0.84-0.96 (m, 2 H) 2.85-3.02 (m, 1 H) 3.85 (s, 3 H) 6.35-6.57 (m, 1 H) 7.44 (d, 1 H) 7.49-7.52 (m, 1 H) 7.85 (d, 1 H) 7.95 (s, 1 H) 8.14 (s, 1 H) 19F NMR (377 MHz, CDCl3) δ ppm −56.34 (s, 3 F) 43.00 (s, 1 F) |
| 5 | 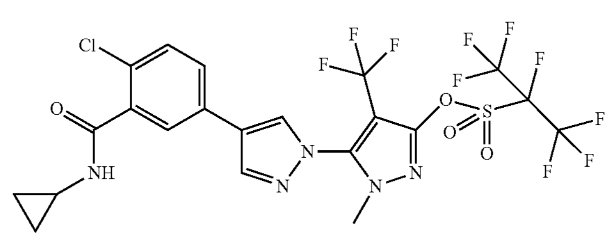 [SMILES: Cn1nc(OS(=O)(=O)C(F)(C(F)(F)F)C(F)(F)F)c(C(F)(F)F)c1-n1cc(-c2ccc(Cl)c(C(=O)NC3CC3)c2)cn1] | 1H NMR (400 MHz, CDCl3) δ ppm 0.61-0.77 (m, 2 H) 0.85-0.98 (m, 2 H) 2.93-2.97 (m, 1 H) 3.83 (s, 3 H) 6.44 (br s, 1 H) 7.36-7.46 (m, 1 H) 7.47-7.57 (m, 1 H) 7.85 (d, 1 H) 7.95 (s, 1 H) 8.07-8.18 (m, 1 H) 19F NMR (377 MHz, CDCl3) δ ppm −165.91 (m, 1 F) −71.27 (s, 6 F) −56.21 (s, 3 F) |

TABLE 1-continued

Examples of compounds of formula (I)

| Ex. No. | Structure | NMR data |
|---|---|---|
| 6 | 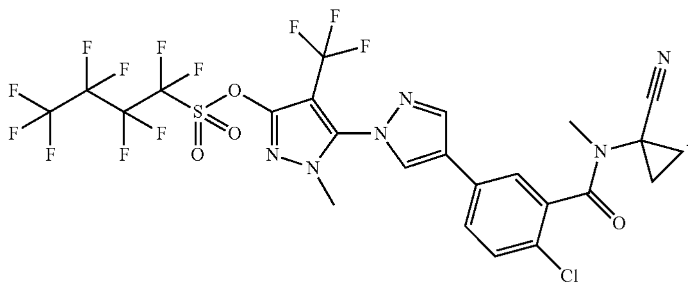 | 1H NMR (400 MHz, CD3OD) δ ppm 1.24-1.75 (m, 4 H) 2.98 and 3.24 (2xs, 3 H) 3.79 (s, 3 H) 7.51-7.64 (m, 1 H) 7.71-7.83 (m, 2 H) 7.92 (d, 1 H) 8.38 (s, 1 H) 8.48-8.56 (m, 1 H) 19F NMR (377 MHz, CD3OD) δ ppm −127.03 (s, 2 F) −121.87 (s, 2 F) −109.14 (s, 2 F) −82.26 (s, 3 F) −57.93 (s, 3 F) |
| 7 | 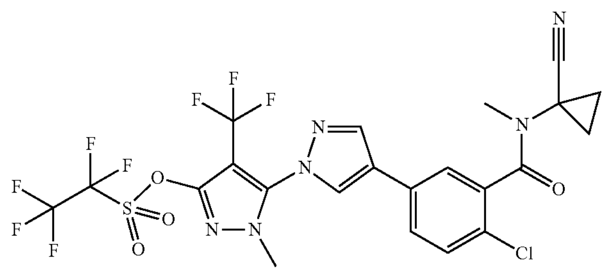 [SMILES: CN(C(=O)c1cc(-c2cnn(-c3c(C(F)(F)F)c(OS(=O)(=O)C(F)(F)C(F)(F)F)nn3C)c2)ccc1Cl)C1(C#N)CC1] | 1H NMR (400 MHz, CD3OD) δ ppm 1.48-1.75 (m, 4 H) 2.98 and 3.23 (2xs, 3 H) 3.79 (s, 3 H) 7.52-7.62 (m, 1 H) 7.69-7.96 (m, 2 H) 8.38 (s, 1 H) 8.47-8.56 (m, 1 H) 19F NMR (377 MHz, CD3OD) δ ppm −113.93 (s, 2 F) −80.86 (s, 3 F) −57.96 (s, 3 F) |
| 8 | 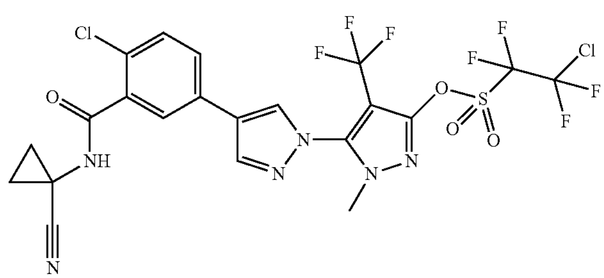 [SMILES: Cn1nc(OS(=O)(=O)C(F)(F)C(F)(F)Cl)c(C(F)(F)F)c1-n1cc(-c2ccc(Cl)c(C(=O)NC3(C#N)CC3)c2)cn1] | 1H NMR (400 MHz, CD3OD) δ ppm 1.32-1.44 (m, 2 H) 1.56-1.65 (m, 2 H) 3.79 (s, 3 H) 7.53 (d, 1 H) 7.72-7.82 (m, 2 H) 8.37 (s, 1 H) 8.51 (s, 1 H) 19F NMR (377 MHz, CD3OD) δ ppm −108.32 (s, 2 F) −68.43 (s, 2 F) −57.94 (s, 3 F) |
| 9 | 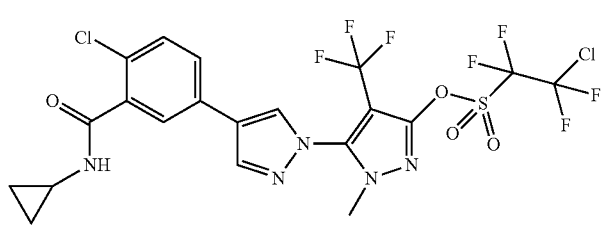 [SMILES: Cn1nc(OS(=O)(=O)C(F)(F)C(F)(F)Cl)c(C(F)(F)F)c1-n1cc(-c2ccc(Cl)c(C(=O)NC3CC3)c2)cn1] | 1H NMR (400 MHz, CD3OD) δ ppm 0.57-0.72 (m, 2 H) 0.76-0.89 (m, 2 H) 2.88 (m, 1 H) 3.79 (s, 3 H) 7.50 (d, 1 H) 7.70-7.77 (m, 2 H) 8.36 (s, 1 H) 8.49 (s, 1 H) 19F NMR (377 MHz, CD3OD) δ ppm −108.32 (s, 2 F) −68.43 (s, 2 F) −57.95 (s, 3 F) |
| 10 | 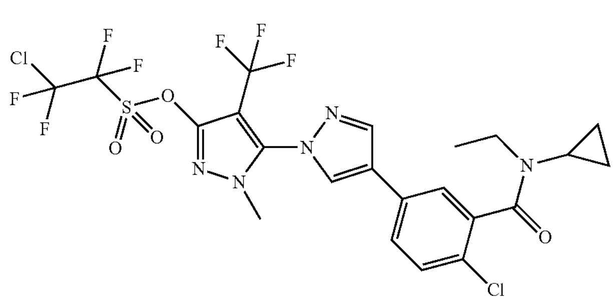 [SMILES: CCN(C(=O)c1cc(-c2cnn(-c3c(C(F)(F)F)c(OS(=O)(=O)C(F)(F)C(F)(F)Cl)nn3C)c2)ccc1Cl)C1CC1] | 1H NMR (400 MHz, CD3OD) δ ppm 0.56-0.97 (m, 4 H) 1.15-1.35 (m, 3 H) 2.74-2.91 (m, 1 H) 3.12-3.28 and 3.39-3.59 (m, 2 H) 3.79 (s, 3 H) 7.51 (d, 1 H) 7.64-7.79 (m, 2 H) 8.37 (s, 1 H) 8.51 (s, 1 H) 19F NMR (377 MHz, CD3OD) δ ppm −108.32 (s, 2 F) −68.43 (s, 2 F) −57.93 (s, 3 F) |

TABLE 1-continued

Examples of compounds of formula (I)

| Ex. No. | Structure | NMR data |
|---|---|---|
| 11 | 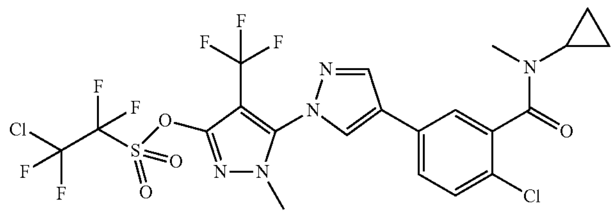 [SMILES: CN(C(=O)c1cc(-c2cnn(-c3c(C(F)(F)F)c(OS(=O)(=O)C(F)(F)C(F)(F)Cl)nn3C)c2)ccc1Cl)C1CC1] | 1H NMR (400 MHz, CD3OD) δ ppm 0.45-1.01 (m, 4 H) 2.76-2.98 (m, 1 H) 2.87 and 3.14 (2xs, 3 H) 3.79 (s, 3 H) 7.52 (d, 1 H) 7.62-7.77 (m, 2 H) 8.37 (d, 1 H) 8.50 (s, 1 H) 19F NMR (377 MHz, CD3OD) δ ppm −108.32 (s, 2 F) −68.43 (s, 2 F) −57.93 (s, 3 F) |
| 12 | 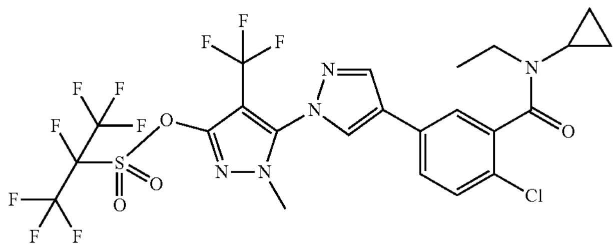 [SMILES: CCN(C(=O)c1cc(-c2cnn(-c3c(C(F)(F)F)c(OS(=O)(=O)C(F)(C(F)(F)F)C(F)(F)F)nn3C)c2)ccc1Cl)C1CC1] | 1H NMR (400 MHz, CD3OD) δ ppm 0.49-1.04 (m, 4 H) 1.12-1.37 (m, 3 H) 2.71-2.90 (m, 1 H) 3.07-3.28 and 3.39-3.58 (m, 2 H) 3.79 (s, 3 H) 7.51 (d, 1 H) 7.63-7.77 (m, 2 H) 8.37 (s, 1 H) 8.52 (s, 1 H) 19F NMR (377 MHz, CD3OD) δ ppm −166.90 (s, 1 F) −72.87 (s, 6 F) −58.01 (s, 3 F) |
| 13 | 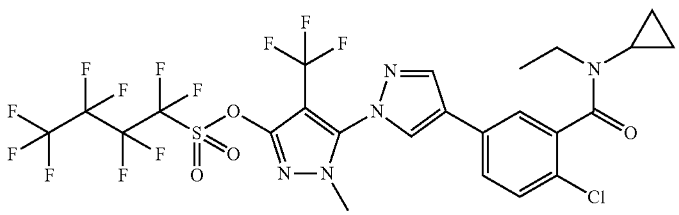 [SMILES: CCN(C(=O)c1cc(-c2cnn(-c3c(C(F)(F)F)c(OS(=O)(=O)C(F)(F)C(F)(F)C(F)(F)C(F)(F)F)nn3C)c2)ccc1Cl)C1CC1] | 1H NMR (400 MHz, CD3OD) δ ppm 0.52-1.03 (m, 4 H) 1.11-1.33 (m, 3 H) 2.81-2.90 (m, 1 H) 3.12-3.27 and 3.40-3.60 (m, 2 H) 3.79 (s, 3 H) 7.51 (d, 1 H) 7.63-7.77 (m, 2 H) 8.38 (s, 1 H) 8.51 (s, 1 H) F NMR (377 MHz, CD3OD) δ ppm −127.02 (s, 2 F) −121.88 (s, 2 F) −109.13 (s, 2 F) −82.26 (s, 3 F) −57.96 (s, 3 F) |
| 14 | 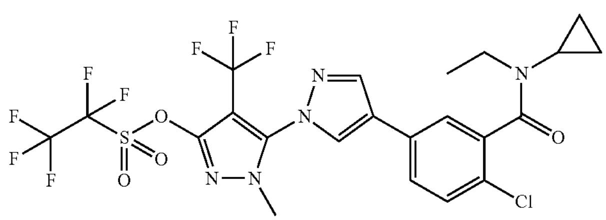 [SMILES: CCN(C(=O)c1cc(-c2cnn(-c3c(C(F)(F)F)c(OS(=O)(=O)C(F)(F)C(F)(F)F)nn3C)c2)ccc1Cl)C1CC1] | 1H NMR (400 MHz, CD3OD) δ ppm 0.49-0.90 (m, 4 H) 1.13-1.33 (m, 3 H) 2.72-2.92 (m, 1 H) 3.17-3.52 (m, 2 H) 3.79 (s, 3 H) 7.51 (d, 1 H) 7.64-7.78 (m, 2 H) 8.37 (s, 1 H) 8.51 (s, 1 H) 19F NMR (377 MHz, CD3OD) δ ppm −113.92 (s, 2 F) −80.85 (s, 3 F) −57.96 (s, 3 F) |
| 15 | 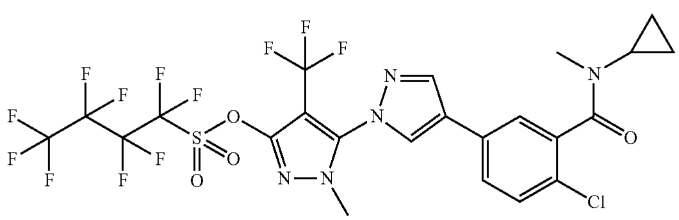 [SMILES: CN(C(=O)c1cc(-c2cnn(-c3c(C(F)(F)F)c(OS(=O)(=O)C(F)(F)C(F)(F)C(F)(F)C(F)(F)F)nn3C)c2)ccc1Cl)C1CC1] | 1H NMR (400 MHz, CD3OD) δ ppm 0.44-0.93 (m, 4 H) 2.82-2.92 (m, 1 H) 2.87 and 3.14 (2xs, 3 H) 3.75 and 3.80 (2xs, 3 H) 7.46-7.59 (m, 1 H) 7.64-7.79 (m, 2 H) 8.37 (s, 1 H) 8.49 (s, 1 H) 19F NMR (377 MHz, CD3OD) δ ppm −126.95 (s, 2 F) −121.81 (s, 2 F) −109.07 (s, 2 F) −82.25 (s, 3 F) −57.95 (s, 3 F) |
| 16 | 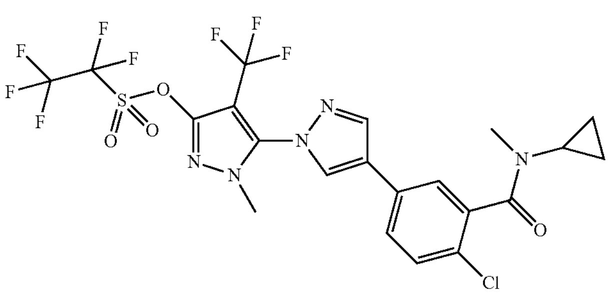 [SMILES: CN(C(=O)c1cc(-c2cnn(-c3c(C(F)(F)F)c(OS(=O)(=O)C(F)(F)C(F)(F)F)nn3C)c2)ccc1Cl)C1CC1] | 1H NMR (400 MHz, CD3OD) δ ppm 0.45-0.97 (m, 4 H) 2.78-2.95 (m, 1 H) 3.14 and 3.35 (2xs, 3 H) 3.80 (s, 3 H) 7.45-7.58 (m, 1 H) 7.62-7.77 (m, 2 H) 8.37 (s, 1 H) 8.50 (s, 1 H) 19F NMR (377 MHz, CD3OD) δ ppm −113.92 (s, 2 F) −80.85 (s, 3 F) −57.97 (s, 3 F) |

TABLE 1-continued

Examples of compounds of formula (I)

| Ex. No. | Structure | NMR data |
|---|---|---|
| 17 | 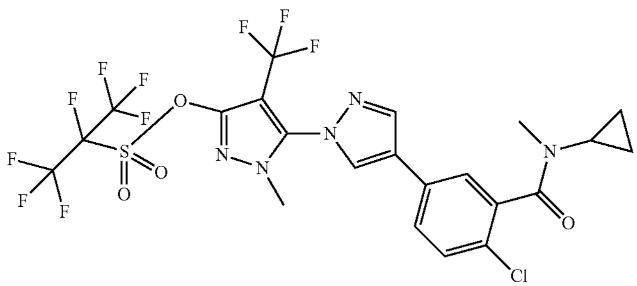 [SMILES: CN(C(=O)c1cc(-c2cnn(-c3c(C(F)(F)F)c(OS(=O)(=O)C(F)(C(F)(F)F)C(F)(F)F)nn3C)c2)ccc1Cl)C1CC1] | 1H NMR (400 MHz, CD3OD) δ ppm 0.45-1.01 (m, 4 H) 2.82-2.91 (m, 1 H) 2.87 and 3.14 (2xs, 3 H) 3.70-3.90 (m, 3 H) 7.47-7.57 (m, 1 H) 7.64-7.76 (m, 2 H) 8.37 (s, 1 H) 8.49 (s, 1 H) 19F NMR (377 MHz, CD3OD) δ ppm −166.87 (s, 1 F) −72.83 (s, 6 F) −58.01 (s, 3 F) |
| 18 | 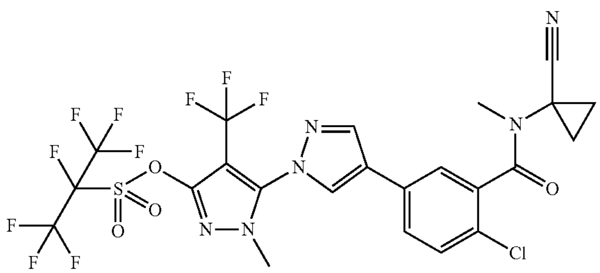 [SMILES: CN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | 1H NMR (400 MHz, CD3OD) δ ppm 1.28-1.80 (m, 4 H) 2.98 and 3.23 (2xs, 3 H) 3.79 (s, 3 H) 7.53-7.61 (m, 1 H) 7.68-7.96 (m, 2 H) 8.37 (s, 1 H) 8.49-8.50 (m, 1 H) 19F NMR (377 MHz, CD3OD) δ ppm −166.85 (s, 1 F) −72.85 (s, 6 F) −58.01 (s, 3 F) |
| 19 | 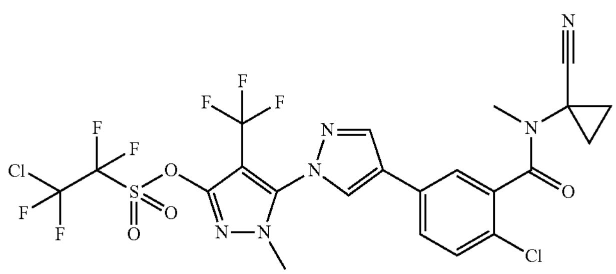 [SMILES: CN(C(=O)c1cc(-c2cnn(-c3c(C(F)(F)F)c(OS(=O)(=O)C(F)(F)C(F)(F)Cl)nn3C)c2)ccc1Cl)C1(C#N)CC1] | 1H NMR (400 MHz, CD3OD) δ ppm 1.48-1.76 (m, 4 H) 2.99 and 3.24 (2xs, 3 H) 3.77 (s, 3 H) 7.54-7.62 (m, 1 H) 7.73-7.93 (m, 2 H) 8.38 (s, 1 H) 8.50-8.52 (m, 1 H) 19F NMR (377 MHz, CD3OD) δ ppm −108.32 (s, 2 F) −68.43 (s, 2 F) −57.91-57.94 (m, 3 F) |
| 20 | 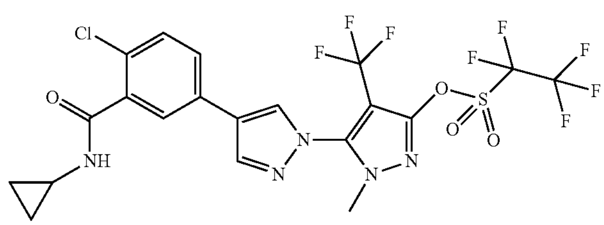 [SMILES: Cn1nc(OS(=O)(=O)C(F)(F)C(F)(F)F)c(C(F)(F)F)c1-n1cc(-c2ccc(Cl)c(C(=O)NC3CC3)c2)cn1] | 1H NMR (400 MHz, CD3OD) δ ppm 0.57-0.71 (m, 2 H) 0.76-0.87 (m, 2 H) 2.81-2.96 (m, 1 H) 3.77 (s, 3 H) 7.43-7.54 (m, 1 H) 7.66-7.77 (m, 2 H) 8.28-8.40 (m, 1 H) 8.45-8.57 (m, 1 H) 19F NMR (377 MHz, CD3OD) δ ppm −113.92 (s, 2 F) −80.86 (s, 3 F) −57.98 (s, 3 F) |
| 21 | 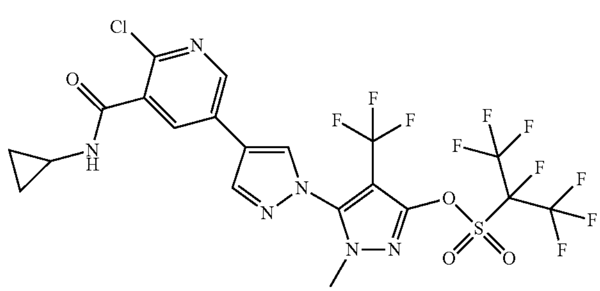 [SMILES: Cn1nc(OS(=O)(=O)C(F)(C(F)(F)F)C(F)(F)F)c(C(F)(F)F)c1-n1cc(-c2cnc(Cl)c(C(=O)NC3CC3)c2)cn1] | 1H NMR (400 MHz, cdcl3) δ 8.58 (s, 1H), 8.16 (s, 1H), 8.06 (s, 1H), 8.01 (s, 1H), 6.44 (s, 1H), 3.83 (s, 3H), 2.95 (s, 1H), 0.93 (d, J = 6.7 Hz, 2H), 0.71 (s, 2H). 19F NMR (283 MHz, CDCl3) δ −36.12 (s, 3F), −51.20 (s, 6F), −145.58 −145.90 (m, 1F). |

TABLE 1-continued

Examples of compounds of formula (I)

| Ex. No. | Structure | NMR data |
|---|---|---|
| 22 | 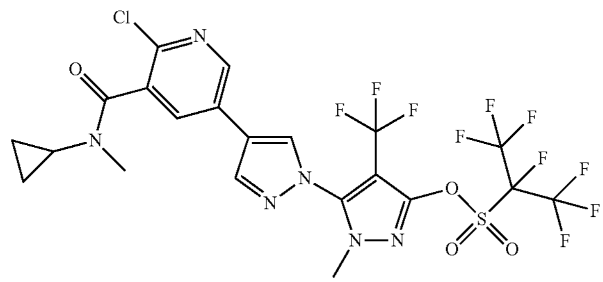 [SMILES: CN(C(=O)c1cc(-c2cnn(-c3c(C(F)(F)F)c(OS(=O)(=O)C(F)(C(F)(F)F)C(F)(F)F)nn3C)c2)cnc1Cl)C1CC1] | 1H NMR (400 MHz, dmso) δ 8.56(s, 1H), 8.14(s, 1H), 8.00 (s, 1H), 7.67 (s, 1H), 3.83 (s, 3H), 3.15(s, 3H), 2.88(s,1H), 0.87 (s, 2H), 0.61(s, 2H). 19F NMR (283 MHz, CDCl3) δ −36.12 (s, 3F), −51.23 (s, 6F), −145.81 (s, 1F). |
| 23 | 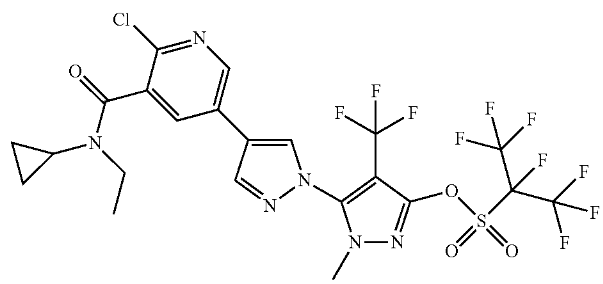 [SMILES: CCN(C(=O)c1cc(-c2cnn(-c3c(C(F)(F)F)c(OS(=O)(=O)C(F)(C(F)(F)F)C(F)(F)F)nn3C)c2)cnc1Cl)C1CC1] | 1H NMR (400 MHz, dmso) δ 8.55(s, 1H), 8.14(s, 1H), 7.99 (s, 1H), 7.65 (s, 1H), 3.83 (s, 3H), 3.28 (s, 2H), 2.84(s, 1H) 1.32(s, 3H), 0.87 (s, 2H), 0.62(s, 2H). 19F NMR (283 MHz, CDCl3) δ −64.32 (s, 3F), −79.42 (d, J = 7.6 Hz, 6F), −174.03 (s, 1F). |
| 24 | 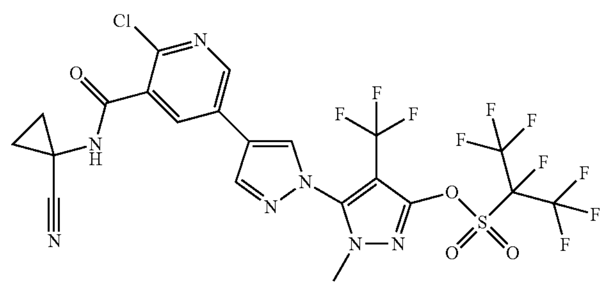 [SMILES: Cn1nc(OS(=O)(=O)C(F)(C(F)(F)F)C(F)(F)F)c(C(F)(F)F)c1-n1cc(-c2cnc(Cl)c(C(=O)NC3(C#N)CC3)c2)cn1] | 1H NMR (400 MHz, dmso) δ 8.63 (s, 1H), 8.18 (s, 1H), 8.14(s, 1H) 8.05 (s, 1H), 6.96 (s, 1H), 3.84(s, 3H), 2.01(s, 2H), 1.46 (s, 2H). 19F NMR (283 MHz, CDCl3) δ −64.30 (s, 3F), −79.38 (d, J = 7.5 Hz, 6F), −174.57 (s, 1F). |
| 25 | 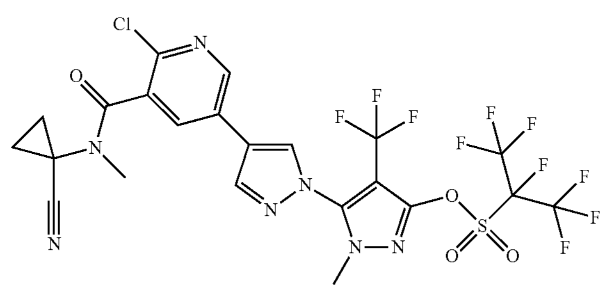 [SMILES: CN(C(=O)c1cc(-c2cnn(-c3c(C(F)(F)F)c(OS(=O)(=O)C(F)(C(F)(F)F)C(F)(F)F)nn3C)c2)cnc1Cl)C1(C#N)CC1] | 1H NMR (400 MHz, dmso) δ 8.97 (s, 1H), 8.90 (s, 1H), 8.68 (s, 1H), 8.29 (s, 1H), 3.81 (s, 3H), 2.91 (s, 3H), 1.73 (s, 2H), 1.23 (s, 2H). 19F NMR (283 MHz, CDCl3) δ −64.28 (d, J = 11.6 Hz, 3F), −79.48 (d, J = 7.3 Hz, 6F), −174.55 (s, 1F). |
| 26 | 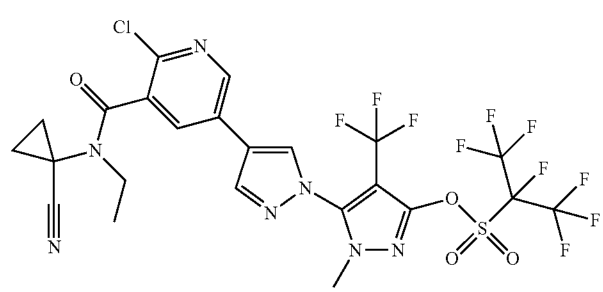 [SMILES: CCN(C(=O)c1cc(-c2cnn(-c3c(C(F)(F)F)c(OS(=O)(=O)C(F)(C(F)(F)F)C(F)(F)F)nn3C)c2)cnc1Cl)C1(C#N)CC1] | 1H NMR (400 MHz, dmso) δ 9.00 (s, 1H), 8.91 (s, 1H), 8.70 (s, 1H), 8.36 (s, 1H), 3.81 (s, 3H), 3.34 (s, 2H), 3.24 (d, J = 34.4 Hz, 2H), 1.77 (s, 2H), 1.46 (s, 2H), 1.23 (s, 3H). 19F NMR (283 MHz, CDCl3) δ −64.20 (s, 3F), −79.41 (d, J = 7.5 Hz, 6F), −174.49 (s, 1F). |

TABLE 1-continued

Examples of compounds of formula (I)

| Ex. No. | Structure | NMR data |
|---|---|---|
| 27 | 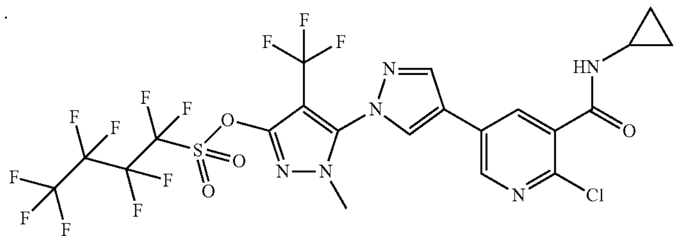 [SMILES: Cn1nc(OS(=O)(=O)C(F)(F)C(F)(F)C(F)(F)C(F)(F)F)c(C(F)(F)F)c1-n1cc(-c2cnc(Cl)c(C(=O)NC3CC3)c2)cn1] | ¹H NMR (400 MHz, cdcl₃) δ 8.57 (s, 1H), 8.16 (s, 1H), 8.04 (s, 1H), 8.02 (s, 1H), 6.47 (s, 1H), 3.83 (s, 3H), 2.94 (s, 1H), 0.92 (d, J = 6.9 Hz, 2H), 0.70 (s, 2H). 19F NMR (283 MHz, CDCl3) δ −54.30 (s, 3F), −78.79 (s, 3F), −105.78-106.15 (m, 2F), −118.71-119.08 (m, 2F), −123.74-124.12 (m, 2F) |
| 28 | 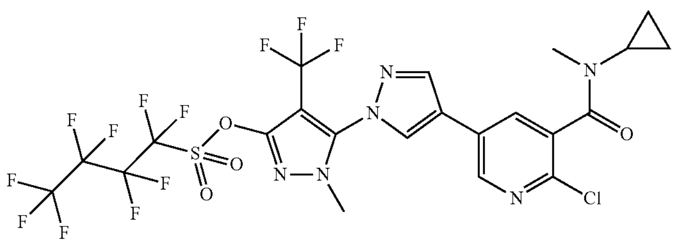 [SMILES: CN(C(=O)c1cc(-c2cnn(-c3c(C(F)(F)F)c(OS(=O)(=O)C(F)(F)C(F)(F)C(F)(F)C(F)(F)F)nn3C)c2)cnc1Cl)C1CC1] | 1H NMR (400 MHz, dmso) δ 8.56(s, 1H), 8.14(s, 1H), 8.00 (s, 1H), 7.67 (s, 1H), 3.83 (s, 3H), 3.15(s, 3H), 2.88(s, 1H), 1.60 (s, 2H), 1.25(s, 2H). 19F NMR (283 MHz, CDCl3) δ −64.09 (s, 3F), −88.58 (s, 3F), −115.74 (s, 2F), −128.65-129.07 (m, 2F), −133.73-134.21 (m, 2F). |
| 29 | 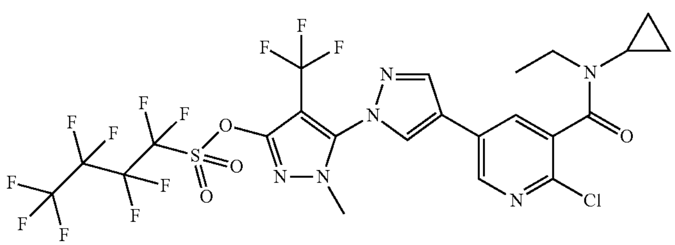 [SMILES: CCN(C(=O)c1cc(-c2cnn(-c3c(C(F)(F)F)c(OS(=O)(=O)C(F)(F)C(F)(F)C(F)(F)C(F)(F)F)nn3C)c2)cnc1Cl)C1CC1] | 1H NMR (400 MHz, dmso) δ 8.56 (s, 1H), 8.14(s, 1H), 8.00 (s, 1H), 7.65 (s, 1H), 3.84 (s, 3H), 3.35 (s, 3H), 2.85(s, 1H) 1.25(s, 3H), 0.87 (s, 2H), 0.62(s, 2H). 19F NMR (283 MHz, CDCl3) δ −64.21 (s, 3F), −88.70 (s, 3F), −115.77-116.00 (m, 2F), −128.70-129.00 (m, 2F), −133.79-134.13 (m, 2F). |
| 30 | 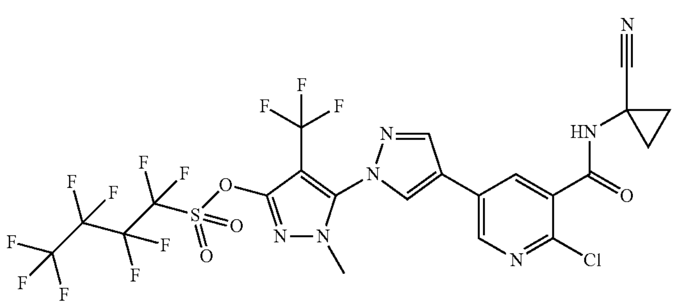 [SMILES: Cn1nc(OS(=O)(=O)C(F)(F)C(F)(F)C(F)(F)C(F)(F)F)c(C(F)(F)F)c1-n1cc(-c2cnc(Cl)c(C(=O)NC3(C#N)CC3)c2)cn1] | 1H NMR (400 MHz, dmso) δ 9.61 (s, 1H), 8.99 (s, 1H), 8.90 (s, 1H), 8.70 (s, 1H), 8.30(s,1H), 3.81 (s, 3H), 1.64 (s, 2H), 1.30 (s, 2H). 19F NMR (283 MHz, CDCl3) δ −64.03 (s, 3F), −88.36 (s, 3F), −116.37 (s, 2F), −128.97 (s, 2F), −133.76 (s, 2F) |
| 31 | 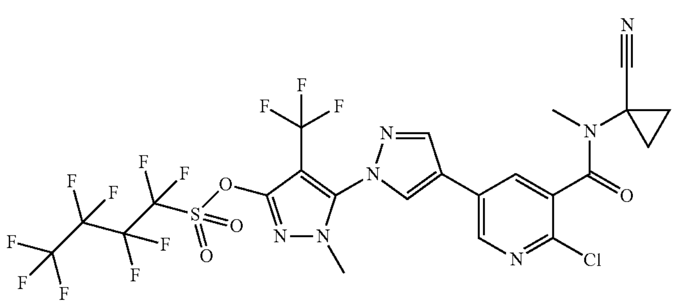 [SMILES: CN(C(=O)c1cc(-c2cnn(-c3c(C(F)(F)F)c(OS(=O)(=O)C(F)(F)C(F)(F)C(F)(F)C(F)(F)F)nn3C)c2)cnc1Cl)C1(C#N)CC1] | 1H NMR (400 MHz, dmso) δ 8.64(s, 1H), 8.21 (s, 1H), 8.08 (s, 1H), 8.00 (s, 1H), 3.83 (s, 3H), 3.25(s, 3H), 1.64 (s, 2H), 1.30 (s, 2H). 19F NMR (283 MHz, CDCl3) δ −54.30 (s, 3F), −78.79 (s, 3F), −105.78-106.15 (m, 2F), −118.71-119.08 (m, 2F), −123.74-124.12 (m, 2F). |

TABLE 1-continued

Examples of compounds of formula (I)

| Ex. No. | Structure | NMR data |
|---|---|---|
| 32 | 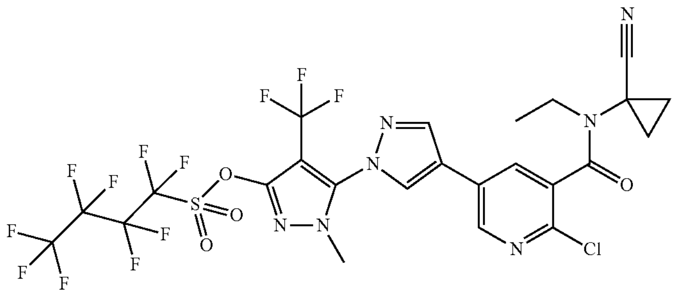 [SMILES: CCN(C(=O)c1cc(-c2cnn(-c3c(C(F)(F)F)c(OS(=O)(=O)C(F)(F)C(F)(F)C(F)(F)C(F)(F)F)nn3C)c2)cnc1Cl)C1(C#N)CC1] | ¹H NMR (400 MHz, dmso) δ 9.00 (s, 1H), 8.91 (s, 1H), 8.71 (s, 1H), 8.36(s, 1H), 3.82 (s, 3H), 3.11 (s, 2H), 1.77 (s, 2H), 1.34 (s, 2H), 1.24 (s, 3H). 19F NMR (283 MHz, CDCl3) δ −64.12 (s, 3F), 88.52 (t, J = 9.2 Hz, 3F), −116.50 (s, 2F), −129.09 (s,2F), −133.91 (s, 2F) |
| 33 | 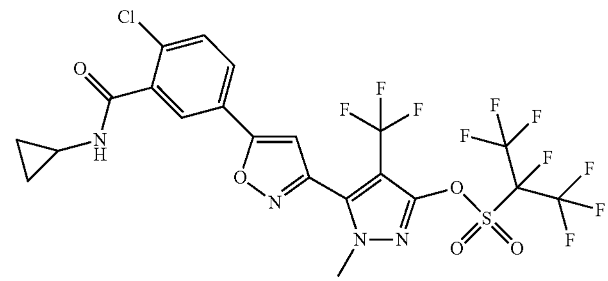 [SMILES: Cn1nc(OS(=O)(=O)C(F)(C(F)(F)F)C(F)(F)F)c(C(F)(F)F)c1-c1cc(-c2ccc(Cl)c(C(=O)NC3CC3)c2)on1] | 1H NMR (400 MHz, cdcl3) δ 8.12 (s, 1H), 7.84 (d, J = 8.0 Hz, 1H), 7.56 (d, J = 8.0 Hz, 1H), 6.83 (s, 1H), 6.39 (s, 1H), 4.06 (s, 3H), 2.97 (m, 1H), 0.93 (m, 2H), 0.70 (m, 2H). 19F NMR (283 MHz, CDCl3) δ −63.93 (s, 3F), −80.26 (d, J = 7.4 Hz, 6F), −175.02 (s, 1F). |
| 34 | 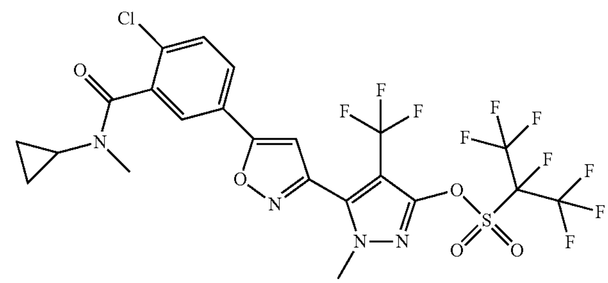 [SMILES: CN(C(=O)c1cc(-c2cc(-c3c(C(F)(F)F)c(OS(=O)(=O)C(F)(C(F)(F)F)C(F)(F)F)nn3C)no2)ccc1Cl)C1CC1] | 1H NMR (400 MHz, cdcl3) δ 7.83-7.72 (m, 2H), 7.56 (d, J = 8.1 Hz, 1H), 6.80 (s, 1H), 4.06 (s, 3H), 3.16 (s, 3H), 2.77 (m, 1H), 0.56 (m, 4H). 19F NMR (283 MHz, CDCl3) 63.22 (s, 3F), −79.57 (d, J = 7.1 Hz, 6F), −174.29 (s, 1F). |
| 35 | 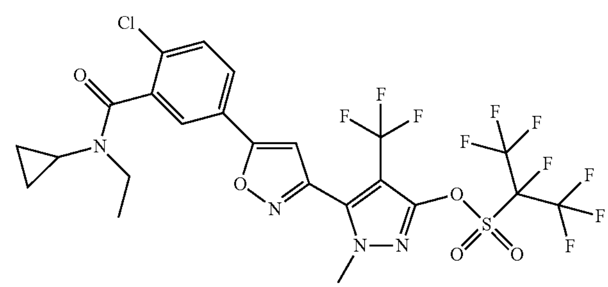 [SMILES: CCN(C(=O)c1cc(-c2cc(-c3c(C(F)(F)F)c(OS(=O)(=O)C(F)(C(F)(F)F)C(F)(F)F)nn3C)no2)ccc1Cl)C1CC1] | 1H NMR (301 MHz, CDCl3) δ 7.82-7.70 (m, 2H), 7.55 (d, J = 8.3 Hz, 1H), 6.80 (s, 1H), 4.06 (s, 3H), 3.61-3.10 (m, 2H), 2.77 (m, 1H), 1.33 (t, J = 7.1 Hz, 3H), 0.57 (m, 2H), 0.54 (m, 2H). 19F NMR (283 MHz, CDCl3) δ −55.36 (s, 3F), −71.70 (s, 6F), −166.42 (s, 1F). |
| 36 | 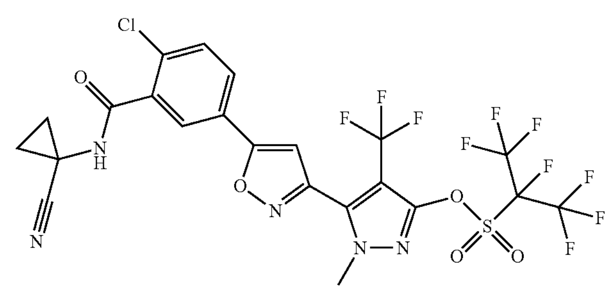 [SMILES: Cn1nc(OS(=O)(=O)C(F)(C(F)(F)F)C(F)(F)F)c(C(F)(F)F)c1-c1cc(-c2ccc(Cl)c(C(=O)NC3(C#N)CC3)c2)on1] | 1H NMR (400 MHz, cdcl3) δ 8.18 (s, 1H), 7.89 (d, J = 7.5 Hz, 1H), 7.58 (d, J = 8.0 Hz, 1H), 6.98 (s, 1H), 6.87 (s, 1H), 4.06 (s, 3H), 1.71 (m, 2H), 1.44 (m, 2H). 19F NMR (283 MHz, CDCl3) δ −63.84 (s, 3F), −80.19 (d, J = 7.2 Hz, 6F), −174.93 (s, 1F). |

TABLE 1-continued

Examples of compounds of formula (I)

| Ex. No. | Structure | NMR data |
|---|---|---|
| 38 | 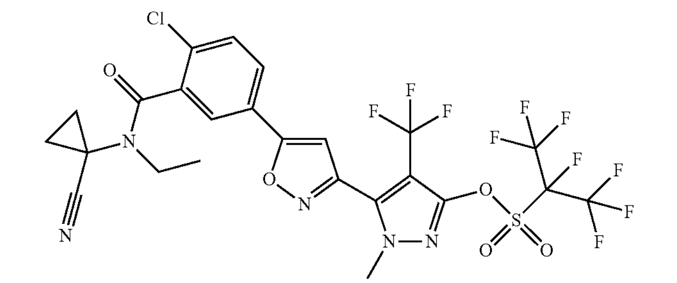 [SMILES: CCN(C(=O)c1cc(-c2cc(-c3c(C(F)(F)F)c(OS(=O)(=O)C(F)(C(F)(F)F)C(F)(F)F)nn3C)no2)ccc1Cl)C1(C#N)CC1] | 1H NMR (400 MHz, cdcl3) δ 8.02-7.77 (m, 2H), 7.66-7.57 (m, 1H), 6.88 (d, J = 23.6 Hz, 1H), 4.06 (s, 3H), 3.37 (m, 2H), 1.47 (s, 3H), 1.40 (m, 2H), 1.33 (m, 2H). 19F NMR (283 MHz, CDCl3) δ −64.20 (d, J = 32.5 Hz, 3F), −80.52 (s, 6F), −175.30 (s, 1F). |
| 39 | 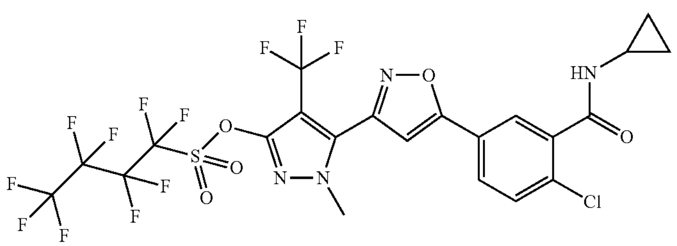 [SMILES: Cn1nc(OS(=O)(=O)C(F)(F)C(F)(F)C(F)(F)C(F)(F)F)c(C(F)(F)F)c1-c1cc(-c2ccc(Cl)c(C(=O)NC3CC3)c2)on1] | 1H NMR (400 MHz, dmso) δ 8.65 (s, 1H), 8.03 (m, 2H), 7.76-7.67 (m, 2H), 3.99 (s, 3H), 2.85 (t, 1H), 0.72 (d, 2H), 0.56 (d, 2H). 19F NMR (283 MHz, dmso) δ −62.65 (s, 3F), −88.47 (s, 3F), −122.90 (s, 2F), −129.46 (s, 2F), −133.71 (s, 2F). |
| 41 | 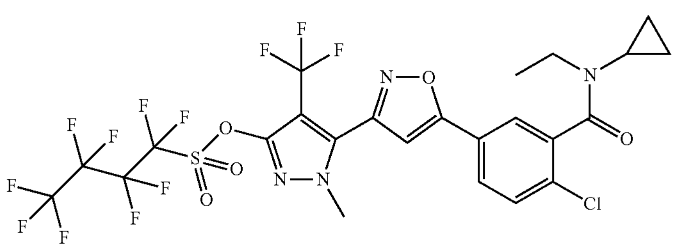 [SMILES: CCN(C(=O)c1cc(-c2cc(-c3c(C(F)(F)F)c(OS(=O)(=O)C(F)(F)C(F)(F)C(F)(F)C(F)(F)F)nn3C)no2)ccc1Cl)C1CC1] | 1H NMR (400 MHz, cdcl3) δ 7.83-7.67 (m, 2H), 7.55 (d, J = 8.4 Hz, 1H), 6.80 (s, 1H), 4.06 (s, 3H), 3.48 (m, 2H), 2.76 (m, 1H), 1.33 (t, J = 7.0 Hz, 3H), 0.57 (m, 4H). 19F NMR (283 MHz, CDCl3) δ −63.28 (s, 3F), −88.96 (d, J = 9.2 Hz, 3F), −116.22 (s, 2F), −129.09 (s, 2F), −134.15 (s, 2F). |
| 42 | 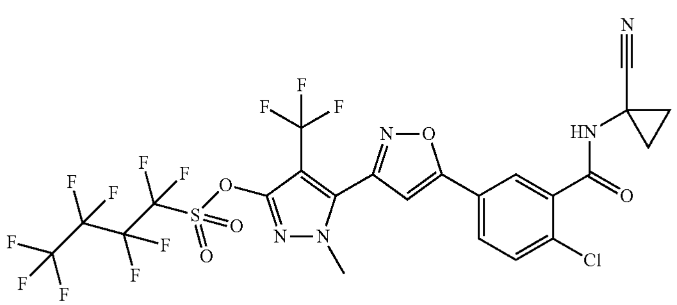 [SMILES: Cn1nc(OS(=O)(=O)C(F)(F)C(F)(F)C(F)(F)C(F)(F)F)c(C(F)(F)F)c1-c1cc(-c2ccc(Cl)c(C(=O)NC3(C#N)CC3)c2)on1] | 1H NMR (400 MHz, dmso) δ 9.55 (s, 1H), 8.13 (s, 1H), 8.09 (d, J = 8.8 Hz, 1H), 7.78 (d, J = 8.3 Hz, 1H), 7.71 (s, 1H), 4.00 (s, 3H), 1.61 (d, 2H), 1.31 (d, 2H). 19F NMR (283 MHz, dmso) δ −62.46 (s, 3F), −88.29 (s, 3F), −122.73 (s, 2F), −129.29 (s, 2F), −133.57 (s, 2F). |
| 43 | 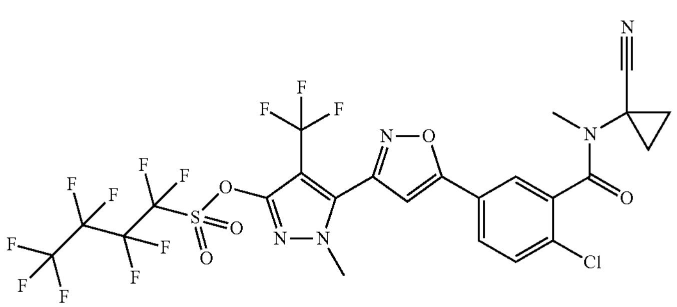 [SMILES: CN(C(=O)c1cc(-c2cc(-c3c(C(F)(F)F)c(OS(=O)(=O)C(F)(F)C(F)(F)C(F)(F)C(F)(F)F)nn3C)no2)ccc1Cl)C1(C#N)CC1] | 1H NMR (400 MHz, cdcl3) δ 8.05-7.78 (m, 2H), 7.61 (dd, J = 33.0, 7.8 Hz, 1H), 6.88 (d, J = 22.9 Hz, 1H), 4.07 (s, 3H), 3.26-2.98 (m, 3H), 1.49 (m, 2H), 1.31 (m, 2H). 19F NMR (283 MHz, CDCl3) δ −63.93 (d, J = 31.6 Hz, 3F), −89.59 (s, 3F), −116.89 (s, 2F), −129.76 (s, 2F), −134.82 (s, 2F). |

TABLE 1-continued

Examples of compounds of formula (I)

| Ex. No. | Structure | NMR data |
|---|---|---|
| 44 | 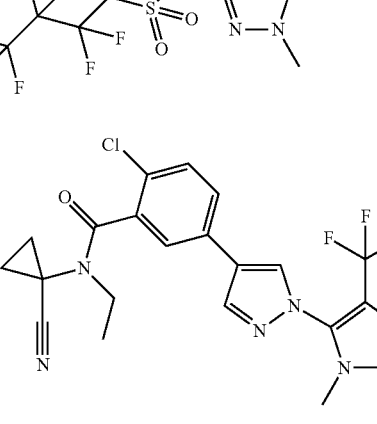 | 1H NMR (400 MHz, cdcl3) δ 8.03-7.77 (m, 2H), 7.66-7.56 (m, 1H), 6.89 (d, J = 23.0 Hz, 1H), 4.10 (s, 3H), 3.37 (m, 2H), 1.47 (s, 3H), 1.34 (m, 2H), 1.25 (m, 2H).<br>19F NMR (283 MHz, CDCl3) δ −64.06 (d, J = 32.7 Hz, 3F), −89.72 (s, 3F), −117.02 (s, 2F), −129.88 (s, 2F), −134.96 (s, 2F). |
| 45 | 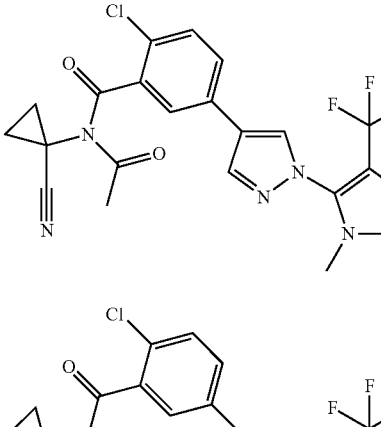 | 1H NMR (400 MHz, CD3OD) δ ppm 8.47-8.58 (m, 1 H) 8.34-8.44 (m, 1 H) 7.72-7.91 (m, 2 H) 7.53-7.59 (m, 1 H) 3.79 (s, 3 H) 3.32-3.60 (m, 2 H) 1.22-1.83 (m, 7 H)<br>19F NMR (377 MHz, CD3OD) δ ppm −58.01 (s, 3 F) −72.86 (s, 6 F) −166.94 (s, 1 F) |
| 46 | 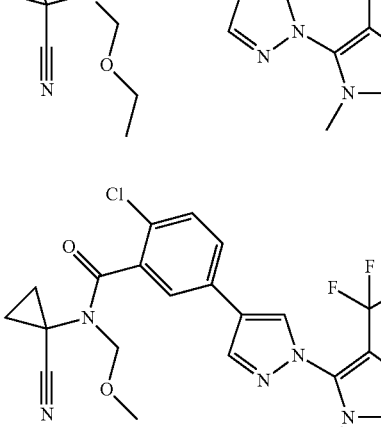 | 1H NMR (400 MHz, CDCl3) δ ppm 8.19 (s, 1 H) 8.04 (s, 1 H) 7.72 (d, 1 H) 7.61 (dd, 1 H) 7.52 (d, 1 H) 3.81 (s, 3 H) 2.55 (s, 3H) 1.36-1.78 (m, 4 H)<br>19F NMR (377 MHz, CDCl3) δ ppm −56.27 (s, 3 F) −71.28 (s, 6 F) −165.92 (m, 1 F) |
| 47 | 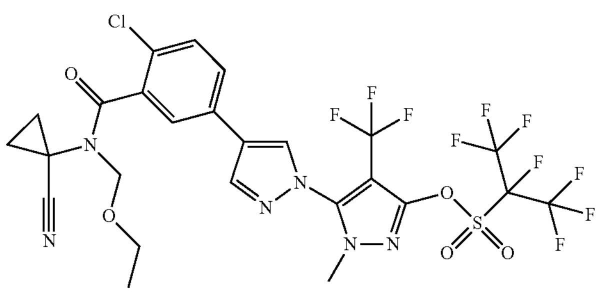 [SMILES: CCOCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | 1H NMR (400 MHz, CD3COCD3) δ ppm 8.65-8.72 (m, 1 H) 8.46-8.49 (m, 1 H) 7.86-8.01 (m, 2 H) 7.54-7.66 (m, 1 H) 4.57-4.82 (m, 2 H) 3.89 (s, 3 H) 3.37-3.76 (m, 2 H) 1.49-1.76 (m, 4 H) 0.85-1.10 (m, 3 H)<br>19F NMR (377 MHz, CD3COCD3) δ ppm −57.10 (s, 3 F) −72.18 (s, 6 F) −166.58 (s, 1 F) |
| 48 | 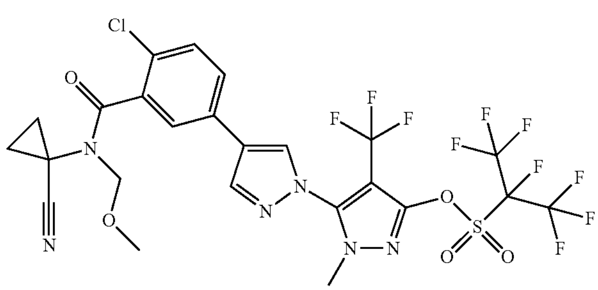 [SMILES: COCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | 1H NMR (400 MHz, CD3OD) δ ppm 8.49-8.55 (m, 1 H) 8.35-8.41 (m, 1 H) 7.73-8.03 (m, 2 H) 7.53-7.69 (m, 1 H) 4.94-5.25 and 4.45-4.79 (2xm, 2 H) 3.79 (s, 3 H) 3.51 and 3.23 (2xm, 2 H) 1.54-1.78 (m, 4 H)<br>19F NMR (377 MHz, CD3OD) δ ppm −58.01 (s, 3F) −72.85 (s, 6 F) −166.94 (s, 1 F) |

TABLE 1-continued

Examples of compounds of formula (I)

| Ex. No. | Structure | NMR data |
|---|---|---|
| 49 | 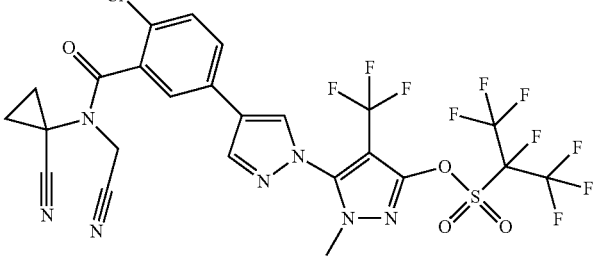 | 1H NMR (400 MHz, CD3OD) δ ppm 8.51 (s, 1 H) 8.38 (s, 1 H) 7.78-8.00 (m, 2 H) 7.58-7.66 (m, 1 H) 4.35-4.79 (m, 2 H) 3.79 (s, 3 H) 1.37-1.87 (m, 4 H) 19F NMR (377 MHz, CD3OD) δ ppm −57.97 (s, 3 F) −72.84 (s, 6 F) −166.94 (s, 1 F) |
| 50 | 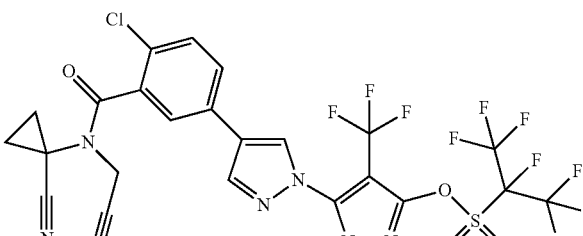 | 1H NMR (400 MHz, CD3OD) δ ppm 8.51 (br s, 1 H) 8.38 (s, 1 H) 7.77-7.94 (m, 2 H) 7.54 - 7.64 (m, 1 H) 4.02-4.76 (m, 2 H) 3.79 (s, 3 H) 2.86-2.92 (m, 1 H) 1.47-1.82 (m, 4 H) 19F NMR (377 MHz, CD3OD) δ ppm −57.99 (s, 3 F) −72.85 (s, 6 F) −166.93 (s, 1 F) |
| 51 | 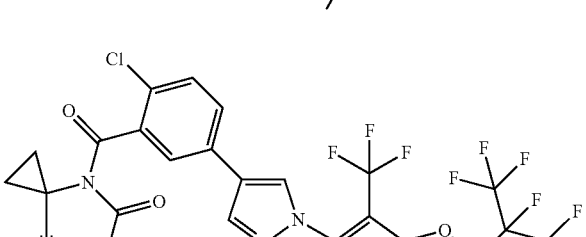 | 1H NMR (400 MHz, CD3OD) δ ppm 8.50 (s, 1 H) 8.36 (s, 1 H) 7.73-7.77 (m, 2 H) 7.46 (d, 1 H) 4.15 (q, 2 H) 3.79 (s, 3 H) 1.80-1.93 (m, 2 H) 1.52-1.67 (m, 2 H) 1.07 (t, 3 H) 19F NMR (377 MHz, CD3OD) δ ppm −57.98 (s, 3 F) −72.84 (s, 6 F) −166.93 (m, 1 F) |
| 52 | 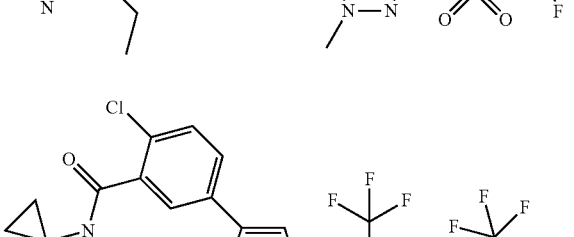 | 1H NMR (400 MHz, CD3OD) δ ppm 8.50 (s, 1 H) 8.37 (s, 1 H) 7.73-7.77 (m, 2 H) 7.47 (d, 1 H) 3.79 (s, 3 H) 3.75 (s, 3 H) 1.87 (d, 2 H) 1.60 (br d, 2 H) 19F NMR (377 MHz, CD3OD) δ ppm −58.01 (s, 3 F) −72.85 (s, 6 F) −166.94 (s, 1 F) |
| 54 | 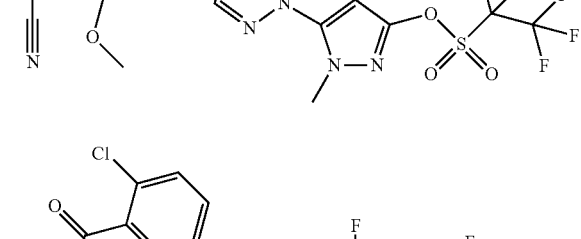 | 1H NMR (400 MHz, CD3OD) δ ppm 8.50 (s, 1 H) 8.38 (s, 1 H) 7.92 (d, 1 H) 7.80 (dd, 1 H) 7.55 (d, 1 H) 3.78 (s, 3 H) 2.87 (d, 2 H) 1.77-1.49 (m, 4 H) 1.14 (t, 3 H) 19F NMR (377 MHz, CD3OD) δ ppm −57.97 (s, 3 F) −72.85 (s, 6 F) −166.92 (m, 1 F) |

TABLE 1-continued

Examples of compounds of formula (I)

| Ex. No. | Structure | NMR data |
|---|---|---|
| 56 | 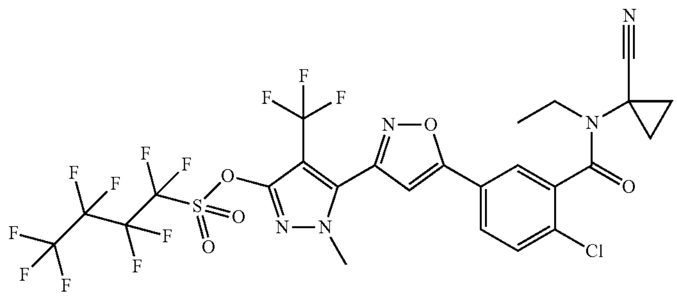 [SMILES: CCN(C(=O)c1cc(-c2cc(-c3c(C(F)(F)F)c(OS(=O)(=O)C(F)(F)C(F)(F)C(F)(F)C(F)(F)F)nn3C)no2)ccc1Cl)C1(C#N)CC1] | 1H NMR (400 MHz, CD3OD) δ ppm 8.49-8.56 (m, 1 H) 8.36-8.41 (m, 1 H) 7.73-7.92 (m, 2 H) 7.50-7.64 (m, 1 H) 3.86-4.02 and 3.33-3.65 (m, 2 H) 3.79 (s, 3 H) 1.40-1.63 (m, 4 H) 1.26-1.35 (m, 3 H) 19F NMR (377 MHz, CD3OD) δ ppm −57.92 (s, 3F) −82.25 (m, 2 F) 109.14 (m, 2 F) −121.87 (m, 2 F) −127.03 (m, 2 F) |
| 58 | 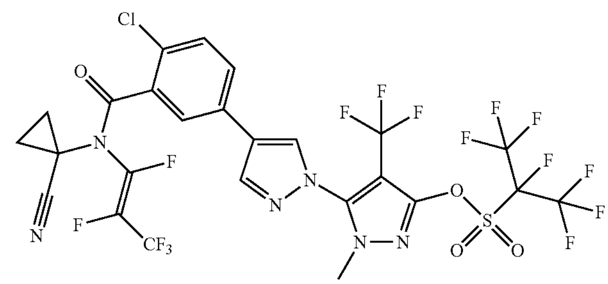 [SMILES: Cn1nc(OS(=O)(=O)C(F)(C(F)(F)F)C(F)(F)F)c(C(F)(F)F)c1-n1cc(-c2ccc(Cl)c(C(=O)N(/C(F)=C(\F)C(F)(F)F)C3(C#N)CC3)c2)cn1] | 1H NMR (400 MHz, CDCl3) δ ppm 8.11 (s, 1 H) 7.94 (s, 1 H) 7.42-7.67 (m, 3 H) 3.85 (s, 3 H) 1.43-1.91 (m, 4 H) 19F NMR (377 MHz, CDCl3) δ ppm −56.27 (s, 3 F) −68.56−−68.01 (m, 3 F) −71.37−−71.20 (m, 6 F) −112.40−−110.49 (m, 1 F) −161.22−−159.18 (m, 1 F) −165.84 (m, 1 F) |
| 59 | 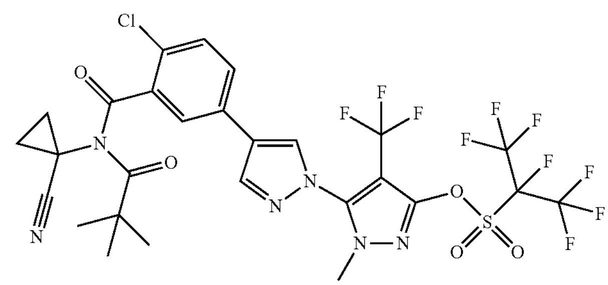 [SMILES: Cn1nc(OS(=O)(=O)C(F)(C(F)(F)F)C(F)(F)F)c(C(F)(F)F)c1-n1cc(-c2ccc(Cl)c(C(=O)N(C(=O)C(C)(C)C)C3(C#N)CC3)c2)cn1] | 1H NMR (400 MHz, CDCl3) δ ppm 8.19 (s, 1 H) 8.03 (s, 1 H) 7.78 (d, 1 H) 7.53-7.64 (m, 2 H) 3.83 (s, 3 H) 1.43-1.65 (m, 4 H) 1.39 (s, 9 H) 19F NMR (377 MHz, CDCl3) δ ppm −56.24 (s, 3 F) −71.35−−71.17 (m, 6 F) −165.90 (s, 1 F) |
| 60 | 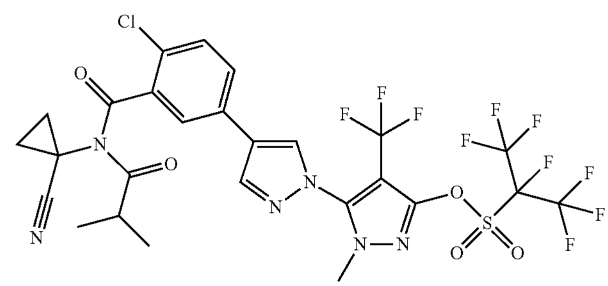 [SMILES: CC(C)C(=O)N(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | 1H NMR (400 MHz, CDCl3) δ ppm 8.18 (s, 1 H) 8.03 (s, 1 H) 7.70 (d, 1 H) 7.57-7.63 (m, 1 H) 7.52-7.57 (m, 1 H) 3.82 (s, 3 H) 3.42-3.54 (m, 1 H) 1.75-1.63 (m, 2 H) 1.36-1.50 (m, 3 H) 1.26 (d, 6 H) 19F NMR (377 MHz, CDCl3) δ ppm −56.24 (d, 3 F) −71.27 (d, F) −165.98−−165.83 (m, 1 F) |
| 62 | 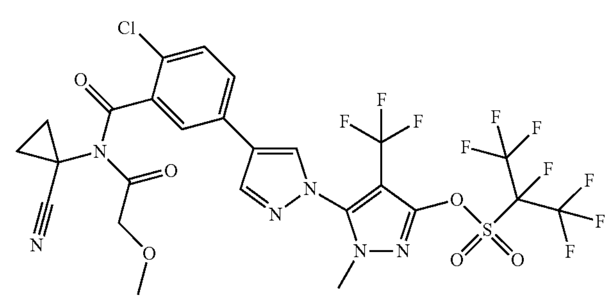 [SMILES: COCC(=O)N(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | 1H NMR (400 MHz, CDCl3) δ ppm 8.21 (s, 1 H) 8.07 (s, 1 H) 7.79 (d, 1 H) 7.62-7.70 (m, 1 H) 7.54-7.62 (m, 1 H) 4.55 (s, 2 H) 3.82 (s, 3H) 3.51 (s, 3 H) 1.63 (br s, 2 H) 1.34-1.50 (m, 2 H) 19F NMR (377 MHz, CDCl3) δ ppm −56.42−−56.14 (m, 3 F) −71.54−−71.14 (m, 6 F) −166.15−−165.78 (m, 1 F) |

TABLE 1-continued

Examples of compounds of formula (I)

| Ex. No. | Structure | NMR data |
|---|---|---|
| 64 | 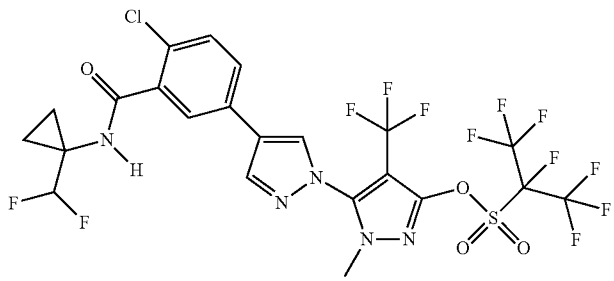 [SMILES: Cn1nc(OS(=O)(=O)C(F)(C(F)(F)F)C(F)(F)F)c(C(F)(F)F)c1-n1cc(-c2ccc(Cl)c(C(=O)NC3(C(F)F)CC3)c2)cn1] | 1H NMR (400 MHz, CDCl3) δ ppm 8.14 (s, 1 H) 7.96 (s, 1 H) 7.84 (d, 1 H) 7.54 (dd, 1 H) 7.47 (d, 1 H) 6.70 (brs, 1 H) 5.95-6.34 (m, 1 H) 3.84 (s, 3 H) 1.24-1.37 (m, 2 H) 1.07-1.13 (m, 2 H) 19F NMR (377 MHz, CDCl3) δ ppm −56.19 (m, 3F) −71.26 (d, 6 F) −124.89 (s, 2 F) −166.08-−165.76 (m, 1 F) |
| 65 | 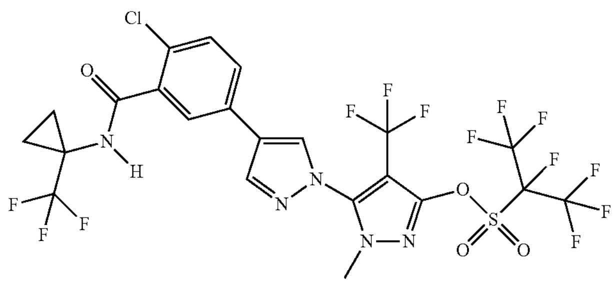 [SMILES: Cn1nc(OS(=O)(=O)C(F)(C(F)(F)F)C(F)(F)F)c(C(F)(F)F)c1-n1cc(-c2ccc(Cl)c(C(=O)NC3(C(F)(F)F)CC3)c2)cn1] | 1H NMR (400 MHz, CDCl3) δ ppm 8.15 (s, 1 H) 7.96 (s, 1 H) 7.84 (d, 1 H) 7.52-7.57 (m, 1 H) 7.47 (d, 1 H) 6.69 (s, 1 H) 3.84 (s, 3 H) 1.45-1.50 (m, 2 H) 1.27-1.35 (m, 2 H) 19F NMR (377 MHz, CDCl3) δ ppm −56.59-−56.01 (m, 3 F) −71.55-−71.05 (m, 6F) −74.12-−73.59 (m, 3 F) −166.48-−165.40 (m, 1 F) |
| 67 | 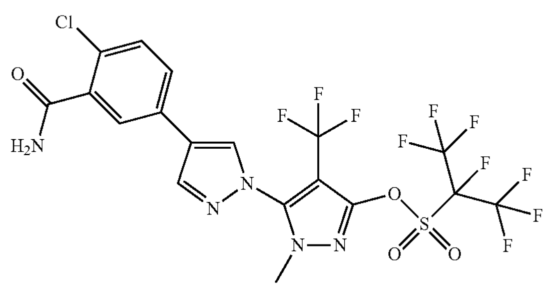 [SMILES: Cn1nc(OS(=O)(=O)C(F)(C(F)(F)F)C(F)(F)F)c(C(F)(F)F)c1-n1cc(-c2ccc(Cl)c(C(N)=O)c2)cn1] | 1H NMR (400 MHz, CDCl3) δ ppm 8.14-8.18 (m, 1 H) 8.02 (d, 1 H) 7.97 (s, 1 H) 7.53-7.59 (m, 1 H) 7.48-7.53 (m, 1 H) 6.50 (br s, 1 H) 6.01 (br s, 1 H) 3.84 (s, 3 H) 19F NMR (377 MHz, CDCl3) δ ppm −56.20 (d, 3 F) −71.35-−71.18 (m, 6 F) −166.03-−165.72 (m, 1 F) |
| 68 | 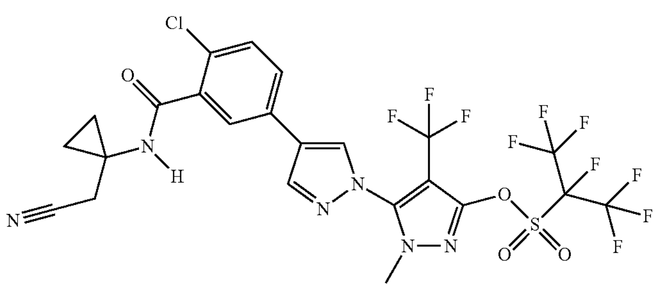 [SMILES: Cn1nc(OS(=O)(=O)C(F)(C(F)(F)F)C(F)(F)F)c(C(F)(F)F)c1-n1cc(-c2ccc(Cl)c(C(=O)NC3(CC#N)CC3)c2)cn1] | 1H NMR (400 MHz, CDCl3) δ ppm 8.15 (s, 1 H) 7.96 (s, 1 H) 7.83 (d, 1 H) 7.55 (dd, 1 H) 7.47 (d, 1 H) 6.81 (s, 1 H) 3.84 (s, 3 H) 2.93 (s, 2 H) 1.04-1.15 (m, 4 H) 19F NMR (377 MHz, CDCl3) δ ppm −56.18 (m, 1 F) −71.34-−71.17 (m, 1 F) −165.90 (m, 1 F) |
| 69 | 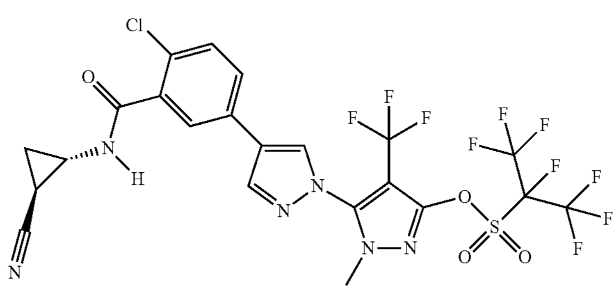 [SMILES: Cn1nc(OS(=O)(=O)C(F)(C(F)(F)F)C(F)(F)F)c(C(F)(F)F)c1-n1cc(-c2ccc(Cl)c(C(=O)N[C@H]3C[C@@H]3C#N)c2)cn1] | 1H NMR (600 MHz, CDCl3) δ ppm 1.47 (ddd, 1 H) 1.63 (dt, 1 H) 1.69 (ddd, 1 H) 3.49 (dddd, 1 H) 3.84 (s, 3 H) 6.65 (br s, 1 H) 7.47 (d, 1 H) 7.56 (dd, 1 H) 7.91 (d, 1 H) 7.96 (s, 1 H) 8.14 (s, 1 H) 19F NMR (377 MHz, CDCl3) δ ppm −165.89 (s, 1 F) −71.26 (m, 6 F) −56.18 (m, 3 F) |

TABLE 1-continued

Examples of compounds of formula (I)

| Ex. No. | Structure | NMR data |
|---|---|---|
| 71 | 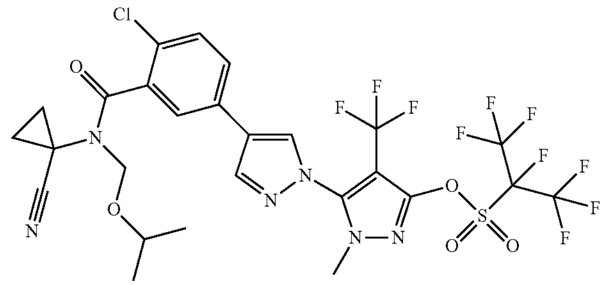 [SMILES: CC(C)OCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | $^1$H NMR (400 MHz, DMSO) δ 8.86 (m, 1H), 8.58 (m, 1H), 7.95-7.84 (m, 2H), 7.63 (m, 1H), 4.57 (d, J = 82.1 Hz, 2H), 3.80 (s, 3H), 3.61 (dt, J = 12.2, 6.1 Hz, 1H), 1.73 (m, 2H), 1.52 (m, 2H), 1.04-0.79 (m, 6H). 19F NMR (283 MHz, DMSO) δ −52.86 (s, 3F), −67.95 (d, J = 9.4 Hz, 6F), −163.00 (s, 1F). |
| 72 | 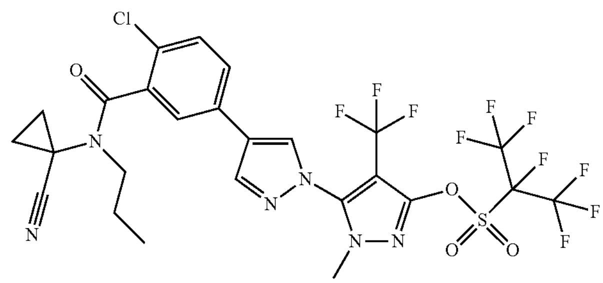 [SMILES: CCCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | 1H NMR (400 MHz, DMSO) δ 8.85 (m, 1H), 8.58 (m, 1H), 7.87 (m, 2H), 7.63 (m, 1H), 3.80 (s, 3H), 3.12 (m, 2H), 1.86-1.59 (m, 4H), 1.40 (m, 2H), 0.87-0.72 (m, 3H). 19F NMR (283 MHz, DMSO) δ −52.96 (s, 3F), −68.11 (s, 6F), −163.07 (s, 1F). |
| 73 | 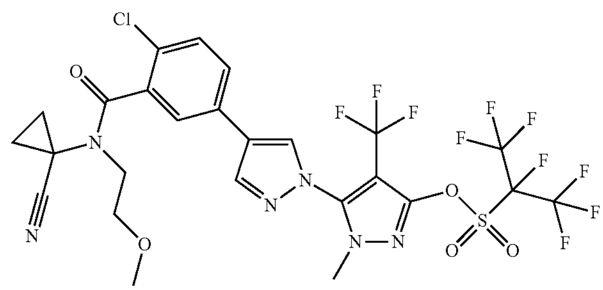 [SMILES: COCCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | $^1$H NMR (400 MHz, DMSO) δ 8.86-8.77 (m, 1H), 8.57-8.51 (m, 1H), 7.88-7.77 (m, 2H), 7.65-7.54 (m, 1H), 3.78 (s, 3H), 3.62-3.51 (m, 2H), 3.40-3.21 (m, 3H), 1.72-1.61 (m, 2H), 1.40-1.35 (m, 2H), 1.23-1.20 (m, 2H). $^{19}$F NMR (283 MHz, DMSO) δ −52.41 (s, 3F), −67.50 (s, 6F), −162.16 (s, 1F). |
| 74 | 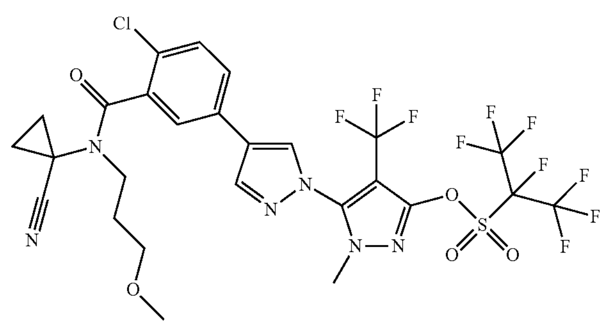 [SMILES: COCCCN(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | 1H NMR (400 MHz, DMSO) δ 8.89-8.82 (m, 1H), 8.62-8.55 (m, 1H), 7.93-7.83 (m, 2H), 7.67-7.58 (m, 1H), 3.80 (s, 3H), 3.38-2.97 (m, 7H), 1.94-1.61 (m, 4H), 1.39 (m, 2H). 19F NMR (283 MHz, DMSO) δ −51.55 (s, 3F), −64.25--68.20 (m, 6F), −161.74 (s, 1F). |
| 75 | 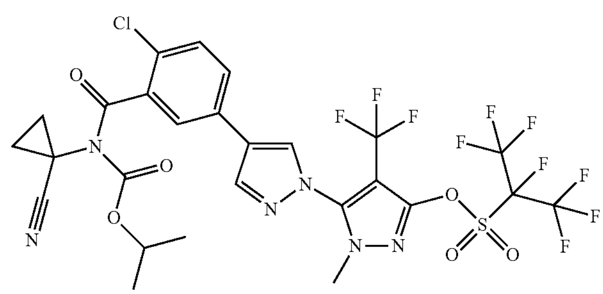 [SMILES: CC(C)OC(=O)N(C(=O)c1cc(-c2cnn(-c3c(C(F)(F)F)c(OS(=O)(=O)C(F)(C(F)(F)F)C(F)(F)F)nn3C)c2)ccc1Cl)C1(C#N)CC1] | 1H NMR (400 MHz, DMSO) δ 8.84 (s, 1H), 8.58 (s, 1H), 7.90-7.79 (m, 2H), 7.58 (d, J = 8.9 Hz, 1H), 4.81 (dt, J = 12.4, 6.2 Hz, 1H), 3.80 (s, 3H), 1.92 (m, 2H), 1.56 (m, 2H), 1.01 (d, J = 6.2 Hz, 6H). 19F NMR (283 MHz, DMSO) δ −51.55 (s, 3F), −66.64 (s, 6F), −161.67 (s,1F). |

The activity of the compositions according to the invention can be broadened considerably, and adapted to prevailing circumstances, by adding other insecticidally, acaricidally and/or fungicidally active ingredients. The mixtures of the compounds according to any one of embodiments 1 to 34 with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds according to any one of embodiments 1 to 34 with active ingredients are preferred (the abbreviation "TX" means "one compound selected from the compounds according to any one of embodiments 1 to 34, preferably embodiment 34):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin 11 (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, ometiate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+TX, pyrethrin 11 (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. kurstaki (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloro-propane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+

TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin 1 (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin 1 (696)+TX, jasmolin II (696)+TX, jodfenphos (1248)+TX, juvenile hormone I (alternative name) [CCN]+TX, juvenile hormone II (alternative name) [CCN]+TX, juvenile hormone lll (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O- diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-

30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a, 12,12a, 12b-decahydro-6,12-dihydroxy-4,6a,12b-trimethyl-11-oxo-9-(3-pyridinyl)-2H, 11 Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methyl propyl)-4-[2,2,2-trifluoro-1-methoxy-1-(trifluoromethyl) ethyl]phenyl]-1H-pyrazole-4-carboxamide [926914-55-8]+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright @ 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds according to any one of embodiments 1 to 34 with active ingredients described above comprises a compound according to any one of embodiments 1 to 34 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of according to any one of embodiments 1 to 34 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds according to any one of embodiments 1 to 34 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound according to any one of embodiments 1 to 34. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with according to any one of embodiments 1 to 34. Further, it is hereby made available, a composition comprising a plant propagation material treated with a compound according to any one of embodiments 1 to 34.

Seed treatment comprises all suitable seed treatment techniques known in the art, such as seed dressing, seed coating, seed dusting, seed soaking and seed pelleting. The seed treatment application of the compound according to any one of embodiments 1 to 34 can be carried out by any known methods, such as spraying or by dusting the seeds before sowing or during the sowing/planting of the seeds.

The pesticidal/insecticidal properties of the compounds according to any one of embodiments 1 to 34 can be illustrated via the following tests:

*Spodoptera littoralis* (Egyptian Cotton Leaf Worm)

Cotton leaf discs were placed on agar in 24-well microtiter plates and sprayed with aqueous test solutions prepared from 10'000 ppm DMSO stock solutions. After drying the leaf discs were infested with five L1 larvae. The samples were assessed for mortality, anti-feedant effect, and growth inhibition in comparison to untreated samples 3 days after infestation. Control of *Spodoptera littoralis* by a test sample is when at least one of mortality, anti-feedant effect, and growth inhibition is higher than the untreated sample. The following compounds resulted in at least 80% control at an application rate of 200 ppm: compounds 1, 2, 4, 5, 6, 7, 8, 9, 10, 11, 12, 13, 14, 15, 16, 17, 18, 19, 20, 21, 22, 23, 24, 25, 26, 27, 28, 30, 31, 32, 33, 34, 35, 36, 37, 38, 43, 44, 45, 46, 47, 48, 49, 50, 51, 52, 54, 56, 57, 58, 59, 60, 62, 64, 65, 67, 68, 69.

*Plutella xylostella* (Diamond Back Moth):

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation. The following compounds resulted in at least 80% control at an application rate of 200 ppm: compounds 1, 2, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 43, 44, 45, 46, 47, 48, 49, 50, 51, 52, 54, 56, 57, 58, 59, 60, 62, 64, 65, 67, 68, 69.

*Diabrotica Balteata*, (Corn Root Worm)

Maize sprouts, placed on an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation. The following compounds resulted in at least 80% control at an application rate of 200 ppm: compounds 1, 2, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 41, 43, 45, 46, 47, 48, 49, 50, 51, 52, 54, 56, 57, 58, 59, 60 and 62.

*Thrips tabaci* (Onion *Thrips*):

Sunflower leaf discs were placed on agar in 24-well microtiter plates and sprayed with aqueous test solutions prepared from 10'000 ppm DMSO stock solutions. After drying the leaf discs were infested with a *thrips* population of mixed ages. The samples were assessed for mortality 6 days after infestation. The following compounds resulted in at least 80% control at an application rate of 200 ppm: compounds 2, 5, 6, 7, 8, 9, 10, 11, 12, 13, 14, 17, 18, 19, 20, 21, 22, 25, 26, 27, 28, 31, 32, 33, 34, 35, 36, 37, 43, 45, 46, 47, 48, 49, 50, 51, 52, 54, 56, 57, 59, 60 and 62.

*Tetranychus urticae* (Two-Spotted Spider Mite):

Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation. The following compounds resulted in at least 80% control at an application rate of 200 ppm: compounds 1, 2, 5, 8, 9, 10, 12, 17, 18, 19, 20, 21, 22, 23, 24, 25, 26, 33, 34, 35, 36, 37, 38, 45, 46, 48, 49, 50, 51, 52, 54, 57, 58, 59, 60, 62, 64, 65, 67, 68, 69.

*Euschistus heros* (Neotropical Brown Stink Bug):

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation. The following compounds resulted in at least 80% control at an application rate of 200 ppm: compounds 1, 2, 5, 6, 9, 12, 18, 21, 25 32, 33, 34, 35, 36, 37, 38, 45, 46, 47, 48, 49, 50, 51, 52, 54, 57, 59, 60, 62, 65, 68, 69.

*Myzus persicae* (Green Peach Aphid):

Sunflower leaf discs were placed on agar in a 24-well microtiter plate and sprayed with test solutions at an application rate of 200 ppm. After drying, the leaf discs were infested with an aphid population of mixed ages. After an incubation period of 6 DAT, samples were checked for mortality. The following compounds resulted in at least 80% control at an application rate of 200 ppm: compounds 2, 5, 8, 9, 10, 12, 14, 17, 18, 19, 21,22, 23, 25, 26, 27, 29, 33, 34, 35, 36, 37, 38, 41, 45, 46, 47, 48, 49, 50, 51, 52, 54, 57, 59, 60, 62, 64, 69.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Furthermore, besides of the insecticidal properties, the compounds according to any one of embodiments 1 to 34 have surprisingly shown to have improved degradation properties compared with prior art compounds. Additionally, the compounds according to any one of embodiments 1 to 34 have surprisingly shown to be environmentally more tolerated than prior art compounds.

What is claimed is:

1. A compound of formula (I),

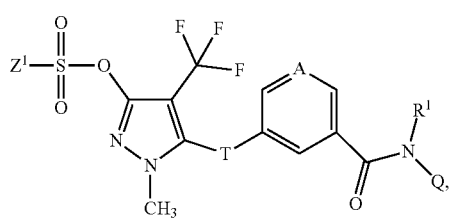

(I)

wherein
$Z^1$ is selected from $C_1$-$C_4$ haloalkyl and F;
T is selected from

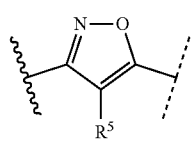 T1

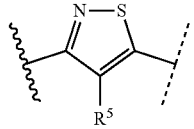 T2

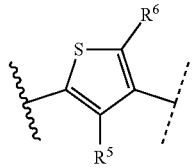 T3

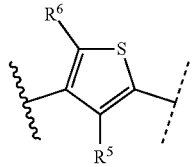 T4

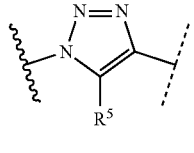 T5

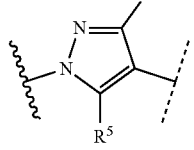 T6 wherein ⊢ indicates the bond to the pyrazole group;
$R^5$ and $R^6$ are independently selected from H, methyl and trifluoromethoxy;
A is selected from C—H and N;
$R^2$ is selected from H, methyl, trifluoromethyl and halogen;
$R^1$ is selected from H, $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, formyl, $C_1$-$C_6$-alkoxycarbonyl, aryl($C_0$-$C_3$)-alkyl and heteroaryl($C_0$-$C_3$)-alkyl, wherein each of $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, $C_1$-$C_6$-alkoxycarbonyl, aryl($C_0$-$C_3$)-alkyl and heteroaryl($C_0$-$C_3$)-alkyl is unsubstituted or substituted with 1 to 10 substituents independently selected from halogen, cyano, $C_1$-$C_6$-alkoxy and $C_1$-$C_6$-alkoxycarbonyl;
Q is selected from H, hydroxy, HC(=O)—, $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N-$C_1$-$C_6$-alkylamino, N-$C_1$-$C_6$-alkylcarbonylamino and N,N-di ($C_1$-$C_6$-alkyl)amino, wherein each of $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N-$C_1$-$C_6$-alkylamino, N-$C_1$-$C_6$-alkylcarbonylamino and N,N-di ($C_1$-$C_6$-alkyl)amino is unsubstituted or substituted with 1 to 10 substituents independently selected from halogen, hydroxyl, nitro, amino, cyano, $C_1$-$C_6$-alkoxy, $C_1$-$C_6$- alkoxycarbonyl, hydroxycarbonyl, $C_1$-$C_6$-alkylcarbamoyl, $C_3$-$C_6$-cycloalkylcarbamoyl and phenyl;

wherein the compound of formula (I) is not [5-[4-[4-chloro-3-[(1-cyanocyclopropyl)carbamoyl]phenyl]pyrazol-1-yl]-1-methyl-4-(trifluoromethyl)pyrazol-3-yl] trifluoromethanesulfonate, or [5-[4-[4-chloro-3-(cyanocyclopropylcarbamoyl)phenyl]pyrazol-1-yl]-1-methyl-4-(trifluoromethyl)pyrazol-3-yl] 1,1,2,2,3,3,4,4-nonafluorobutane-1-sulfonate, or [5-[4-[4-chloro-3-(cyclopropylcarbamoyl)phenyl]pyrazol-1-yl]-1-methyl-4-(trifluoromethyl)pyrazol-3-yl] 1,1,2,2,3,3,4,4-nonafluorobutane-1-sulfonate;

or an agrochemically acceptable salt or N-oxide thereof.

2. A compound or salt according to claim 1 of formula (I)

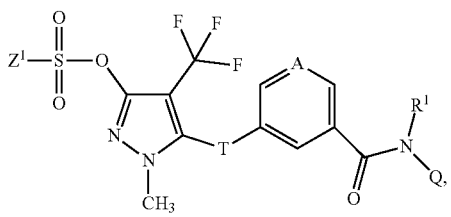

wherein $Z^1$ is selected from $C_1$-$C_4$ haloalkyl and F;

T is selected from

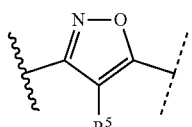 T1

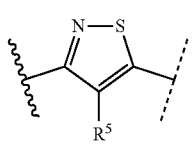 T2

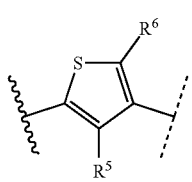 T3

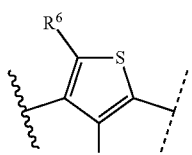 T4

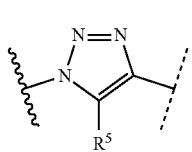 T5

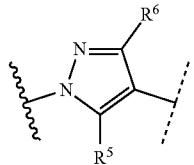 T6 wherein ⊢ indicates the bond to the pyrazole group;

$R^5$ and $R^6$ are independently selected from H, methyl and trifluoromethoxy;

A is selected from C—H and N;

$R^2$ is selected from H, methyl, trifluoromethyl and halogen;

$R^1$ is selected from H, $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, formyl, $C_1$-$C_6$-alkoxycarbonyl, aryl($C_0$-$C_3$)-alkyl and heteroaryl($C_0$-$C_3$)-alkyl, wherein each of $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, $C_1$-$C_6$-alkoxycarbonyl, aryl($C_0$-$C_3$)-alkyl and heteroaryl($C_0$-$C_3$)-alkyl is unsubstituted or substituted with 1 to 10 substituents independently selected from halogen, cyano, $C_1$-$C_6$-alkoxy and $C_1$-$C_6$-alkoxycarbonyl;

Q is selected from H, hydroxy, HC(=O)—, $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N-$C_1$-$C_6$-alkylamino, N-$C_1$-$C_6$-alkylcarbonylamino and N,N-di ($C_1$-$C_6$-alkyl)amino, wherein each of $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N-$C_1$-$C_6$-alkylamino, N-$C_1$-$C_6$-alkylcarbonylamino and N,N-di ($C_1$-$C_6$-alkyl)amino is unsubstituted or substituted with 1 to 10 substituents independently selected from halogen, hydroxyl, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

with the proviso that when T is T6, A is C—H, $R^5$ and $R^6$ are H, $Z^1$ is $CF_3$ or $CF_2CF_2CF_2CF_3$, and Q is cyclopropyl or 1-cyanocyclopropyl, then $R^1$ is not H;

or an agrochemically acceptable salt or N-oxide thereof.

3. A compound or salt according to claim 1 of formula (I)

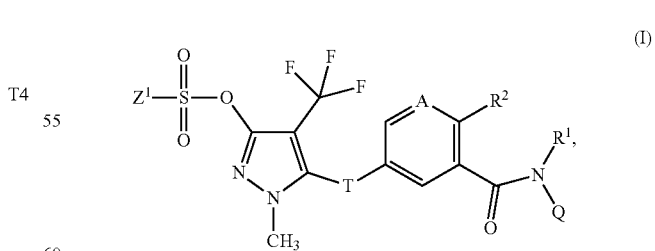

wherein $Z^1$ is selected from

F, $CF_2CF_3$, $CF_2CF_2C_1$, $CF_2CFCl_2$, $CF_2CF_2CF_3$,
$CF(CF_3)(CF_3)$,
$CF_2CF_2CF_2C_1$,
$CF(CF_3)(CF_2C_1)$,
$CF_2CF_2CFCl_2$,
$CF(CF_3)(CFCl_2)$,
$CF_2CF_2CF_2CF_3$,
$CF(CF_3)CF_2CF_3$,
$CF_2CF(CF_3)(CF_3)$,
$C(CF_3)(CF_3)(CF_3)$;

T is selected from

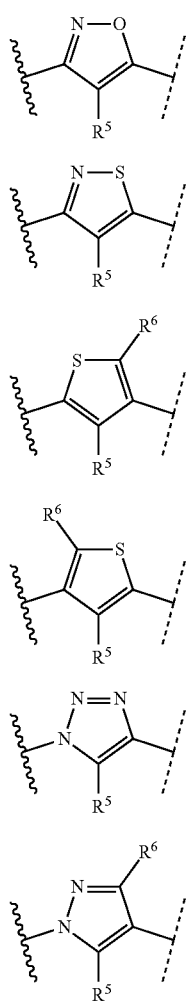

wherein ⊢ indicates the bond to the pyrazole group;
$R^5$ and $R^6$ are independently selected from H, methyl and trifluoromethoxy;
A is selected from C—H and N;
$R^2$ is selected from H, methyl, trifluoromethyl and halogen;
$R^1$ is selected from H, $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, formyl, $C_1$-$C_6$-alkoxycarbonyl, aryl($C_0$-$C_3$)-alkyl and heteroaryl($C_0$-$C_3$)-alkyl, wherein each of $C_1$-$C_6$-alkyl, $C_2$-$C_6$ alkenyl, $C_2$-$C_6$ alkynyl, $C_3$-$C_7$ cycloalkyl, $C_3$-$C_7$ cycloalkyl-$C_1$-$C_3$-alkyl, $C_1$-$C_6$-alkylcarbonyl, $C_1$-$C_6$-alkoxycarbonyl, aryl($C_0$-$C_3$)-alkyl and heteroaryl($C_0$-$C_3$)-alkyl is unsubstituted or substituted with 1 to 10 substituents independently selected from halogen, cyano, $C_1$-$C_6$-alkoxy and $C_1$-$C_6$-alkoxycarbonyl;

Q is selected from H, hydroxy, HC(=O)—, $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N-$C_1$-$C_6$-alkylamino, N-$C_1$-$C_6$-alkylcarbonylamino and N,N-di ($C_1$-$C_6$-alkyl)amino, wherein each of $C_1$-$C_6$-alkyl, $C_1$-$C_6$-alkoxy, $C_3$-$C_6$ alkenyl, $C_3$-$C_6$ alkynyl, $C_3$-$C_7$ cycloalkyl, $C_3$-$C_7$ heterocycloalkyl, $C_3$-$C_7$ cycloalkyl-$C_1$-$C_3$-alkyl, $C_1$-$C_3$-alkyl-$C_3$-$C_7$ cycloalkyl, aryl($C_0$-$C_3$)-alkyl, heteroaryl($C_0$-$C_3$)-alkyl, N-$C_1$-$C_6$-alkylamino, N-$C_1$-$C_6$-alkylcarbonylamino and N,N-di ($C_1$-$C_6$-alkyl)amino is unsubstituted or substituted with 1 to 10 substituents independently selected from halogen, hydroxyl, nitro, amino, cyano, $C_1$-$C_6$-alkoxy, $C_1$-$C_6$-alkoxycarbonyl, hydroxycarbonyl, $C_1$-$C_6$-alkylcarbamoyl, $C_3$-$C_6$-cycloalkylcarbamoyl and phenyl;

with the proviso that when T is T6, A is C—H, $R^5$ and $R^6$ are H, $Z^1$ is $CF_3$ or $CF_2CF_2CF_2CF_3$, and Q is cyclopropyl or 1-cyanocyclopropyl, then $R^1$ is not H;

or an agrochemically acceptable salt or N-oxide thereof.

4. A compound or salt according to claim 1 of formula (Ia)

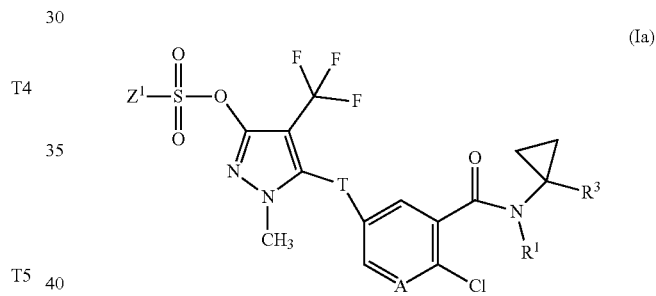

(Ia)

wherein $Z^1$ is $CF(CF_3)(CF_3)$;
$R^1$ is selected from H, $C_1$-$C_6$-alkyl, $C_2$-$C_6$ alkenyl, $C_2$-$C_6$ alkynyl, $C_1$-$C_6$-alkylcarbonyl and $C_1$-$C_6$-alkoxycarbonyl, wherein each of $C_1$-$C_6$-alkyl, $C_2$-$C_6$ alkenyl, $C_2$-$C_6$ alkynyl, $C_1$-$C_6$-alkylcarbonyl and $C_1$-$C_6$-alkoxycarbonyl is unsubstituted or substituted with 1 to 10 substituents independently selected from halogen, cyano, $C_1$-$C_6$-alkoxy and $C_1$-$C_6$-alkoxycarbonyl;
A is selected from C—H and N;
$R^3$ is selected from H and CN;
T is

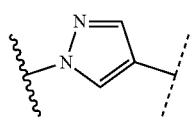

T6 or an agrochemically acceptable salt or N-oxide thereof.

5. A compound or salt according to claim 1 of formula (Ia)

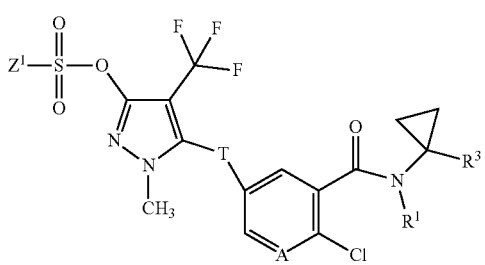

(Ia)

wherein
Z¹ is $CF(CF_3)(CF_3)$;
1e is selected from H, $C_1$-$C_6$-alkyl, $C_2$-$C_6$ alkenyl, $C_2$-$C_6$ alkynyl, $C_1$-$C_6$-alkylcarbonyl and $C_1$-$C_6$-alkoxycarbonyl, wherein each of $C_1$-$C_6$-alkyl, $C_2$-$C_6$ alkenyl, $C_2$-$C_6$ alkynyl, $C_1$-$C_6$-alkylcarbonyl and $C_1$-$C_6$-alkoxycarbonyl is unsubstituted or substituted with 1 to 10 substituents independently selected from halogen, cyano, $C_1$-$C_6$-alkoxy and $C_1$-$C_6$-alkoxycarbonyl;
A is selected from C—H and N;
R³ is selected from H and CN;
T is selected from

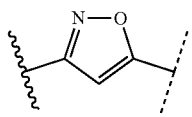

T1 or an agrochemically acceptable salt or N-oxide thereof.

6. A pesticidal composition, which comprises at least one compound according to claim 1, or an agrochemically acceptable salt or N-oxide thereof, as active ingredient and at least one auxiliary.

7. The composition according to claim 6, which further comprises one or more other insecticidally, acaricidally, nematicidally and/or fungicidally active agents.

8. A method for controlling and preventing pests, which comprises applying a composition according to claim 6 to the pests or their environment with the exception of a method for treatment of the human or animal body by surgery or therapy.

9. A method for the protection of plant propagation material from the attack by pests, which comprises treating the propagation material or the site, where the propagation material is planted, with a composition according to claim 6.

10. A coated plant propagation material, wherein the coating of the plant propagation material comprises a compound as defined in claim 1.

11. A compound selected from:
[5-[4-[4-chloro-3-[(1-cyanocyclopropyl)carbamoyl]phenyl]pyrazol-1-yl]-1-methyl-4-(trifluoromethyl)pyrazol-3-yl] 1,1,2,2,2-pentafluoroethanesulfonate;
[5-[4-[4-chloro-3-[(1-cyanocyclopropyl)carbamoyl]phenyl]pyrazol-1-yl]-1-methyl-4-(trifluoromethyl)pyrazol-3-yl] 1,1,1,2,3,3,3-heptafluoropropane-2-sulfonate;
5-[4-[4-chloro-3-[(1-cyanocyclopropyl)carbamoyl]phenyl]pyrazol-1-yl]-3-fluorosulfonyloxy-1-methyl-4-(trifluoromethyl)pyrazole;
5-[4-[4-chloro-3-(cyclopropylcarbamoyl)phenyl]pyrazol-1-yl]-3-fluorosulfonyloxy-1-methyl-4-(trifluoromethyl)pyrazole; 5-[4-[4-chloro-3-(cyclopropylcarbamoyl)phenyl]pyrazol-1-yl]-1-methyl-4-(trifluoromethyl)pyrazol-3-yl] 1,1,1,2,3,3,3-heptafluoropropane-2-sulfonate;
[5-[4-[4-chloro-3-[(1-cyanocyclopropyl)-methyl-carbamoyl]phenyl]pyrazol-1-yl]-1-methyl-4-(trifluoromethyl)pyrazol-3-yl] 1,1,2,2,3,3,4,4,4-nonafluorobutane-1-sulfonate;
[5-[4-[4-chloro-3-[(1-cyanocyclopropyl)-methyl-carbamoyl]phenyl]pyrazol-1-yl]-1-methyl-4-(trifluoromethyl)pyrazol-3-yl] 1,1,2,2,2-pentafluoroethanesulfonate;
[5-[4-[4-chloro-3-[(1-cyanocyclopropyl)carbamoyl]phenyl]pyrazol-1-yl]-1-methyl-4-(trifluoromethyl)pyrazol-3-yl] 2-chloro-1,1,2,2-tetrafluoro-ethanesulfonate;
[5-[4-[4-chloro-3-(cyclopropylcarbamoyl)phenyl]pyrazol-1-yl]-1-methyl-4-(trifluoromethyl)pyrazol-3-yl] 2-chloro-1,1,2,2-tetrafluoro-ethanesulfonate;
5-[4-[4-chloro-3-[cyclopropyl(ethyl)carbamoyl]phenyl]pyrazol-1-yl]-1-methyl-4-(trifluoromethyl)pyrazol-3-yl] 2-chloro-1,1,2,2-tetrafluoro-ethanesulfonate;
[5-[4-[4-chloro-3-[cyclopropyl(methyl)carbamoyl]phenyl]pyrazol-1-yl]-1-methyl-4-(trifluoromethyl)pyrazol-3-yl] 2-chloro-1,1,2,2-tetrafluoro-ethanesulfonate;
[5-[4-[4-chloro-3-[cyclopropyl(ethyl)carbamoyl]phenyl]pyrazol-1-yl]-1-methyl-4-(trifluoromethyl)pyrazol-3-yl] 1,1,1,2,3,3,3-heptafluoropropane-2-sulfonate;
[5-[4-[4-chloro-3-[cyclopropyl(ethyl)carbamoyl]phenyl]pyrazol-1-yl]-1-methyl-4-(trifluoromethyl)pyrazol-3-yl] 1,1,2,2,3,3,4,4,4-nonafluorobutane-1-sulfonate;
[5-[4-[4-chloro-3-[cyclopropyl(ethyl)carbamoyl]phenyl]pyrazol-1-yl]-1-methyl-4-(trifluoromethyl)pyrazol-3-yl] 1,1,2,2,2-pentafluoroethanesulfonate;
[5-[4-[4-chloro-3-[cyclopropyl(methyl)carbamoyl]phenyl]pyrazol-1-yl]-1-methyl-4-(trifluoromethyl)pyrazol-3-yl] 1,1,2,2,3,3,4,4,4-nonafluorobutane-1-sulfonate;
[5-[4-[4-chloro-3-[cyclopropyl(methyl)carbamoyl]phenyl]pyrazol-1-yl]-1-methyl-4-(trifluoromethyl)pyrazol-3-yl] 1,1,2,2,2-pentafluoroethanesulfonate;
[5-[4-[4-chloro-3-[cyclopropyl(methyl)carbamoyl]phenyl]pyrazol-1-yl]-1-methyl-4-(trifluoromethyl)pyrazol-3-yl] 1,1,1,2,3,3,3-heptafluoropropane-2-sulfonate;
[5-[4-[4-chloro-3-[(1-cyanocyclopropyl)-methyl-carbamoyl]phenyl]pyrazol-1-yl]-1-methyl-4-(trifluoromethyl)pyrazol-3-yl] 1,1,1,2,3,3,3-heptafluoropropane-2-sulfonate;
[5-[4-[4-chloro-3-[(1-cyanocyclopropyl)-methyl-carbamoyl]phenyl]pyrazol-1-yl]-1-methyl-4-(trifluoromethyl)pyrazol-3-yl] 2-chloro-1,1,2,2-tetrafluoro-ethanesulfonate;
[5-[4-[4-chloro-3-(cyclopropylcarbamoyl)phenyl]pyrazol-1-yl]-1-methyl-4-(trifluoromethyl)pyrazol-3-yl] 1,1,2,2,2-pentafluoroethanesulfonate;
[5-[4-[6-chloro-5-(cyclopropylcarbamoyl)-3-pyridyl]pyrazol-1-yl]-1-methyl-4-(trifluoromethyl)pyrazol-3-yl] 1,1,1,2,3,3,3-heptafluoropropane-2-sulfonate;
[5-[4-[6-chloro-5-[cyclopropyl(methyl)carbamoyl]-3-pyridyl]pyrazol-1-yl]-1-methyl-4-(trifluoromethyl)pyrazol-3-yl] 1,1,1,2,3,3,3-heptafluoropropane-2-sulfonate;
[5-[4-[4-chloro-5-[cyclopropyl(ethyl)carbamoyl]-3-pyridyl]pyrazol-1-yl]-1-methyl-4-(trifluoromethyl)pyrazol-3-yl] 1,1,1,2,3,3,3-heptafluoropropane-2-sulfonate;

[5-[4-[6-chloro-5-[(1-cyanocyclopropyl)carbamoyl]-3-pyridyl]pyrazol-1-yl]-1-methyl-4-(trifluoromethyl)pyrazol-3-yl] 1,1,1,2,3,3,3-heptafluoropropane-2-sulfonate;

[5-[4-[6-chloro-5-[(1-cyanocyclopropyl)-methyl-carbamoyl]-3-pyridyl]pyrazol-1-yl]-1-methyl-4-(trifluoromethyl)pyrazol-3-yl] 1,1,1,2,3,3,3-heptafluoropropane-2-sulfonate;

[5-[4-[6-chloro-5-[(1-cyanocyclopropyl)-ethyl-carbamoyl]-3-pyridyl]pyrazol-1-yl]-1-methyl-4-(trifluoromethyl)pyrazol-3-yl] 1,1,1,2,3,3,3-heptafluoropropane-2-sulfonate;

[5-[4-[6-chloro-5-(cyclopropylcarbamoyl)-3-pyridyl]pyrazol-1-yl]-1-methyl-4-(trifluoromethyl)pyrazol-3-yl] 1,1,2,2,3,3,4,4,4-nonafluorobutane-1-sulfonate;

[5-[4-[6-chloro-5-[cyclopropyl(methyl)carbamoyl]-3-pyridyl]pyrazol-1-yl]-1-methyl-4-(trifluoromethyl)pyrazol-3-yl] 1,1,2,2,3,3,4,4,4-nonafluorobutane-1-sulfonate;

[5-[4-[6-chloro-5-[cyclopropyl(ethyl)carbamoyl]-3-pyridyl]pyrazol-1-yl]-1-methyl-4-(trifluoromethyl)pyrazol-3-yl] 1,1,2,2,3,3,4,4,4-nonafluorobutane-1-sulfonate;

[5-[4-[6-chloro-5-[(1-cyanocyclopropyl)carbamoyl]-3-pyridyl]pyrazol-1-yl]-1-methyl-4-(trifluoromethyl)pyrazol-3-yl] 1,1,2,2,3,3,4,4,4-nonafluorobutane-1-sulfonate;

[5-[4-[6-chloro-5-[(1-cyanocyclopropyl)-methyl-carbamoyl]-3-pyridyl]pyrazol-1-yl]-1-methyl-4-(trifluoromethyl)pyrazol-3-yl] 1,1,2,2,3,3,4,4,4-nonafluorobutane-1-sulfonate;

[5-[4-[6-chloro-5-[(1-cyanocyclopropyl)-ethyl-carbamoyl]-3-pyridyl]pyrazol-1-yl]-1-methyl-4-(trifluoromethyl)pyrazol-3-yl] 1,1,2,2,3,3,4,4,4-nonafluorobutane-1-sulfonate;

[5-[5-[4-chloro-3-(cyclopropylcarbamoyl)phenyl]isoxazol-3-yl]-1-methyl-4-(trifluoromethyl)pyrazol-3-yl] 1,1,1,2,3,3,3-heptafluoropropane-2-sulfonate;

[5-[5-[4-chloro-3-[cyclopropyl(methyl)carbamoyl]phenyl]isoxazol-3-yl]-1-methyl-4-(trifluoromethyl)pyrazol-3-yl] 1,1,1,2,3,3,3-heptafluoropropane-2-sulfonate;

[5-[5-[4-chloro-3-[cyclopropyl(ethyl)carbamoyl]phenyl]isoxazol-3-yl]-1-methyl-4-(trifluoromethyl)pyrazol-3-yl] 1,1,1,2,3,3,3-heptafluoropropane-2-sulfonate;

[5-[5-[4-chloro-3-[(1-cyanocyclopropyl)carbamoyl]phenyl]isoxazol-3-yl]-1-methyl-4-(trifluoromethyl)pyrazol-3-yl] 1,1,1,2,3,3,3-heptafluoropropane-2-sulfonate;

[5-[5-[4-chloro-3-[(1-cyanocyclopropyl)-methyl-carbamoyl]phenyl]isoxazol-3-yl]-1-methyl-4-(trifluoromethyl)pyrazol-3-yl] 1,1,1,2,3,3,3-heptafluoropropane-2-sulfonate;

[5-[5-[4-chloro-3-[(1-cyanocyclopropyl)-ethyl-carbamoyl]phenyl]isoxazol-3-yl]-1-methyl-4-(trifluoromethyl)pyrazol-3-yl] 1,1,1,2,3,3,3-heptafluoropropane-2-sulfonate;

[5-[5-[4-chloro-3-(cyclopropylcarbamoyl)phenyl]isoxazol-3-yl]-1-methyl-4-(trifluoromethyl)pyrazol-3-yl] 1,1,2,2,3,3,4,4,4-nonafluorobutane-1-sulfonate;

[5-[5-[4-chloro-3-[cyclopropyl(methyl)carbamoyl]phenyl]isoxazol-3-yl]-1-methyl-4-(trifluoromethyl)pyrazol-3-yl] 1,1,2,2,3,3,4,4,4-nonafluorobutane-1-sulfonate;

[5-[5-[4-chloro-3-[cyclopropyl(ethyl)carbamoyl]phenyl]isoxazol-3-yl]-1-methyl-4-(trifluoromethyl)pyrazol-3-yl] 1,1,2,2,3,3,4,4,4-nonafluorobutane-1-sulfonate;

[5-[5-[4-chloro-3-[(1-cyanocyclopropyl)carbamoyl]phenyl]isoxazol-3-yl]-1-methyl-4-(trifluoromethyl)pyrazol-3-yl] 1,1,2,2,3,3,4,4,4-nonafluorobutane-1-sulfonate;

[5-[5-[4-chloro-3-[(1-cyanocyclopropyl)-methyl-carbamoyl]phenyl]isoxazol-3-yl]-1-methyl-4-(trifluoromethyl)pyrazol-3-yl] 1,1,2,2,3,3,4,4,4-nonafluorobutane-1-sulfonate;

[5-[5-[4-chloro-3-[(1-cyanocyclopropyl)-ethyl-carbamoyl]phenyl]isoxazol-3-yl]-1-methyl-4-(trifluoromethyl)pyrazol-3-yl] 1,1,2,2,3,3,4,4,4-nonafluorobutane-1-sulfonate;

[5-[4-[4-chloro-3-[(1-cyanocyclopropyl)-ethyl-carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[3-[acetyl-(1-cyanocyclopropyl)carbamoyl]-4-chloro-phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-(ethoxymethyl)carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-(methoxymethyl)carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-(cyanomethyl)carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-prop-2-ynyl-carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-ethoxycarbonyl-carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-methoxycarbonyl-carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-propanoyl-carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-ethyl-carbamoyl]phenyl]pyrazol-1-yl]-1-methyl-4-(trifluoromethyl)pyrazol-3-yl] 1,1,2,2,3,3,4,4,4-nonafluorobutane-1-sulfonate;

[5-[4-[4-chloro-3-[(1-cyanocyclopropyl)-formyl-carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-[(E)-1,2,3,3,3-pentafluoroprop-1-enyl]carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-(2,2-dimethylpropanoyl)carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-(2-methylpropanoyl)carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-(2-methoxyacetyl)carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[[1-(difluoromethyl)cyclopropyl] carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[[1-(trifluoromethyl)cyclopropyl]carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-(3-carbamoyl-4-chloro-phenyl)pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[[1-(cyanomethyl)cyclopropyl]carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-(isopropoxymethyl)carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-(isopropoxymethyl)carbamoyl]phenyl]pyrazol-1-yl]-1-methyl-4-(trifluoromethyl)pyrazol-3-yl] 1,1,1,2,3,3,3-heptafluoropropane-2-sulfonate;

5-[4-[4-chloro-3-[(1-cyanocyclopropyl)-propyl-carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-(2-methoxyethyl)carbamoyl]phenyl]pyrazol-1-yl]-1-methyl-4-(trifluoromethyl)pyrazol-3-yl] 1,1,1,2,3,3,3-heptafluoropropane-2-sulfonate;

[5-[4-[4-chloro-3-[(1-cyanocyclopropyl)-(3-methoxypropyl)carbamoyl]phenyl]pyrazol-1-yl]-1-methyl-4-(trifluoromethyl)pyrazol-3-yl] 1,1,1,2,3,3,3-heptafluoropropane-2-sulfonate; or

[5-[4-[4-chloro-3-[(1-cyanocyclopropyl)-isopropoxycarbonyl-carbamoyl]phenyl]pyrazol-1-yl]-1-methyl-4-(trifluoromethyl)pyrazol-3-yl] 1,1,1,2,3,3,3-heptafluoropropane-2-sulfonate.

\* \* \* \* \*